US010457737B2

(12) United States Patent
Georgiou et al.

(10) Patent No.: US 10,457,737 B2
(45) Date of Patent: Oct. 29, 2019

(54) ENGINEERED IMMUNOGLOBULIN FC POLYPEPTIDES DISPLAYING IMPROVED COMPLEMENT ACTIVATION

(71) Applicant: Research Development Foundation, Carson City, NV (US)

(72) Inventors: George Georgiou, Austin, TX (US); Chang-Han Lee, Austin, TX (US)

(73) Assignee: Research Development Foundation, Carson City, NV (US)

( * ) Notice: Subject to any disclaimer, the term of this patent is extended or adjusted under 35 U.S.C. 154(b) by 423 days.

(21) Appl. No.: 15/019,395

(22) Filed: Feb. 9, 2016

(65) Prior Publication Data

US 2016/0297886 A1    Oct. 13, 2016

Related U.S. Application Data

(60) Provisional application No. 62/113,717, filed on Feb. 9, 2015.

(51) Int. Cl.
| C07K 16/00 | (2006.01) |
| C12P 21/08 | (2006.01) |
| C07K 16/28 | (2006.01) |
| C07K 1/00 | (2006.01) |
| A61K 39/00 | (2006.01) |

(52) U.S. Cl.
CPC .......... *C07K 16/2887* (2013.01); *C07K 16/00* (2013.01); *A61K 2039/505* (2013.01); *C07K 2317/41* (2013.01); *C07K 2317/52* (2013.01); *C07K 2317/524* (2013.01); *C07K 2317/72* (2013.01); *C07K 2317/73* (2013.01); *C07K 2317/732* (2013.01); *C07K 2317/734* (2013.01); *C07K 2317/77* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,472,509 A | 9/1984 | Gansow et al. |
| 5,021,236 A | 6/1991 | Gries et al. |
| 5,576,195 A | 11/1996 | Robinson et al. |
| 5,578,464 A | 11/1996 | Lunn et al. |
| 5,595,898 A | 1/1997 | Robinson et al. |
| 5,618,920 A | 4/1997 | Robinson et al. |
| 5,648,260 A | 7/1997 | Winter et al. |
| 5,693,493 A | 12/1997 | Robinson et al. |
| 5,698,417 A | 12/1997 | Robinson et al. |
| 5,698,435 A | 12/1997 | Robinson et al. |
| 5,824,520 A | 10/1998 | Mulligan-Kehoe |
| 5,846,818 A | 12/1998 | Robinson et al. |
| 5,858,657 A | 1/1999 | Winter et al. |
| 5,939,317 A | 8/1999 | Fayard et al. |
| 5,994,514 A | 11/1999 | Jardieu et al. |
| 6,165,745 A | 12/2000 | Ward et al. |
| 6,172,197 B1 | 1/2001 | McCafferty et al. |
| 6,194,551 B1 | 2/2001 | Idusogie et al. |
| 6,204,023 B1 | 3/2001 | Robinson et al. |
| 6,248,516 B1 | 6/2001 | Winter et al. |
| 6,331,415 B1 | 12/2001 | Cabilly et al. |
| 6,455,279 B1 | 9/2002 | Ambrosius et al. |
| 6,500,641 B1 | 12/2002 | Chen et al. |
| 6,528,624 B1 | 3/2003 | Idusogie et al. |
| 6,538,124 B1 | 3/2003 | Idusogie et al. |
| 6,545,142 B1 | 4/2003 | Winter et al. |
| 6,555,313 B1 | 4/2003 | Griffiths et al. |
| 6,667,150 B1 | 12/2003 | Rudert et al. |
| 6,696,248 B1 | 2/2004 | Knappik et al. |
| 6,737,056 B1 | 5/2004 | Presta |
| 6,806,079 B1 | 10/2004 | McCafferty et al. |
| 6,846,653 B2 | 1/2005 | Kolkman |
| 6,979,538 B2 | 12/2005 | Ladner et al. |
| 6,979,556 B2 | 12/2005 | Simmons et al. |
| 6,989,250 B2 | 1/2006 | Soderlind et al. |
| 7,094,571 B2 | 8/2006 | Harvey et al. |
| 7,098,302 B2 | 8/2006 | Krag et al. |
| 7,118,879 B2 | 10/2006 | Ladner et al. |
| 7,183,387 B1 | 2/2007 | Presta |
| 7,202,055 B2 | 4/2007 | Schafer et al. |
| 7,217,798 B2 | 5/2007 | Hinton et al. |
| 7,229,792 B2 | 6/2007 | Pandiripally |
| 7,264,963 B1 | 9/2007 | Knappik et al. |

(Continued)

FOREIGN PATENT DOCUMENTS

| EP | 2679681 | 1/2014 |
| JP | 2007-525443 | 9/2007 |

(Continued)

OTHER PUBLICATIONS

Lee et al., "IgG Fc domains that bind C1q but not effector Fcγ receptors delineate the importance of complement-mediated effector functions," *Nature Immunology*, 18(8):889-898, 2017.

(Continued)

*Primary Examiner* — Chun W Dahle
(74) *Attorney, Agent, or Firm* — Parker Highlander PLLC

(57) ABSTRACT

Methods and compositions involving polypeptides having an aglycosylated antibody Fc domain are provided. In certain embodiments, polypeptides have an aglycosylated Fc domain that contains one or more substitutions compared to a native Fc domain. Additionally, some embodiments involve an Fc domain that is binds some Fc receptors but not others. For example, polypeptides are provided with an aglycosylated Fc domain that selectively binds C1q, and optionally activating Fc receptors, but that is significantly reduced for binding to the inhibitory FcγRIIb receptor. Furthermore, methods and compositions are provided for promoting complement dependent cytotoxicity (CDC) using a polypeptide having a modified aglycosylated Fc domain and a second non-Fc binding domain, which can be an antigen binding region of an antibody or a non-antigen binding region. Some embodiments concern antibodies with such polypeptides, which may have the same or a different non-Fc binding domain.

16 Claims, 40 Drawing Sheets

Specification includes a Sequence Listing.

(56) References Cited

U.S. PATENT DOCUMENTS

| | | |
|---|---|---|
| 7,317,091 B2 | 1/2008 | Lazar et al. |
| 7,371,826 B2 | 5/2008 | Presta |
| 7,662,925 B2 | 2/2010 | Lazar et al. |
| 8,629,245 B2 | 1/2014 | Georgiou et al. |
| 8,679,493 B2 | 3/2014 | Georgiou et al. |
| 8,871,912 B2 | 10/2014 | Davis |
| 8,945,855 B2 | 2/2015 | Iverson et al. |
| 8,952,132 B2 | 2/2015 | Georgiou et al. |
| 9,546,359 B2 | 1/2017 | Georgiou et al. |
| 2003/0158389 A1 | 8/2003 | Idusogie et al. |
| 2003/0166868 A1 | 9/2003 | Presta et al. |
| 2003/0180937 A1 | 9/2003 | Georgiou et al. |
| 2003/0219870 A1 | 11/2003 | Georgiou et al. |
| 2004/0002587 A1 | 1/2004 | Watkins et al. |
| 2004/0132101 A1 | 7/2004 | Lazar et al. |
| 2004/0228856 A1 | 11/2004 | Presta |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0118174 A1 | 6/2005 | Presta |
| 2005/0233382 A1 | 10/2005 | Presta |
| 2005/0244403 A1 | 11/2005 | Lazar et al. |
| 2005/0249723 A1 | 11/2005 | Lazar |
| 2005/0260736 A1 | 11/2005 | Georgiou et al. |
| 2006/0024298 A1 | 2/2006 | Lazar et al. |
| 2006/0121032 A1 | 6/2006 | Dahiyat et al. |
| 2006/0134709 A1 | 6/2006 | Stavenhagen et al. |
| 2006/0153838 A1 | 7/2006 | Watkins et al. |
| 2006/0160996 A9 | 7/2006 | Lazar et al. |
| 2006/0173170 A1 | 8/2006 | Chamberlain et al. |
| 2006/0194290 A1 | 8/2006 | Presta |
| 2006/0194291 A1 | 8/2006 | Presta |
| 2006/0194954 A1 | 8/2006 | Idusogie et al. |
| 2006/0194957 A1 | 8/2006 | Presta |
| 2006/0235208 A1 | 10/2006 | Lazar et al. |
| 2007/0003546 A1 | 1/2007 | Lazar et al. |
| 2007/0036799 A1 | 2/2007 | Stavenhagen et al. |
| 2007/0048300 A1 | 3/2007 | Taylor |
| 2007/0053901 A1 | 3/2007 | Lazar et al. |
| 2008/0292646 A1 | 11/2008 | Benhar et al. |
| 2009/0136936 A1 | 5/2009 | Georgiou et al. |
| 2010/0330076 A1 | 12/2010 | Georgiou et al. |
| 2011/0053803 A1 | 3/2011 | Ge et al. |
| 2011/0059075 A1 | 3/2011 | Wittrup et al. |
| 2013/0058919 A1 | 3/2013 | Lazar et al. |
| 2013/0202606 A1 | 8/2013 | Stavenhagen et al. |
| 2014/0179550 A1 | 6/2014 | Georgiou et al. |
| 2014/0235482 A1 | 8/2014 | Georgiou et al. |
| 2015/0183873 A1 | 7/2015 | Georgiou et al. |
| 2015/0266960 A1 | 9/2015 | Georgiou et al. |
| 2015/0315284 A1 | 11/2015 | Lazar et al. |
| 2016/0366440 A1 | 12/2016 | Hattori |

FOREIGN PATENT DOCUMENTS

| | | | |
|---|---|---|---|
| WO | WO 1998/023646 | 6/1998 | |
| WO | WO-03074679 A2 * | 9/2003 | ............ C07K 16/00 |
| WO | WO 2004/099249 | 11/2004 | |
| WO | WO 2005/037867 | 4/2005 | |
| WO | WO 2006/076594 | 7/2006 | |
| WO | WO 2006/089231 | 8/2006 | |
| WO | WO 2008/114011 | 9/2008 | |
| WO | WO 2008/137475 | 11/2008 | |
| WO | WO 2008/150494 | 12/2008 | |
| WO | WO 2009/079242 | 6/2009 | |
| WO | WO 2011/008517 | 1/2011 | |

OTHER PUBLICATIONS

Andersen et al., "The conserved histidine 166 residue of the human neonatal Fc receptor heavy chain is critical for the pH-dependent binding to albumin," *Eur. J. Immunol.*, 36:3044-3051, 2006.
Baneyx and Mujacic, "Recombinant protein folding and misfolding in *Escherichia coli*," *Nat. Biotechnol.*, 22:1399-1408, 2004.
Better et al., "*Escherichia coli* secretion of an active chimeric antibody fragment," *Science*, 240: 1041-1043, 1988.
Boeke et al., "Effects of bacteriophage f1 gene III protein on the host cell membrane ," *Mol. Gen. Genet.*, 186(2):185-92, 1982.
Bolland and Ravetch, "Inhibitory pathways triggered by ITIM-containing receptors," *Adv. Immunol.*, 72:149-177, 1999.
Borrok et al., "Revisiting the role of glycosylation in the structure of human IgG Fc," *ACS Chem. Biol.*, 7:1596-1602, 2012.
Boruchov et al., "Activating and inhibitory IgG Fc receptors on human DCs mediate opposing functions," *The Journal of Clinical Investigation*, 115(10):2914-2923, 2005.
Boss et al., "Assembly of functional antibodies from immunoglobulin heavy and light chains synthesised in *E. coli*," *Nucleic Acids Res.*, 12:3791-3806, 1984.
Bowden and Georgiou, "Folding and aggregation of beta-lactamase in the periplasmic space of *Escherichia coli*," *J. Biol. Chem.*, 265:16760-16766, 1990.
Bukau et al., "Ca2+-induced permeabilization of the *Escherichia coli* outer membrane: comparison of transformation and reconstitution of binding-protein-dependent transport," *J. Bacteriol.*, 163:61, 1985.
Cabilly et al., "Generation of antibody activity from immunoglobulin polypeptide chains produced in *Escherichia coli*," *Proc. Natl. Acad. Sci USA*, 81:3273-3277, 1984.
Canfield et al., "The binding affinity ofh uman IGG for its high affinity FC receptor is determined by multiple amino acids in the C—H2 domain and is modulated by the hinge region," *Journal of Experimental Medicine*, 173(6): 1483-1492, 1991.
Daeron, "Fc receptor biology," *Annu. Rev. Immunol.*, 15:203-234, 1997.
Dall'Acqua et al., "Modulation of the effector functions of a human IgG1 through engineering of its hinge region," *J. Immunol.*, 177:1129-1138, 2006.
Dall'Acqua et al., "Properties of human IgG1s engineered for enhanced binding to the neonatal Fc receptor (FcRn)," *J. Biol. Chem.*, 281(33):23514-23524, 2006.
Daughtery et al., "Development of an optimized expression system for the screening of antibody libraries displayed on the *Escherichia coli* surface," *Protein Eng.*, 12:613-621, 1999.
De Kruif and Logtenberg, "Leucine zipper dimerized bivalent and bispecific scFv antibodies from a semi-synthetic antibody phage display library," *J. Biol. Chem.*, 271:7630-7634, 1996.
Desai et al., "Characterization of human anti-high molecular weight-melanoma-associated antigen single-chain Fv fragments isolated from a phage display antibody library," *Cancer Res.*, 58:2417-2425, 1998.
Diebolder et al., Complement is activated by IgG hexamers assembled at the cell surface, *Science*, 343:1260-1263, 2014.
Eigenbrot et al., "X-ray structures of the antigen-binding domains from three variants of humanized anti-p185HER2 antibody 4D5 and comparison with molecular modeling," *J. Molec. Biol.*, 229:969-995, 1993.
Elbein et al., "New insights on trehalose: a multifunctional molecule," *Glycobiology*, 13:17R-27R, 2003.
Extended European Search Report issued in European Application No. 10800284.1, dated Oct. 25, 2012.
Farmer et al, "Penetration of beta-lactamase inhibitors into the periplasm of gram-negative bacteria," *FEMS Microbiol. Lett.*, 176:11, 1999.
Francisco et al., "Production and fluorescence-activated cell sorting of *Escherichia coli* expressing a functional antibody fragment on the external surface," *Proc. Natl. Acad. Sci. USA*, 90:10444-10448, 1993.
Friend et al., "Phase I study of an engineered aglycosylated humanized CD3 antibody in renal transplant rejection," *Transplantation*, 68(110): 132-1637, 1999.
Gaboriaud et al., "The crystal structure of the globular head of complement protein C1q provides a basis for its versatile recognition properties," *J. Biol. Chem.*, 278:46974-46982, 2003.
Garinot-Schneider et al., "Identification of putative active-site residues in the DNase domain of colicin E9 by random mutagenesis," *J. Mol. Biol.*, 260:731-742, 1996.

(56) References Cited

OTHER PUBLICATIONS

Georgiou and Segatori, "Preparative expression of secreted proteins in bacteria: status report and future prospects," *Current Opin. Biotech.*, 16:538-545, 2005.
Ghetie and Ward, "Multiple roles for the major histocompatibility complex class I-related receptor FcRn," *Annu. Rev. Immunol.*, 18:739-766, 2000.
Greenspan et al., "Defining epitopes: It's not as easy as it seems," *Nature Biotechnology*, 17:936-937, 1999.
Griffiths and Duncan, "Strategies for selection of antibodies by phage display," *Curr. Opin. Biotechnol.*, 9:102-108, 1998.
Guddat et al., "Three-dimensional structure of a human immunoglobulin with a hinge deletion," *Proc. Natl. Acad. Sci. USA*, 90:4271-4275, 1993.
Guzman et al., "Tight regulation, modulation, and high-level expression by vectors containing the arabinose PBAD promoter," *J. Bacteriol.*, 177:4121-4130, 1995.
Harvey et al., "Anchored periplasmic expression, a versatile technology for the isolation of high-affinity antibodies from *Escherichia coli*-expressed libraries," *Proc. Natl. Acad. Sci. USA*, 101:9193-9198, 2004.
Harvey et al., "Engineering of recombinant antibody fragments to methamphetamine by anchored periplasmic expression," *J. Immunol. Methods*, 308:43-52, 2006.
Herr et al., "Insights into IgA-mediated immune responses from the crystal structures of human FcαRI and its complex with IgA1-Fc", *Nature*, 423 (6940): 614-620, 2003.
Hoogenboom and Winter, "By-passing immunisation. Human antibodies from synthetic repertoires of germline VH gene segments rearranged in vitro," *J. Mol. Biol.*, 227(2):381-388, 1992.
Hoogenboom et al., "Antibody phage display technology and its applications," *Immunotechnology*, 4:1-20, 1998.
Hoover and Lubkowski, "DNAWorks: an automated method for designing oligonucleotides for PCR-based gene synthesis," *Nucl. Acids Res.*, 30:e43, 2002.
Huang, "Receptor-Fc fusion therapeutics, traps, and MIMETIBODY technology", *Current Opinion in Biotechnology*, 20:692-699, 2009.
Hudis, "Trastuzumab—Mechanism of Action and Use in Clinical Practice," *N. Engl. J. Med.*, 357:39-51, 2007.
Idusogie et al., "Engineered antibodies with increased activity to recruit complement," *J. Immunol.*, 166:2571-2575, 2001.
Irvin et al., "Tris(hydroxymethyl)aminomethane buffer modification of *Escherichia coli* outer membrane permeability," *J. Bacteriol.*, 145:1397, 1981.
Jefferis et al., "Recognition sites on human IgG for Fc-gamma receptors: The role of glycosylation," *Immunology Letters*, 44(2-3):111-117, 1995.
Jefferis, "Glycosylation of recombinant antibody therapeutics," *Biotechnol. Prog.*, 21:11-16, 2005.
Jeong and Lee, "Enhanced production of recombinant proteins in *Escherichia coli* by filamentation suppression," *Appl. Environ. Microbiol.*, 69:1295-1298, 2003.
Jouenne and Junter, "Do beta-lactam antibiotics permeabilize the outer membrane of gram-negative bacteria? An electrochemical investigation," FEMS Microbiol. Lett., 68(3):313-318, 1990.
Jung et al., "Aglycosylated IgG variants expressed in bacteria that selectively bind FcγRI potentiate tumor cell killing by monocyte-dendritic cells," *PNAS*, 107(2):604-609, 2010.
Jung et al., "Effective phagocytosis of low Her2 tumor cell lines with engineered, aglycosylated IgG displaying high Fc(gamma)RIIa affinity and selectivity," *ACS Chemical Bioloy*, 8(2):368-375, 2013.
Jung et al., "Efficient expression and purification of human aglycosylated Fc gamma receptors in *Escherichia coli,"* *Biotechnology and Bioengineering*, 107(1):21-30, 2010.
Jung et al., "Engineering an aglycosylated Fc variant for enhanced Fc(gamma) R1 engagement and pH-dependent human FcRn binding," *Biotechnology and Bioprocess Engineering*, 19(5):780-789, 2014.

Jung et al., "Purification of enzymatically active human lysyl oxidase and lysy oxidase-like protein from *Escherichia coli* inclusion bodies," *Protein Expr. Purif.*, 31:240-246, 2003.
Kabat et al., In: *Sequences of Proteins of Immunological Interest*, U.S. Dept. Health and Hum. Serv., Bethesda, Md., 1991.
Kalergis, "Inducing tumor immunity through the selective engagement of activating Fcγ receptors on dendritic cells," *J. Exp. Med.*, 195(12):1653-1659, 2002.
Kawarasaki et al., "Enhanced crossover SCRATCHY: construction and high-throughput screening of a combinatorial lilbrary containing multiple non-homologous crossovers," *Nucleic Acids Res.*, 31:e126, 2003.
Kipriyanov and Little, "Generation of recombinant antibodies," *Mol. Biotechnol.*, 12:173-201, 1999.
Kjaer et al., "Glycerol diversifies phage repertoire selections and lowers non-specific phage absorption,"*FEBS Lett.*, 431(3):448-452, 1998.
Knight et al., "The immunogenicity of the 7E3 murine monoclonal Fab antibody fragment variable region is dramatically reduced in humans by substitution of human for murine constant regions," *Mol. Immunol.*, 32:1271-1281, 1995.
Kohler and Milstein, "Continuous cultures of fused cells secreting antibody of predefined specificity," *Nature*, 256:495-497, 1975.
Kouzarides and Ziff, "The role of the leucine zipper in the fos-jun interaction," *Nature*, 336:646-6451, 1988.
Landschulz et al., "The leucine zipper: a hypothetical structure common to a new class of DNA binding proteins," *Science*, 240:1759-1764, 1988.
Lazar et al., "Engineered antibody Fc variants with enhanced effector function," *Proc. Natl. Acad. Sci. USA*, 103:4005-4010, 2006.
Lei et al., "Characterization of the Erwinia carotovora pelB gene and its product pectate lyase," *J. Bacteriol.*, 169:4379-4383, 1987.
Marciano et al., "An aqueous channel for filamentous phage export," *Science*, 284:1516-1519, 1999.
Mazor et al., "Isolation of engineered, full-length antibodies from libraries expressed in *Escherichia coli,"* *Nat. Biotech.*, 25:563-5, 2007.
Mimoto et al., "Engineered antibody Fc variant with selectively enhanced Fc RIIb binding over both Fc RIIaR131 and Fc RIIaH131," *Protein Engineering Design and Selection*, 26(10):589-598, 2013.
Moore et al., "Engineered Fc variant antibodies with enhanced ability to recruit complement and mediate effector functions," *mAbs*, 2:181-189, 2010.
Munson and Robard, "Ligand: a versatile computerized approach for characterization of ligand-binding systems," *Anal. Biochem.*, 107:220-239, 1980.
Natsume et al., "Engineered antibodies of IgG1/IgG3 mixed isotype with enhanced cytotoxic activities," *Cancer Res.*, 68:3863-3872, 2008.
Nikaido, "Multidrug efflux pumps of gram-negative bacteria," *J. Bacteriology*, 178(20):5853-5859, 1996.
O'Brien et al., "Bacterial expression and purification of recombinant bovine Fab fragments," *Protein Expr. Purif.*, 24:43-50, 2002.
Office Action issued in Australian Application No. 2008247819, dated May 16, 2012.
Office Action issued in Australian Application No. 2008247819, dated Jul. 19, 2012.
Office Action issued in Australian Application No. 2010273763, dated Oct. 24, 2013.
Office Action issued in Chinese Application No. 201080038758.4, dated Apr. 2, 2014.
Office Action issued in Chinese Application No. 201080038758.4, dated Jul. 16, 2013.
Office Action issued in European Application No. 08747239.5, dated Jul. 21, 2011.
Office Action issued in European Application No. 08747239.5, dated May 16, 2011.
Office Action issued in European Application No. 08747239.5, dated Oct. 21, 2011.
Office Action issued in European Application No. 08747239.5, dated Mar. 19, 2012.

(56) References Cited

OTHER PUBLICATIONS

Office Action issued in European Application No. 08747239.5, dated Sep. 3, 2012.
Office Action issued in Japanese Application No. 2013-553476, dated Oct. 15, 2015, and English language translation thereof.
Office Action issued in U.S. Appl. No. 12/112,971, dated Jul. 20, 2012.
Office Action issued in U.S. Appl. No. 12/112,971, dated May 20, 2013.
Office Action issued in U.S. Appl. No. 12/112,971, dated May 26, 2011.
Office Action issued in U.S. Appl. No. 12/112,971, dated Nov. 9, 2010.
Office Action issued in U.S. Appl. No. 12/112,971, dated Nov. 29, 2012.
Office Action issued in U.S. Appl. No. 12/827,386, dated Aug. 15, 2013.
Office Action issued in U.S. Appl. No. 12/827,386, dated Mar. 4, 2013.
Office Action issued in U.S. Appl. No. 12/827,386, dated Sep. 26, 2012.
Office Action issued in U.S. Appl. No. 13/367,063, dated Jun. 19, 2013.
Office Action issued in U.S. Appl. No. 13/367,063, dated Mar. 20, 2013.
Office Action issued in U.S. Appl. No. 13/367,063, dated Nov. 8, 2013.
Office Action issued in U.S. Appl. No. 14/105,642, dated Aug. 12, 2016.
Office Action issued in U.S. Appl. No. 14/105,642, dated Dec. 30, 2016.
Office Action issued in U.S. Appl. No. 14/105,642, dated Mar. 24, 2016.
Office Action issued in U.S. Appl. No. 14/181,594, dated Dec. 17, 2015.
Office Action issued in U.S. Appl. No. 14/181,594, dated Jul. 2, 2015.
Office Action issued in U.S. Appl. No. 14/437,544, dated Nov. 3, 2016.
Orlandi et al., "Cloning immunoglobulin variable domains for expression by the polymerase chain reaction," *Proc. Natl. Acad. Sci. USA*, 86:3833-3837, 1989.
Osborn et al., "Mechanism of assembly of the outer membrane of *Salmonella typhimurium*. Site of synthesis of lipopolysaccharide," *J. Biol. Chem*, 247:3973-3986, 1972.
Painbeni et al., "Alterations of the outer membrane composition in *Escherichia coli* lacking the histone-like protein HU," *Proc. Natl. Acad. Sci. USA*, 94:6712, 1997.
PCT International Preliminary Report on Patentability issued in International Application No. PCT/US2008/062090, dated May 8, 2009.
PCT International Preliminary Report on Patentability issued in International Application No. PCT/US2012/023949, dated May 9, 2013.
PCT International Preliminary Report on Patentability issued in International Application No. PCT/US2010/04304, dated Jan. 12, 2012.
PCT International Preliminary Report on Patentability issued in International Application No. PCT/US2013/057605, dated May 7, 2015.
PCT International Search Report and Written Opinion issued in International Application No. PCT/US2016/017100, dated Jul. 26, 2016.
PCT International Search Report and Written Opinion issued in International application No. PCT/US2010/04304, dated May 30, 2011.
PCT International Search Report and Written Opinion issued in International Application No. PCT/US2016/048214, dated Mar. 1, 2017.
PCT International Search Report and Written Opinion issued in International application No. PCT/US2012/023949, dated May 10, 2012.
PCT International Search Report and Written Opinion issued in International Application No. PCT/US2013/057605, dated Nov. 28, 2013.
PCT International Search Report and Written Opinion issued in International Application No. PCT/US2008/062090, dated Nov. 24, 2008.
Pleass et al., "Identification of residues in the CH2/CH3 domain interface of IgA essential for interaction with the human Fcα receptor (FcαR) CD89*", *Journal of Biological Chemistry*, 274(33): 23508-23514, 1999.
Purvis et al., "Enhanced trehalose production improves growth of *Escherichia coli* under osmotic stress," *Appl. Environ. Microbiol.*, 71:3761-3769, 2005.
Rao and Torriani, "Utilization by *Escherichia coli* of a high-molecular-weight, linear polyphosphate: Roles of phosphates and pore proteins," *J. Bacteriol.*, 170, 5216-5223, 1988.
Ravetch and Perussia et al., "Alternative membrane forms of Fc gamma RIII(CD16) on human natural killer cells and neutrophils. Cell type-specific expression of two genes that differ in single nucleotide substitutions," *J. Exp. Med.*, 170:481-497, 1989.
Ravetch et al., "Structural heterogeneity and functional domains of murine immunoglobulin G Fc receptors," *Science*, 234:718-725, 1986.
Richards et al., "Optimization of antibody binding to FcrRγRIIa enhances macrophage phagocytosis of tumor cells," *Mol. Cancer Ther.*, 7:2517-2527, 2008.
Rogers et al., Complement in monoclonal antibody therapy of cancer. Immunol. Res. 59:203-10, 2014.
Sazinsky et al., "Aglycosylated immunoglobulin G1 variants productively engage activating Fc receptors," *Proc. Natl. Acad. Sci. USA*, 105:20167-20172, 2008.
Schierle et al., "The DsbA signal sequence directs efficient, cotranslational export of passenger proteins to the *Escherichia coli* periplasm via the signal recognition particle pathway," *J. Bacteriol.*, 185:5706-5713, 2003.
Sergina, and Moasser, "The HER family and cancer: emerging molecular mechanisms and therapeutic targets," *Trends in Molec. Med.*, 13:527-534, 2007.
Simmons et al., "Expression of full-length immunoglobulins in *Escherichia coli*: rapid and efficient production of aglycosylated antibodies," *Journal of Immunological Methods*, 263(1-2): 133-147, 2002.
Sondermann et al., "Molecular basis for immune complex recognition: a comparison of Fc-receptor structures," *J. Mol. Biol.*, 309:737-749, 2001.
Stengelin et al., "Isolation of cDNAs for two distinct human Fc receptors by ligand affinity cloning," *Embo J*, 7:1053-1059, 1988.
Van Egmond et al., "Enhancement of Polymorphonuclear Cell-mediated Tumor Cell Killing on Simultaneous Engagement of FcγRI (CD64) and FcαRI (CD89)", Cancer Research, 61(10): 4055, 2001.
Wada et al., "A novel labeling approach supports the five-transmembrane model of subunit a of the *Escherichia coli* ATP synthase," *J. Biol. Chem.*, 274:17353-17357, 1999.
Walport, "Complement. First of two parts," *N. Engl. J. Med.*, 344:1058-1066, 2001.
Walport, "Complement. Second of two parts," *N. Engl. J. Med.*, 344:1140-1144, 2001.
Woof and Burton, "Human antibody-Fc receptor interactions illuminated by crystal structures," *Nat. Rev. Immunol.* 4:89-99, 2004.
Woof et al., "Localisation of the monocyte-binding region on human immunoglobulin G," *Molecular Immunology*, 23(3): 319-330, 1986.
Woof et al., "Structure and function relationships in IgA", Mucosal Immunology, 4(6): 590-597, 2011.
Woof et al., "The IgA-Fcα receptor interaction and its blockade by streptococcal IgA-binding proteins", *Biochemical Society Transactions*, 30: 491-494, 2002.
Wright and Morrison, "Effect of glycosylation on antibody function: implications for genetic engineering," *Trends Biotech.*, 15:26-32, 1997.

(56) References Cited

OTHER PUBLICATIONS

Monnet et al., "Selection of IgG variants with increased FcRn binding using random and directed mutagenesis: impact on effector functions," *Frontiers in Immunology,* 6(39):1-14, 2015.
Office Action issued in European Application No. 16706710.7, dated Oct. 17, 2018.

* cited by examiner pBAD30-PelB-VL-Ck-NlpA-VL-Ck-His-cMyc pMopac12-pelB-IgG-VH-CH1-CH2-CH3-FLAG

ENGINEERED IMMUNOGLOBULIN FC POLYPEPTIDES DISPLAYING IMPROVED COMPLEMENT ACTIVATION

The present application claims the priority benefit of U.S. provisional application No. 62/113,717, filed Feb. 9, 2015, the entire contents of which is incorporated herein by reference.

BACKGROUND OF THE INVENTION

1. Field of the Invention

The present invention relates generally to the field of protein engineering. More particularly, it concerns compositions comprising Fc antibody domains conferring increased binding to C1q relative to wild-type Fc antibody domains.

2. Description of Related Art

Currently, the top 25 marketed recombinant therapeutic antibodies have sales of well over $43.5 billion/year, and with a forecasted annual growth rate of 9.2% from 2010 to 2015, they are projected to increase to $62.7 billion/year by 2015 (Elvin et al., 2013). Monoclonal antibodies (mAbs) comprise the majority of recombinant proteins currently in the clinic, with 1064 products undergoing company-sponsored clinical trials in the USA or EU, of which 164 are phase III (Elvin et al., 2013). In terms of therapeutic focus, the mAb market is heavily focused on oncology, arthritis, and immune and inflammatory disorders, and products within these therapeutic areas are set to continue to be the key growth drivers over the forecast period. As a group, genetically engineered mAbs generally have a higher probability of FDA approval success than small-molecule drugs. At least 50 biotechnology companies and all major pharmaceutical companies have active antibody discovery programs in place. The original method for isolation and production of mAbs was first reported at 1975 by Milstein and Kohler (Kohler and Milstein, 1975), and it involved the fusion of mouse lymphocyte and myeloma cells, yielding mouse hybridomas. Therapeutic murine mAbs entered clinical study in the early 1980s; however, problems with lack of efficacy and rapid clearance due to patients' production of human anti-mouse antibodies (HAMA) became apparent. These issues, as well as the time and cost consumption related to the technology, became driving forces for the evolution of mAb production technology. Polymerase Chain Reaction (PCR) facilitated the cloning of monoclonal antibody genes directly from lymphocytes of immunized animals and the expression of combinatorial libraries of antibody fragments in bacteria (Orlandi et al., 1989). Later libraries were created entirely by in vitro cloning techniques using naive genes with rearranged complementarity determining region 3 (CDR3) (Griffths and Duncan, 1998; Hoogenboom et al., 1998). As a result, the isolation of antibody fragments with the desired specificity was no longer dependent on the immunogenicity of the corresponding antigen. Moreover, the range of antigen specificities in synthetic combinatorial libraries was greater than that found in a panel of hybridomas generated from an immunized mouse. These advantages have facilitated the development of antibody fragments to a number of unique antigens including small molecular compounds (haptens) (Hoogenboom and Winter, 1992), molecular complexes (Chames et al., 2000), unstable compounds (Kjaer et al., 1998), and cell surface proteins (Desai et al., 1998). In microbial cells, display screening may be carried out by flow cytometry. In particular, Anchored Periplasmic Expression (APEx) is based on anchoring the antibody fragment on the periplasmic face of the inner membrane of E. coli followed by disruption of the outer membrane, incubation with fluorescently-labeled target, and sorting of the spheroplasts (U.S. Pat. No. 7,094,571). APEx was used for the affinity maturation of antibody fragments (Harvey et al., 2004; Harvey et al., 2006). In one study, over 200-fold affinity improvement was obtained after only two rounds of screening.

One important mechanism underlying the potency of antibody therapeutics is Fc-mediated effector functions for clearance of a target antigen (or cell) via two processes. The Fc domain binds to a number of proteins including soluble proteins in serum and receptors on cell surfaces. Binding of the Fc region of antibodies that have formed immune complexes with a pathogenic target cell to the complement protein C1q, result in the activation of the classical complement activation cascade (Walport, 2001; Janeway et al., 2005). Separately, the Fc domain binds to different receptors expressed on the surface of leukocytes to elicit antibody-dependent cell cytotoxicity (ADCC) and antibody-dependent cell phagocytosis (ADCP).

In particular, activation of the classical pathway following the formation of a complex between C1q and antibodies bound to pathogen elicits a cascade of biochemical reaction that lead to pathogen elimination via several mechanisms. First, formation of the membrane attack complex (MAC) on the surface of the cell, which kills cells by comprising the integrity of the cell membrane. Second, opsonization due to the deposition of complement proteins onto the surface of the pathogen and recognition of the complement opsonins by complement receptors on leukocytes triggers complement dependent cell cytotoxicity (CDCC). A single molecule of IgG can not activate the complement pathway because of the low affinity of IgG for C1q and because the requirement that C1q binds to multiple IgG molecules in the proper spatial orientation (i.e., as an immune complex) in order to initiate conformational changes necessary for the activation of the so called "classical" complement pathway (Walport, 2001; Janeway et al., 2005).

In humans there are two general classes of FcγRs that bind to the Fc domain of IgG subclass antibodies: activating receptors, characterized by the presence of a cytoplasmic immunoreceptor tyrosine-based activation motif (ITAM) sequence, and the inhibitory receptor, characterized by the presence of an immunoreceptor tyrosine-based inhibitory motif (ITIM) sequence (Daeron, 1997; Bolland et al., 1999). Of note, activating FcγRs (i.e., FcγRI, FcγRIIA, FcγRIIIA, and FcγRIIIB) induce activating or pro-inflammatory responses, while the inhibitory receptor (i.e., FcγRIIB) induces anti-inflammatory responses. The ability of antibodies to induce activating ADCC depends on the ratio of binding affinities to the activating FcγRs vs. the inhibitory FcγRIIB (A/I ratio) (Boruchov et al. 2005; Kalergis et al., 2002). A number of allotypes of the FcγRs are known. For example, the FcγRIIA$_{H131}$ allotype shows higher binding affinity for IgG than the FcγRIIA$_{R131}$ allotype, while the FcγRIIIA$_{V158}$ allotype shows higher binding affinity than FcγRIIIA$_{F158}$IgG1 Fc domains, which bind to both the activating and the inhibitory FcγRs as well as to C1q. In contrast, human IgG2 isotype antibodies bind weakly to C1q (and thus are very poor in mediating complement activation and show little or no binding to FcγRs). Human IgG3 and IgG4 isotype antibodies display respectively higher and no C1q binding relative to IgG1 and generally weaker affinity to FcγRs.

The C1q and FcγR binding sites on IgG1 have been identified based on, docking models of IgG1 with C1q and crystal structures of the Fc domain with the extracellular domains of the FcγRs. Both C1q and FcγRs interact primarily with amino acids located in the Fc CH2 domain and in some instances the hinge of IgG1 antibodies. For C1q, Asp270, Lys322, and Pro329-Pro331 are particularly important for binding, as is the orientation of the Fab arms (Gaboriaud et al., 2003; Guddat et al., 1993) In terms of FcγR binding, Leu234-Ser239 in the IgG lower hinge region and Asp265-Ser267 in the CH2 domain are particularly important (Gaboriaud et al., 2003; Woof et al., 2004). The CH2 domain has one N-glycosylation site at Apn297, and the N-linked glycan at Asn297 bridges the gap between the two CH2 domains. This bridge maintains the proper conformation of CH2 domains for binding to C1q and FcγRs. On the other hand, the removal of the glycan at Asn297 increases the conformational flexibility of the CH2 domains, and as a result, aglycosylated Fc show essentially no binding to C1q and to FcγRs, thus abolishing ADCC and CDC (Borrok et al., 2012).

Antibody mediated complement activation and CDC are of particular importance in the function of numerous therapeutic antibodies (Rogers et al., 2014). Therefore strategies to increase complement activation have received considerable attention. For example, chimeric IgG molecules comprising IgG1 and IgG3 (Natsume et al., 2008) were reported to display enhanced C1q binding without affecting FcγRs-binding ability resulting in enhanced CDC activity towards CD20+ lymphoma cell lines. Dall'Acqua et al. (2006) reported that amino acid substitution in the hinge region of human IgG1 resulted in slightly decreased CDC activity and lower ADCC activities compared to wild-type IgG. In another study, a K326W/E333S double mutation in the IgG1 Fc domain resulted in a 5-fold increase in binding to C1q and 2-fold increase in CDC (Idusogie et al., 2001). More recently Moore et al. (2010) reported that a S267E/H268F/S324T triple mutant in the IgG1 Fc domain showed 47-fold-enhanced affinity to C1q and 6.9-fold-enhanced $EC_{50}$ values in CDC. The S267E/H268F/S324T triple mutant also showed increased affinity towards some but not all of the human FcγRs (Moore et al., 2010). Finally, Diebolder et al. (2014) reported that mutations in the Fc domain that favor the formation of IgG hexamers, most notably an E345R substitution, showed 12-fold enhanced CDC efficacy towards CD20+ positive Daudi cells. However, the effects of hexamer formation on FcγR binding or ADCC has not been reported.

E. coli possesses a reducing cytoplasm that is unsuitable for the folding of proteins with disulfide bonds, which accumulate in an unfolded or incorrectly folded state (Baneyx and Mujacic, 2004). In contrast to the cytoplasm, the periplasm of E. coli is maintained in an oxidized state that allows the formation of protein disulfide bonds. Notably, periplasmic expression has been employed successfully for the expression of antibody fragments, such as Fvs, scFvs, Fabs, or F(ab')2s (Kipriyanov and Little, 1999). These fragments can be made relatively quickly in large quantities with the retention of antigen binding activity. However, because antibody fragments lack the Fc domain, they do not bind the FcRn receptor and are cleared quickly; thus, they are only occasionally suitable as therapeutic proteins (Knight et al., 1995). Until recently, full-length antibodies could only be expressed in E. coli as insoluble aggregates and then refolded in vitro (Boss et al., 1984; Cabilly et al., 1984). Clearly this approach is not amenable to the high-throughput screening of antibody libraries since with the current technology it is not possible to refold millions or tens of millions of antibodies individually. A further problem is that since E. coli expressed antibodies are not glycosylated, they fail to bind to complement factor 1q (C1q) or Fc and other Fcγ receptors with the exception of the neonatal Fc receptor (FcRn), which is critical for the long persistence of IgG antibodies in circulation.

SUMMARY OF THE INVENTION

This disclosure provides compounds and methods involving aglycosylated antibody Fc domains that display increased affinity for C1q and/or selectivity for C1q only or selectivity for binding to C1q and activating Fc receptors but not FcγRIIB In some embodiments, there are provided compositions comprising a polypeptide that has a variant aglycosylated Fc domain from a human IgG1 antibody ("antibody Fc domain"). In additional embodiments, the aglycosylated Fc domain is a variant of the human IgG1 Fc domain (SEQ ID NO: 1; position 1 of SEQ ID NO: 1 corresponds to position 231 of the EU index as in Kabat) that enables highly selective binding only to C1q and not to any of the effector Fc receptors, namely FcγRI, FcγRIIA, FcγRIIIA, and FcγRIIIB In other embodiments, an engineered variant Fc domain may bind highly selectively to C1q and displays little or no binding to effector Fc receptors, both when it is expressed in aglycosylated form and when it is expressed in glycosylated form. Yet in further embodiments, antibodies comprising variant Fc domains are provided that display increased affinity to C1q relative to SEQ ID NO: 1 (wild-type human Fc domain) and also to activating, pro-inflammatory Fc receptors but not to the inhibitory receptor FcγRIIB Relative binding capabilities between polypeptides having a mutated and aglycosylated Fc domain and polypeptides having a glycosylated and wild-type Fc domain may be expressed in terms of fold differences (increased or decreased). In an additional embodiment, engineered variant Fc domains display increased affinity for C1q between within 10- to 250-fold of a polypeptide having a glycosylated wild-type Fc domain, more preferably between within 150- to 250-fold.

In some embodiments, there is provided a polypeptide comprising an aglycosylated variant human Fc domain that comprises particular amino acid substitutions. In some embodiments there are multiple amino acid substitutions. In some aspects, a variant human IgG Fc domain capable of binding only to C1q and not to any Fc receptor may comprise substitutions at amino acids 320 and 386. In some aspects, a variant human IgG Fc domain capable of binding only to C1q and not to any Fc receptor may comprise substitutions at amino acids 235, 236, 237 and 351. In some aspects, a variant human IgG Fc domain capable of binding C1q and activating Fcγ receptors, but not FcγRIIB, may comprise substitutions at amino acids 308, 337, 338, 340, 342, 344, 345 and 372. The number of the residues in the Fc domain is that of the EU index as in Kabat.

In some aspects, when the variant Fc domain comprises amino acid substitutions at amino acids 320 and 386, the substitution at amino acid 320 is glutamate (K320E) and the substitution at amino acid 386 is arginine (Q386R). In certain aspects, the aglycosylated variant human IgG Fc domain may be Fc801 (SEQ ID NO: 7).

In some aspects, when the variant Fc domain comprises amino acid substitutions at amino acids 235, 236, 237 and 351, the substitution at amino acid 235 is lysine (L235K), the substitution at amino acid 236 is methionine (G236M), the substitution at amino acid 237 is arginine (G237R), and the substitution at amino acid 351 is glutamine (L351Q). In certain aspects, the aglycosylated variant human IgG Fc domain may be Fc802 (SEQ ID NO: 10).

In some aspects, when the variant Fc domain comprises amino acid substitutions at amino acids 308, 337, 338, 340, 342, 344, 345 and 372, the substitution at amino acid 308 is alanine (V308A), the substitution at amino acid 337 is proline (S337P), the substitution at amino acid 338 is glutamine (K338Q), the substitution at amino acid 340 is arginine (K340R), the substitution at amino acid 342 is proline (Q342P), the substitution at amino acid 344 is glycine (R344G), the substitution at amino acid 345 is tyrosine (E345Y) and the substitution at amino acid 372 is leucine (F372L). In certain aspects, the aglycosylated variant human IgG Fc domain may be Fc805 (SEQ ID NO: 22).

In some aspects, when the variant Fc domain comprises an amino acid substitution at amino acid 252, the substitution at amino acid 252 is valine (M252V). In certain aspects, the aglycosylated variant human IgG Fc domain may be Fc-V1 (SEQ ID NO: 36).

In some aspects, when the variant Fc domain comprises amino acid substitutions at amino acids 246, 322, and 402, the substitution at amino acid 246 is asparagine (K246N), the substitution at amino acid 322 is glutamic acid (K322E), and the substitution at amino acid 402 is aspartic acid (G402D). In certain aspects, the aglycosylated variant human IgG Fc domain may be Fc-V11 (SEQ ID NO: 37).

In some aspects, when the variant Fc domain comprises amino acid substitutions at amino acids 320 and 386, the substitution at amino acid 320 is glutamate (K320E) and the substitution at amino acid 386 is arginine (Q386R). In certain aspects, the aglycosylated variant human IgG Fc domain may be Fc801 (SEQ ID NO: 7).

In some aspects, when the variant Fc domain comprises amino acid substitutions at amino acids 242, 315, 336, 340, 342, 378 and 386, the substitution at amino acid 242 is leucine (F242L), the substitution at amino acid 315 is serine (N315S), the substitution at amino acid 336 is methionine (I336M), the substitution at amino acid 340 is arginine (K340R), the substitution at amino acid 342 is aspartic acid (Q342D), the substitution at amino acid 378 is threonine (A378T), and the substitution at amino acid 386 is arginine (Q386R). In certain aspects, the aglycosylated variant human IgG Fc domain may be Fc-V12 (SEQ ID NO: 38).

In some aspects, when the variant Fc domain comprises amino acid substitutions at amino acids 334, 351, and 421, the substitution at amino acid 334 is glutamate (K334E), the substitution at amino acid 351 is glutamine (L351Q), and the substitution at amino acid 421 is aspartic acid (N421D). In certain aspects, the aglycosylated variant human IgG Fc domain may be Fc-V15 (SEQ ID NO: 39).

In some aspects, when the variant Fc domain comprises amino acid substitutions at amino acids 341 and 351, the substitution at amino acid 341 is alanine (G341A) and the substitution at amino acid 351 is glutamine (L351Q). In certain aspects, the aglycosylated variant human IgG Fc domain may be Fc-V17 (SEQ ID NO: 40).

In some aspects, when the variant Fc domain comprises amino acid substitutions at amino acids 252, 341, and 351, the substitution at amino acid 252 is valine (M252V), the substitution at amino acid 341 is alanine (G341A), and the substitution at amino acid 351 is glutamine (L351Q). In certain aspects, the aglycosylated variant human IgG Fc domain may be Fc-V18 (SEQ ID NO: 41).

In some aspects, when the variant Fc domain comprises amino acid substitutions at amino acids 246, 260, 315, and 386, the substitution at amino acid 246 is glutamine (K246Q), the substitution at amino acid 260 is alanine (T260A), the substitution at amino acid 315 is serine (N315S), and the substitution at amino acid 386 is arginine (Q386R). In certain aspects, the aglycosylated variant human IgG Fc domain may be Fc-V19 (SEQ ID NO: 42).

In some aspects, when the variant Fc domain comprises amino acid substitutions at amino acids 246, 252, 322, 344, 345, and 372, the substitution at amino acid 246 is asparagine (K246N), the substitution at amino acid 252 is valine (M252V), the substitution at amino acid 322 is glutamic acid (K322E), the substitution at amino acid 344 is glycine (R344G), the substitution at amino acid 345 is tyrosine (E345Y), and the substitution at amino acid 372 is leucine (F372L). In certain aspects, the aglycosylated variant human IgG Fc domain may be Fc-V23 (SEQ ID NO: 43).

In some aspects, when the variant Fc domain comprises amino acid substitutions at amino acids 242, 252, 338, 341, and 345, the substitution at amino acid 242 is leucine (F242L), the substitution at amino acid 252 at valine (M252V), the substitution at amino acid 338 is glutamine (K338Q), the substitution at amino acid 341 is alanine (G341A), and the substitution at amino acid 345 is tyrosine (E345Y). In certain aspects, the aglycosylated variant human IgG Fc domain may be Fc-V24 (SEQ ID NO: 44).

In some aspects, when the variant Fc domain comprises amino acid substitutions at amino acids 334, 402, 338, 342, 344, 345, and 372, the substitution at amino acid 334 is glutamic acid (K334E), the substitution at amino acid 402 is aspartic acid (G402D), the substitution at amino acid 338 is glutamine (K338Q), the substitution at amino acid 342 is proline (Q342P), the substitution at amino acid 344 is glycine (R344G), the substitution at amino acid 345 is tyrosine (E345Y), and the substitution at amino acid 372 is leucine (F372L). In certain aspects, the aglycosylated variant human IgG Fc domain may be Fc-V26 (SEQ ID NO: 45).

In some aspects, an aglycosylated variant human Fc domain may comprise a substitution at amino acid 299 (e.g., T299L).

A variant Fc domain polypeptide may be characterized as having a certain percentage of identity as compared to an unmodified polypeptide (e.g., a wild-type Fc domain polypeptide) or to any polypeptide sequence disclosed herein. The percentage identity may be about, at least 60%, 65%, 70%, 75%, 80%, 85%, 90%, 95%, 96%, 97%, 98%, 99% or 100% (or any range derivable therein) between the unmodified portions of a modified polypeptide (i.e., the sequence of the modified polypeptide excluding any specified substitutions) and the corresponding wild-type polypeptide. It is also contemplated that percentage of identity discussed above may relate to a particular modified region of a polypeptide as compared to an unmodified region of a polypeptide. For example, a variant Fc domain polypeptide characterized as having at least 90% identity to a wild-type Fc domain means that at least 90% of the amino acids in that variant polypeptide are identical to the amino acids in the wild-type polypeptide.

An antibody Fc domain may be an Fc domain of a human IgG antibody or a variant thereof. In certain aspects, the Fc domain may be an IgG1 Fc domain, such as the Fc domain of an anti-HER2 antibody (e.g., trastuzumab) or the Fc domain of an anti-CD20 antibody (e.g., rituximab). It is also contemplated that a polypeptide may comprise a fusion of an engineered variant Fc domain as disclosed herein fused to a polypeptide not derived from an antibody molecule.

Polypeptides described herein may include a linker in some embodiments. In further embodiments, the linker is a conjugatable linker. In some embodiments, the polypeptide contains an Fc domain from an antibody. It may contain other regions from an antibody, such as another binding domain. The additional binding domain may not be not an FcR binding domain in certain embodiments. In some embodiments, it may contain an antigen binding site or domain from an antibody. This would include all or part of the variable region from an antibody. In other embodiments, a polypeptide contains an Fc domain from an antibody but another binding domain that is a non-FcR binding domain. In some embodiments, the non-Fc binding region is not an antigen binding site of an antibody but specifically binds a cell-surface protein or a soluble protein. In some cases, a cell-surface protein that the non-Fc binding region recognizes is a receptor.

Other polypeptides include those having an aglycosylated Fc domain capable of binding a C1q polypeptide and a second binding domain that is a non-Fc receptor binding domain, wherein the second binding domain is capable of specifically binding a cell-surface molecule or a soluble protein. In some embodiments, the second binding domain is an antigen binding domain of an antibody ("Ig variable domain"). In some aspects, the polypeptide may be a full-length antibody. In some cases, the second binding domain is not an antibody antigen binding domain. In some embodiments, the second binding domain is capable of specifically binding a cell-surface molecule that is a proteinaceous molecule. In some aspects, the second binding domain is capable of specifically binding a soluble protein.

Embodiments also concern a nucleic acid that encodes any of the polypeptides discussed herein. The nucleic acid may be isolated and/or recombinant. It may be a nucleic acid segment that is isolated and/or recombinant. In some embodiments, the nucleic acid is DNA while in others it is RNA. In certain embodiments, the nucleic acid is a DNA segment. In other embodiments, the nucleic acid is an expression vector that is capable of expressing any of the polypeptides having an Fc binding domain with one or more substitutions that specifically binds a human C1q. A nucleic acid may encode one or more polypeptides discussed above, which, depending on how the polypeptide is produced may or may not be glycosylated.

In some embodiments, there are nucleic acids encoding a polypeptide with an Fc domain capable of specifically binding a human C1q. The nucleic acid may be placed in a host cell that can express the polypeptide, particularly an aglycosylated version of the polypeptide. The host cell may be a prokaryotic cell, such as a bacterial cell. Alternatively, the host cell may be a eukaryotic cell, such as a mammalian cell. In some embodiments, a host cell contains a first expression vector, though it may comprise a second expression vector as well. Because some antibodies are made of multiple polypeptides, a host cell that expresses these polypeptides is contemplated in some embodiments. For example, in some embodiments there is a host cell that includes a second expression vector that encodes a polypeptide comprising an immunoglobulin light chain.

In some embodiments, there is a population of host cells, wherein the population contains a plurality of host cells that express polypeptides having different Fc domains. It is contemplated that the amino acid sequence of any two different Fc domains differs in identity by less than 20%, 15%, 10%, 5% or less.

In some embodiments there are methods of making the polypeptides described herein (polypeptides having an aglycosylated Fc region) as well as methods of using these polypeptides. Any of these methods may be implemented with respect to any of the polypeptides described herein.

In some embodiments there are methods for preparing an aglycosylated polypeptide comprising: a) obtaining a host cell capable of expressing an aglycosylated polypeptide comprising an Fc domain capable of binding C1q; b) incubating the host cell in culture under conditions to promote expression of the aglycosylated polypeptide; and, c) purifying expressed polypeptide from the host cell. In some embodiments, the host cell is a prokaryotic cell, such as a bacterial cell. In other embodiments the host cell is a eukaryotic cell and the polypeptide comprises a T299L substitution. In further embodiments, methods involve collecting expressed polypeptide from the supernatant, which may be done prior to purification.

In some embodiments methods involve purifying the polypeptide from the supernatant. This may involve subjecting the polypeptides from the supernatant to filtration, HPLC, anion or cation exchange, high performance liquid chromatography (HPLC), affinity chromatography or a combination thereof. In some embodiments, methods involve affinity chromatography using staphylococcal Protein A, which binds the IgG Fc region. Other purification methods are well known to those of ordinary skill in the art.

In some embodiments, there is provided a pharmaceutical formulation comprising a polypeptide or nucleic acid of the present embodiments in a pharmaceutically acceptable carrier.

In some embodiments, there are provided methods of inducing an immune response in a subject comprising providing to the subject an antibody, wherein the antibody is aglycosylated and comprises an Fc domain of the present embodiments. In some aspects, the aglycosylated antibody may be capable of specifically binding human C1q. In some aspects, the aglycosylated antibody may be capable of specifically binding human C1q and human activating Fc receptors. In certain aspects, the aglycosylated antibody may be capable of specifically binding an FcγRIIB polypeptide at a level that is at least 50-fold less than a glycosylated, wild-type version of the antibody. In some aspects, the antibody may be an aglycosylated version of a therapeutic antibody.

In a further embodiment, leukemia cell death may be induced by the polypeptides comprising the Fc variants are enhanced compared to the leukemia cell death induced by a polypeptide comprising a wild-type human IgG Fc region. In still a further embodiment, the polypeptides according to the invention exhibit a strongly enhanced CDC compared to the CDC induced by a polypeptide comprising a wild-type human IgG Fc region. In still a further embodiment, the polypeptides according to the present invention may not exhibit ADCC or ADCP compared to wild-type human IgG antibodies.

In a further embodiment killing of cells targeted by antibodies comprising variant Fc polypeptides as contemplated herein is enhanced compared to the leukemia cell death induced by a polypeptide comprising a wild-type human IgG Fc region. In still a further embodiment, the polypeptide according to the invention exhibits a strongly enhanced CDC compared to the CDC induced by a polypeptide comprising a wild-type human IgG Fc region.

In one embodiment, a method is provided for treating a subject having a tumor comprising administering to the subject an effective amount of a pharmaceutical formulation of the present embodiments. In some aspects, the method may induce complement-dependent cytotoxicity. In some aspects, the method may induce antibody-dependent cytotoxicity. In other aspects, the method may not induce antibody-dependent cytotoxicity. In some aspects, the tumor may be a solid tumor or a hematological tumor. In certain aspects, the subject may be a human patient. In some aspects, the pharmaceutical formulation may be administered intratumorally, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage. In some aspects, the method may further comprise administering at least a second anticancer therapy to the subject, such as, for example, a surgical therapy, chemotherapy, radiation therapy, cryotherapy, hormone therapy, immunotherapy or cytokine therapy.

In one embodiment, a composition comprising a variant Fc domain of the present embodiments or a nucleic acid encoding a variant Fc domain of the present embodiments is provided for use in the treatment of a disease. Said disease may be a disease treating by inducing complement dependent cytotoxicity against a target cell. In some aspects, the disease may be cancer. In another embodiment, the use of a polypeptide according to the present embodiments or a nucleic acid encoding a polypeptide according to the present embodiments in the manufacture of a medicament for the treatment of a disease such as cancer is provided.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein, the term "affinity" refers to the equilibrium constant for the reversible binding of two agents and is expressed as $K_D$. Affinity of a binding domain to its target can be, for example, from about 100 nanomolar (nM) to about 0.1 nM, from about 100 nM to about 1 picomolar (pM), or from about 100 nM to about 1 femtomolar (fM); alternatively, it can be between 100 nM and 1 nM or between 0.1 nM and 10 nM. Moreover, it is contemplated that agents specifically bind when there is an affinity between the two agents that is in the affinity ranges discussed above.

As used herein the terms "encode" or "encoding," with reference to a nucleic acid, are used to make the invention readily understandable by the skilled artisan; however, these terms may be used interchangeably with "comprise" or "comprising," respectively.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A shows FACS scanning results of each represented spheroplasted E. coli cells when C1q-PE was labeled in PBS. FIG. 3B shows FACS scanning results of each represented spheroplasted E. coli cell when anti-LPS-antibody-PE was labeled in PBS. FIG. 3C shows FACS scanning results with C1q-PE in high-salt buffer. FIG. 3D shows FACS scanning results spheroplasted E. coli cells with FcγRIIIa-SA-PE. Mean fluorescence intensities for each panel are provided in Table 3.

FIG. 4A shows C1q-PE binding intensities of cells after each of seven rounds of library sorting and resorting. With the exception of the 1$^{st}$ round, the right most peak represents the "after sorting" condition in each histogram. FIG. 4B shows C1q-PE or FcγRIIIa-SA-PE binding intensities of libraries during seven rounds of library sorting and resorting. The right most peak in each histogram represents the "after sorting" condition.

FIGS. 9A-D show the SPR sensorgrams of Rituximab (FIG. 9A), RAI (FIG. 9B), RAII (FIG. 9C), and RGII (FIG. 9D). Detailed kinetic values from SPR sensorgram analysis are provided in Table 5.

FIGS. 11A-F show the SPR sensorgrams of RAIII; C1q (FIG. 11A), monomeric FcγRI (FIG. 11B), dimeric FcγRIIa$_{H131}$ (FIG. 11C), dimeric FcγRIIa$_{R131}$ (FIG. 11D), dimeric FcγRIIIa$_{V157}$ (FIG. 11E), and dimeric FcγRIIIa$_{F157}$ (FIG. 11F). The detailed kinetic values from SPR sensorgram analysis are provided in Table 8.

FIGS. 18A-C show the SPR sensorgrams of Rituximab (FIG. 18A), RAI (FIG. 18B), and RAII (FIG. 18C) at pH 6.0. FIG. 18D show the SPR sensorgrams of Rituximab, RAI, and RAII at pH 7.4. The detailed kinetic values from SPR sensorgram analysis are provided in Table 7.

DESCRIPTION OF ILLUSTRATIVE EMBODIMENTS

Figure 1A:
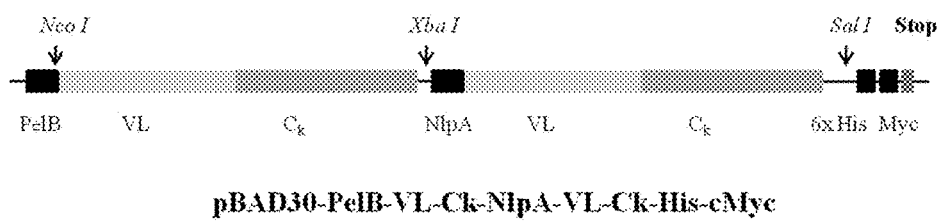
FIGS. 1A-B. Brief scheme of two plasmid system for bacterial periplasmic display of Trastuzumab light chain (FIG. 1A) and Trastuzumab heavy chain (FIG. 1B).

Provided herein are methods and compositions involving polypeptides having engineered antibody Fc domains displaying improved binding to C1q. Such polypeptides may comprise an aglycosylated Fc domain that comprises one or more substitutions compared to a native Fc domain (SEQ ID NO: 1). Additionally, some Fc domains may bind selectively to C1q or to C1q and to certain Fc receptors but not others. For example, polypeptides may comprise an aglycosylated Fc domain that selectively binds C1q, but that does not detectably bind to any FcγRs. Another polypeptide may be provided that comprises an aglycosylated Fc domain that selectively binds C1q and the activating FcγRs, but that does not detectably bind to the inhibitory FcγRIIb. Yet another polypeptide may be provided that comprises a glycosylated Fc domain that selectively binds C1q and some or all of the activating FcγRs, but that does not detectably bind to the inhibitory FcγRIIB Furthermore, methods and compositions are provided for promoting complement-dependent cytotoxicity (CDC) and antibody-dependent cell cytotoxicity (ADCC) using a modified aglycosylated antibody.

I. Complement-Dependent Cytotoxicity

One of the key mechanisms by which antibodies kill target cells they recognize is via the recruitment and activation of proteins of the complement system. Immune complexes on pathogenic cells are recognized by the complement protein C1q, which binds to the Fc domain of antibody molecules. The complex between the Fc domains of antibodies bound to pathogenic cells and C1q activates a cascade of biochemical reactions that either kill the cell directly via the complement membrane attack complex (MAC) or by depositing the complement molecule C3b on the cell surface which then "flags" the pathogenic cell for destruction. The process by which antibodies kill pathogenic cells via complement activation is called complement dependent cytotoxicity (CDC).

The potency of CDC depends on the ability of antibodies to bind to C1q. In turn this depends on the interaction between the Fc domains of antibodies and C1q. This interaction is normally completely abolished when the single carbohydrate chain appended to the Fc polypeptide has been removed, i.e., in antibodies that are aglycosylated.

However, protein engineering was used to generate an Fc domain that not only binds to C1q but does so with a much higher affinity than that of human glycosylated Fc counterpart. What is even more remarkable is that the Fc domain is specific for C1q. Normally the IgG Fc domain binds to a variety of Fc receptor proteins on the surface of leukocytes. The binding of Fc receptors with the Fc domain triggers a series of signaling events leading to immunological effects that generally aid the clearance of pathogenic cells. However, there are instances in which engagement of Fc receptors is detrimental, for example when the binding of an antibody molecules on the surface of cancer cells to Fc receptors on a neighboring cell mediate the clustering of the cancer cell surface molecules in turn signaling to the cancer cell to proliferate. Thus, an Fc domain that can only induce cancer cell killing by CDC without binding to Fc receptors may greatly enhance the therapeutic potency of certain antibody drugs.

II. Antibody Fc Domains

In certain embodiments, there are compositions comprising a proteinaceous molecule that has been modified relative to a native or wild-type protein. In some embodiments that proteinaceous compound has been deleted of amino acid residues; in other embodiments, amino acid residues of the proteinaceous compound have been replaced; while in still further embodiments both deletions and replacements of amino acid residues in the proteinaceous compound have been made. Furthermore, a proteinaceous compound may include an amino acid molecule comprising more than one polypeptide entity. As used herein, a "proteinaceous molecule," "proteinaceous composition," "proteinaceous compound," "proteinaceous chain," or "proteinaceous material" generally refers, but is not limited to, a protein of greater than about 200 amino acids or the full-length endogenous sequence translated from a gene; a polypeptide of 100 amino acids or greater; and/or a peptide of 3 to 100 amino acids. All the "proteinaceous" terms described above may be used interchangeably herein; however, it is specifically contemplated that embodiments may be limited to a particular type of proteinaceous compound, such as a polypeptide. Furthermore, these terms may be applied to fusion proteins or protein conjugates as well. A protein may include more than one polypeptide. An IgG antibody, for example, has two heavy chain polypeptides and two light chain polypeptides, which are joined to each other through disulfide bonds.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any amino acid, amino acid derivative, or amino acid mimic as would be known to one of ordinary skill in the art. In certain embodiments, the residues of the proteinaceous molecule are sequential, without any non-amino acid residue interrupting the sequence of amino acid residues. In other embodiments, the sequence may comprise one or more non-amino acid moieties. In particular embodiments, the sequence of residues of the proteinaceous molecule may be interrupted by one or more non-amino acid moieties.

As used herein a "distinct Fc domain" may be defined as a domain that differs from another Fc by as little as one amino acid. Methods for making a library of distinct antibody Fc domains or nucleic acids that encode antibodies are well known in the art. For example, in some cases Fc domains may be amplified by error prone PCR. Furthermore, in certain cases a plurality of antibody Fc domains may comprise a stretch (1, 2, 3, 4, 5, 6, 7, 8, 9, 10 or more) of amino acids that have been randomized. In certain cases, specific mutations may be engineered into Fc domains. For example, in some aspects, residues that are normally glycosylated in an antibody Fc domain may be mutated. Furthermore, in certain aspects, residues that are normally glycosylated (or adjacent residues) may be used as a site for an insertion of 1, 2, 3, 4, 5, 6, 7, 8, 9, 10 or more amino acids.

A polypeptide may comprise an aglycosylated antibody Fc domain capable of binding an FcR polypeptide. In some aspects, the aglycosylated Fc domain may be further defined as having a specific affinity for an FcR polypeptide under physiological conditions. For instance an Fc domain may have an equilibrium dissociation constant between about $10^{-6}$ M to about $10^{-9}$ M under physiological conditions. Furthermore in some aspects an aglycosylated Fc domain may be defined as comprising one or more amino acid substitutions or insertions relative to a wild-type sequence, such as a human wild-type sequence.

Means of preparing such a polypeptide include those discussed in PCT Publn. WO 2008/137475, which is hereby incorporated by reference. One can alternatively prepare such polypeptides directly by genetic engineering techniques such as, for example, by introducing selected amino acid substitutions or insertions into a known Fc background, wherein the insertion or substitution provides an improved FcR binding capability to aglycosylated Fc regions, as discussed above. In some embodiments, an Fc domain is engineered to bind one or more specific Fc receptors. Additionally or alternatively, an Fc domain may be engineered so that it does not specifically bind one or more specific Fc receptors.

In some embodiments, an aglycosylated Fc domain comprises a specific binding affinity for an FcR such as human FcγRIa, FcγRIIa, FcγRIIb, FcγRIIc, FcγRIIIa, FcγRIIIb, FcαRI, or for C1q. Thus, in some aspects an aglycosylated Fc domain of the invention is defined as an Fc domain with a specific affinity for C1q. In other aspects, an aglycosylated Fc domain of the invention is defined as an Fc domain with a specific affinity for C1q and activating Fc receptors, but not inhibitory FcγRIIb. The binding affinity of an antibody Fc or other binding protein can, for example, be determined by the Scatchard analysis of Munson and Pollard (1980). Alternatively, binding affinity can be determined by surface plasmon resonance or any other well known method for determining the kinetics and equilibrium constants for protein: protein interactions.

Amino acids sequences of Fc domains of the isolated IgG variants with specific affinity for C1q with changes shown relative to wild-type Fc (SEQ ID NO: 1) are as follows: Fc701 (SEQ ID NO: 2; D270H; E382V; M428I; L443P; S444V), Fc702 (SEQ ID NO: 3; L351Q), Fc703 (SEQ ID NO: 4; E233L; G236E; V240A; F275Y; V303A; L351Q), Fc704 (SEQ ID NO: 5; E233L; G236E; V240A; F275Y; V303A), Fc705 (SEQ ID NO: 6; G237V; E318G; L328P; I336F; S337L; K338S; A339V; K340L; G341R Q342L; R344L; R355Q; D356G), Fc801 (SEQ ID NO: 7; K320E; Q386R), Fc707 (SEQ ID NO: 8; L251F; V262M; S267G; P291S; I336L; S337A; K338H; K340R; Q342P; L368P; F372L; W381R; N421S), Fc708 (SEQ ID NO: 9; L309Q; L328P; L368P; H429L; E430G), Fc802 (SEQ ID NO: 10; L235K; G236M; G237R; L351Q), Fc710 (SEQ ID NO: 11; L234I; L235V; S267G; K338I; K340R; Q342P; F404S; K439R), Fc711 (SEQ ID NO: 12; D270G; I336R; K340R; Q342P; R344L; E345D; R416G), and Fc712 (SEQ ID NO: 13; E382V; M428I).

Amino acids sequences of Fc domains of the isolated IgG variants with specific affinity for C1q and activating Fc receptors, but not inhibitory FcγRIIb, with changes shown relative to wild-type Fc (SEQ ID NO: 1) are as follows: Fc713 (SEQ ID NO: 14; E233D; L234Y; L235Q; G236K; G237R; T250A; I253V; D265G; H285L; N297S; K338P; A339Y; G341R; Q342K; E345A; K360R; Q418R; T437A), Fc714 (SEQ ID NO: 15; E233D; L234Y; L235Q; G236K; G237R; I253V; N297S; K338P; A339Y; G341R; Q342K; E345A; K360R), Fc715 (SEQ ID NO: 16; E233D; L234Y; L235Q; G236K; G237R; P238L; I253V; D270N; T307P; N315I; L328P; Q342H; T350P; V379A; E388G; Q419R), Fc716 (SEQ ID NO: 17; E233D; L234Y; L235Q; G236K; G237R; I253V; K326R; F372C; D401G; F404L; L406F; K414R; Y436C), Fc717 (SEQ ID NO: 18; E233G; L234P; L235P; G236R), Fc719 (SEQ ID NO: 19; L235M; G236W; G237R; V240I; V263M; K290E; S324P; T350A; C425Y), Fc803 (SEQ ID NO: 20; T299K; S354P; P445S), Fc720 (SEQ ID NO: 21; M252V; N315S; I336M; K340R; Q342D), Fc805 (SEQ ID NO: 22; V308A; S337P; K338Q; K340R; Q342P; R344G; E345Y; F372L), Fc722 (SEQ ID NO: 23; G236W; G237L; V284E; I332V; I336A; K340E; P343L; R344S; T394P), Fc-V1 (SEQ ID NO: 36; M252V), Fc-V11 (SEQ ID NO: 37; K246N; K322E; G402D), Fc-V12 (SEQ ID NO: 38; F242L; N315S; I336M; K340R; Q342D; A378T; Q386R); Fc-V15 (SEQ ID NO: 39; K334E; L351Q; N421D); Fc-V17 (SEQ ID NO: 40; G341A; L351Q); Fc-V18 (SEQ ID NO: 41; M252V; G341A; L351Q); Fc-V19 (SEQ ID NO: 42; K246Q; T260A; N315S; Q386R); Fc-V23 (SEQ ID NO: 43; K246N; M252V; K322E; R344G; E345Y; F372L); Fc-V24 (SEQ ID NO: 44; F242L; M252V; K338Q; G341A; E345Y); and Fc-V26 (SEQ ID NO: 45; K334E; G402D; K338Q; Q342P; R344G; E345Y; F372L).

By "position" as used herein is meant a location in the sequence of a protein. Positions may be numbered sequentially, or according to an established format, for example the EU index for antibody numbering.

For all positions discussed in the present invention, numbering is according to the EU index. The "EU index" or "EU index as in Kabat" or "EU numbering scheme" refers to the numbering of the EU antibody (Edelman et al., 1969; Kabat et al., 1991; both incorporated herein by reference in their entirety). Thus, position 1 of the sequence provided in SEQ ID NO: 1 corresponds to position 231 of the EU index as in Kabat.

In certain embodiments the size of the at least one Fc polypeptide proteinaceous molecule may comprise, but is not limited to, about or at least 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 350, 400, 450, 500, 550, 600, 650, 700, 750, 800, 850, 900, 950, 1000 or greater amino molecule residues, and any range derivable therein. Compounds may include the above-mentioned number of contiguous amino acids from SEQ ID NO: 1 (human IgG Fc polypeptide) or from SEQ ID NOs: 2-23 and these may be further qualified as having a percent identity or homology to SEQ ID NO: 1 (discussed below).

A. Modified Proteins and Polypeptides

Some embodiments concern modified proteins and polypeptides, particularly a modified protein or polypeptide that exhibits at least one functional activity that is comparable to the unmodified version, yet the modified protein or polypeptide possesses an additional advantage over the unmodified version, such as provoking CDC, being easier or cheaper to produce, eliciting fewer side effects, and/or having better or longer efficacy or bioavailability. Thus, when the present application refers to the function or activity of "modified protein" or a "modified polypeptide" one of ordinary skill in the art would understand that this includes, for example, a protein or polypeptide that 1) performs at least one of the same activities or has at least one of the same specificities as the unmodified protein or polypeptide, but that may have a different level of another activity or specificity; and 2) possesses an additional advantage over the unmodified protein or polypeptide. Determination of activity may be achieved using assays familiar to those of skill in the art, particularly with respect to the protein's activity, and may include for comparison purposes, for example, the use of native and/or recombinant versions of either the modified or unmodified protein or polypeptide. It is specifically contemplated that embodiments concerning a "modified protein" may be implemented with respect to a "modified polypeptide," and vice versa. In addition to the modified proteins and polypeptides discussed herein, embodiments may involve domains, polypeptides, and proteins described in PCT Publn. WO 2008/137475, which is hereby specifically incorporated by reference.

Modified proteins may possess deletions and/or substitutions of amino acids; thus, a protein with a deletion, a protein with a substitution, and a protein with a deletion and a substitution are modified proteins. In some embodiments these modified proteins may further include insertions or added amino acids, such as with fusion proteins or proteins with linkers, for example. This may include the insertion of a targeting peptide or polypeptide or simply a single residue. Terminal additions, called fusion proteins, are discussed below.

A "modified deleted protein" lacks one or more residues of the native protein, but possesses the specificity and/or activity of the native protein. A "modified deleted protein" may also have reduced immunogenicity or antigenicity. An example of a modified deleted protein is one that has an amino acid residue deleted from at least one antigenic region (i.e., a region of the protein determined to be antigenic in a particular organism, such as the type of organism that may be administered the modified protein).

Substitutional or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a native polypeptide are included, provided the biological activity of the protein is maintained. A modified protein may be biologically functionally equivalent to its native counterpart.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure with or without appreciable loss of interactive binding capacity with structures such as, for example, binding sites to substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated that various changes may be made in the DNA sequences of genes without appreciable loss of their biological utility or activity, as discussed below. A proteinaceous molecule has "homology" or is considered "homologous" to a second proteinaceous molecule if one of the following "homology criteria" is met: 1) at least 30% of the proteinaceous molecule has sequence identity at the same positions with the second proteinaceous molecule; 2) there is some sequence identity at the same positions with the second proteinaceous molecule and at the nonidentical residues, at least 30% of them are conservative differences, as described herein, with respect to the second proteinaceous molecule; or 3) at least 30% of the proteinaceous molecule has sequence identity with the second proteinaceous molecule, but with possible gaps of nonidentical residues between identical residues. As used herein, the term "homologous" may equally apply to a region of a proteinaceous molecule, instead of the entire molecule. If the term "homology" or "homologous" is qualified by a number, for example, "50% homology" or "50% homologous," then the homology criteria, with respect to 1), 2), and 3), is adjusted from "at least 30%" to "at least 50%." Thus it is contemplated that there may homology of at least 30%, 35%, 40%, 45%, 50%, 55%, 60%, 65%, 70%, 75%, 80%, 85%, 90%, 95%, or more between two proteinaceous molecules or portions of proteinaceous molecules.

Alternatively, a modified polypeptide may be characterized as having a certain percentage of identity to an unmodified polypeptide or to any polypeptide sequence disclosed herein, including any of SEQ ID NOs: 1-23. The percentage identity may be at most or at least 50%, 55%, 60%, 65%, 70%, 75%, 80%, 85%, 90%, 95%, 96%, 97%, 98%, 99% or 100% (or any range derivable therein) between two proteinaceous molecules or portions of proteinaceous molecules. It is contemplated that percentage of identity discussed above may relate to a particular region of a polypeptide compared to an unmodified region of a polypeptide. For instance, a polypeptide may contain a modified or mutant Fc domain that can be characterized based on the identity of the amino acid sequence of the modified or mutant Fc domain to an unmodified or mutant Fc domain from the same species. A modified or mutant human Fc domain characterized, for example, as having 90% identity to an unmodified Fc domain means that 90% of the amino acids in that domain are identical to the amino acids in the unmodified human Fc domain (SEQ ID NO: 1).

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine, and isoleucine.

B. Modified Antibodies and Proteinaceous Compounds with Heterologous Regions

Once an Fc domain has been isolated, it may be desired to link the molecule to at least one agent to form a conjugate to enhance the utility of that molecule. For example, in order to increase the efficacy of Fc domains or antibody molecules as diagnostic or therapeutic agents, it is conventional to link or covalently bind or complex at least one desired molecule or moiety. Such a molecule or moiety may be, but is not limited to, at least one effector or reporter molecule. Effecter molecules comprise molecules having a desired activity, e.g., cytotoxic activity. Non-limiting examples of effector molecules that have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety that may be detected using an assay. Non-limiting examples of reporter molecules that have been conjugated to antibodies include enzymes, radiolabel s, haptens, fluorescent labels, phosphorescent molecules, chemiluminescent molecules, chromophores, luminescent molecules, photoaffinity molecules, colored particles, or ligands, such as biotin. Another such example is the formation of a conjugate comprising an antibody linked to a cytotoxic or anti-cellular agent, and may be termed "immunotoxins." Techniques for labeling such a molecule are known to those of skill in the art and have been described herein above.

Labeled proteins, such as Fc domains that have been prepared in accordance with the invention may also then be employed, for example, in immunodetection methods for binding, purifying, removing, quantifying, and/or otherwise generally detecting biological components, such as protein(s), polypeptide(s), or peptide(s). Some immunodetection methods include enzyme linked immunosorbent assay (ELISA), radioimmunoassay (MA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; and De Jager et al., 1993, each incorporated herein by reference.

The Fc domain molecules, including antibodies, may be used, for example, in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Abbondanzo et al., 1990).

Some embodiments concern an Fc polypeptide proteinaceous compound that may include amino acid sequences from more than one naturally occurring or native polypeptides or proteins. Embodiments discussed above are contemplated to apply to this section, and vice versa. For instance, a modified antibody is one that contains a modified Fc domain with an antigen binding domain. Moreover, the antibody may have two different antigen binding regions, such as a different region on each of the two heavy chains. Alternatively or additionally, in some embodiments, there are polypeptides comprising multiple heterologous peptides and/or polypeptides ("heterologous" meaning they are not derived from the same polypeptide). A proteinaceous compound or molecule, for example, could include a modified Fc domain with a protein binding region that is not from an antibody. In some embodiments, there are polypeptides comprising a modified Fc domain with a protein binding region that binds a cell-surface receptor. These proteinaceous molecules comprising multiple functional domains may be two or more domains chemically conjugated to one another or it may be a fusion protein of two or more polypeptides encoded by the same nucleic acid molecule. It is contemplated that proteins or polypeptides may include all or part of two or more heterologous polypeptides.

Thus, a multipolypeptide proteinaceous compound may be comprised of all or part of a first polypeptide and all or part of a second polypeptide, a third polypeptide, a fourth polypeptide, a fifth polypeptide, a sixth polypeptide, a seventh polypeptide, an eight polypeptide, a ninth polypeptide, a tenth polypeptide, or more polypeptides.

Amino acids, such as selectively-cleavable linkers, synthetic linkers, or other amino acid sequences, may be used to separate proteinaceous moieties.

Polypeptides or proteins (including antibodies) having an antigen binding domain or region of an antibody and an aglycosylated Fc domain can be used against any antigen or epitope, including but not limited to proteins, subunits, domains, motifs, and/or epitopes belonging to the following list of targets: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin B, Cathepsin S, Cathepsin V, Cathepsin X/ZIP, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Clostridium botulinum toxin, Clostridium perfringens toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MM), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC 1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibiting substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PB SF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), PIGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, 5100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (fit-1), VEGF, VEGFR, VEGFR-3 (fit-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9B, WNT10A, WNT10B, WNT11, WNT16, XCL1, XCL2, XCR1, XCR1, XEDAR, XIAP, XPD, and receptors for hormones and growth factors. In some embodiments, a polypeptide or protein has an antigen binding domain specific for one or more cell surface tumor antigens. Methods and compositions may be employed to target a tumor cell for CDC.

Any antibody of sufficient selectivity, specificity, or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell capable of binding to specific target cells. Embodiments further include adjoining all or part of an aglycosylated Fc domain to all or part of any of the proteins listed in Table 1. It is contemplated that embodiments include, but are not limited to, the examples provided in Table 1 and the description herein.

A ligand for a receptor may be employed to target a cell expressing on its surface the receptor for the ligand. Ligands also include, for instance, CD95 ligand, TRAIL, TNF (such as TNF-α or TNF-β), growth factors, including those discussed above, such as VEGF, and cytokines, such as interferons or interleukins, and variants thereof. Embodiments with multiple domains are also contemplated, such as a VEGF Trap fusion protein that includes the second extracellular domain of the VEGF receptor 1 (Flt-1) with the third domain of the VEGF receptor 2 (KDR/Flk-1) and an IgG Fc region.

TABLE 1

Agents/proteins capable of binding specific target cells

| Protein Genus | Subgenus | Species | Subspecies |
|---|---|---|---|
| Antibodies | Polyclonal | | |
| | Monoclonal | Non-recombinant | |
| | | Recombinant | |
| | | | Chimeric |
| | | | Single chain |
| | | | Diabody |
| | | | Multimeric |
| Ligands for cell-surface receptors | | | IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19 |
| | Cytokines/growth factors | | |
| | | Cytokines/growth factors for receptor tyrosine kinases | |
| | | | GM-CSF, G-CSF, M-CSF, EGF, VEGF, FGF, PDGF, HGF, GDNF, Trk, AXL, LTK, TIE, ROR, DDR, KLG, RYK, MuSK ligands |
| Non-Ab binding protein for cell-surface molecule | | | |
| | Binders of cell surface proteins | | |
| | | Cluster of differentiation (CD) molecules | | co-receptor CD4, and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Fc domains can bind to C1q and to an FcR, however, it is contemplated that CDC can be directed not only through an antigen binding domain on the polypeptide containing the Fc domain, but through some other protein binding domain. Consequently, embodiments concern an Fc domain and a heterologous non-antigen binding domain. In certain embodiments, the non-antigen binding domain binds to the cell surface. Therefore, these agents require either chemical conjugation to or fusion with agents/proteins that are C. Antibody Fc Libraries Examples of techniques that could be employed in conjunction with embodiments for creation of diverse antibody Fc domains and/or antibodies comprising such domains may employ techniques similar to those for expression of immunoglobulin heavy chain libraries described in U.S. Pat. No. 5,824,520. Previously employed Fc libraries are discussed in PCT Publn. WO 2008/137475, which is specifically incorporated herein by reference.

III. Antibody-Binding Polypeptides

A variety of antibody-binding domains (e.g., FcR polypeptides) are known in the art and may be used in the methods and compositions of the invention. For example, in some aspects, an FcR may have specificity for a particular type or subtype of Ig, such as IgA, IgM, IgE, or IgG (e.g., IgG1, IgG2a, IgG2b, IgG3, or IgG4). Thus, in some embodiments the antibody-binding domain may be defined as an IgG binding domain. The FcR polypeptide may comprise a eukaryotic, prokaryotic, or synthetic FcR domain. For instance, an antibody Fc-binding domain may be defined as a mammalian, bacterial, or synthetic binding domain. Some Fc-binding domains for use in the invention include but are not limited to a binding domain from one of the polypeptides of Table 2. For example, an Fc-binding polypeptide may be encoded by an FCGR2A, FCGR2B, FCGR2C, FCGR3A, FCGR3B, FCGR1A, Fcgr1, FCGR2, FCGR2, Fcgr2, Fcgr2, FCGR3, FCGR3, Fcgr3, FCGR3, Fcgr3, FCGRT, mrp4, spa, or spg gene. Preferably, an FcR polypeptide for use according to the invention may be an Fc binding region from human FcγRIa, FcγRIIa, FcγRIIb, FcγRIIc, FcγRIIIa, FcγRIIIb, FcαRI, or C1q. A variety of Fc receptors to which Fc domains bind are well known in the art and some examples of receptors are listed below in Table 2.

TABLE 2

Selected FcR Polypeptides

| Protein name | Gene name | Description | Organisms | Length (aa) | Reference |
|---|---|---|---|---|---|
| Fc-gamma RII-a (CD32) | FCGR2A | Low affinity immunoglobulin gamma Fc region receptor II-a precursor | Homo sapiens (Human) | 317 | (Stuart et al., 1987) |
| Fc-gamma RII-a | FCGR2A | Low affinity immunoglobulin gamma Fc region receptor II-a precursor | Pan troglodytes (Chimpanzee) | 316 | |
| Fc-gamma RII-b | FCGR2B | Low affinity immunoglobulin gamma Fc region receptor II-b precursor | Homo sapiens (Human) | 310 | (Stuart et al., 1989) |
| Fc-gamma RII-c | FCGR2C | Low affinity immunoglobulin gamma Fc region receptor II-c precursor | Homo sapiens (Human) | 323 | (Stuart et al., 1989) |
| Fc-gamma RIIIa | FCGR3A | Low affinity immunoglobulin gamma Fc region receptor III-A precursor | Homo sapiens (Human) | 254 | (Ravetch and Perussia, 1989) |
| Fc-gamma RIIIb | FCGR3B | Low affinity immunoglobulin gamma Fc region receptor III-B precursor | Homo sapiens (Human) | 233 | (Ravetch and Perussia, 1989) |
| Fc-gamma RI (CD64) | FCGR1A | High affinity immunoglobulin gamma Fc receptor I precursor | Homo sapiens (Human) | 374 | (Allen and Seed, 1988) |
| Fc-gamma RI | Fcgr1 | High affinity immunoglobulin gamma Fc receptor I precursor | Mus musculus (Mouse) | 404 | (Sears et al., 1990) |
| Fc-gamma RII | FCGR2 | Low affinity immunoglobulin gamma Fc region receptor II precursor | Bos taurus (Bovine) | 296 | (Zhang et al., 1994) |
| Fc-gamma RII | FCGR2 | Low affinity immunoglobulin gamma Fc region receptor II precursor | Cavia porcellus (Guinea pig) | 341 | (Tominaga et al., 1990) |
| Fc-gamma RII | Fcgr2 | Low affinity immunoglobulin gamma Fc region receptor II precursor | Mus musculus (Mouse) | 330 | (Ravetch et al., 1986) |
| Fc- gamma RII | Fcgr2 | Low affinity immunoglobulin gamma Fc region receptor II precursor | Rattus norvegicus (Rat) | 285 | (Bocek and Pecht, 1993) |
| Fc-gamma RIII | FCGR3 | Low affinity immunoglobulin gamma Fc region receptor III precursor | Bos taurus (Bovine) | 250 | (Collins et al., 1997) |
| Fc-gamma RIII | FCGR3 | Low affinity immunoglobulin gamma Fc region receptor III precursor | Macaca fascicularis (Crab eating macaque) (Cynomolgus monkey) | 254 | |
| Fc-gamma RIII | Fcgr3 | Low affinity immunoglobulin gamma Fc region receptor III precursor | Mus musculus (Mouse) | 261 | (Ravetch et al., 1986) |
| Fc-gamma RIII | FCGR3 | Low affinity immunoglobulin gamma Fc region receptor III precursor | Sus scrofa (Pig) | 257 | (Halloran et al., 1994) |
| Fc-gamma RIII | Fcgr3 | Low affinity immunoglobulin gamma Fc region receptor III precursor | Rattus norvegicus (Rat) | 267 | (Zeger et al., 1990) |
| FcRn | FCGRT | IgG receptor transporter FcRn large subunit p51 precursor | Homo sapiens (Human) | 365 | |

TABLE 2-continued

Selected FcR Polypeptides

| Protein name | Gene name | Description | Organisms | Length (aa) | Reference |
|---|---|---|---|---|---|
| FcRn | FCGRT | IgG receptor transporter FcRn large subunit p51 precursor | *Macaca fascicularis* (Crab eating macaque) (Cynomolgus monkey) | 365 | |
| FcRn | Fcgrt | IgG receptor transporter FcRn large subunit p51 precursor | *Mus musculus* (Mouse) | 365 | (Ahouse et al., 1993) |
| FcRn | Fcgrt | IgG receptor transporter FcRn large subunit p51 precursor | *Rattus norvegicus* (Rat) | 366 | (Simister and Mostov, 1989) |
| MRP protein | mrp4 | Fibrinogen- and Ig-binding protein precursor | *Streptococcus pyogenes* | 388 | (Stenberg et al., 1992) |
| Protein B | | cAMP factor | *Streptococcus agalactiae* | 226 | (Ruhlmann et al., 1988) |
| protein A | spa | Immunoglobulin G-binding protein A precursor | *Staphylococcus aureus* (strain NCTC 8325) | 516 | (Uhlen et al., 1984) |
| protein A | spa | Immunoglobulin G-binding protein A precursor | *Staphylococcus aureus* | 508 | (Shuttleworth et al., 1987) |
| protein A | spa | Immunoglobulin G-binding protein A precursor | *Staphylococcus aureus* (strain Mu50/ATCC 700699) | 450 | (Kuroda et al., 2001) |
| protein A | spa | Immunoglobulin G-binding protein A precursor | *Staphylococcus aureus* (strain N315) | 450 | (Kuroda et al., 2001) |
| protein G | spg | Immunoglobulin G-binding protein G precursor | *Streptococcus* sp. group G | 448 | (Fahnestock et al., 1986) |
| protein G | spg | Immunoglobulin G-binding protein G precursor | *Streptococcus* sp. group G | 593 | (Olsson et al., 1987) |
| protein H | | Immunoglobulin G-binding protein H precursor | *Streptococcus pyogenes* serotype M1 | 376 | (Gomi et al., 1990) |
| Protein sbi | sbi | Immunoglobulin G-binding protein sbi precursor | *Staphylococcus aureus* (strain NCTC 8325-4) | 436 | (Zhang et al., 1998) |
| Allergen Asp fl 1 | | Allergen Asp fl 1 causes an allergic reaction in human. Binds to IgE and IgG | *Aspergillus flavus* | 32 | |
| Allergen Asp fl 2 | | Allergen Asp fl 2 causes an allergic reaction in human. Binds to IgE and IgG | *Aspergillus flavus* | 20 | |
| Allergen Asp fl 3 | | Allergen Asp fl 3 causes an allergic reaction in human. Binds to IgE and IgG | *Aspergillus flavus* | 32 | |
| Fc-epsilon RI | | IgE receptor displayed on Mast cells, Eosinophils and Basophils | *Homo sapiens* (Human) | | |
| Fc-alpha RI (CD86) | | IgA (IgA1, IgA2) receptor displayed on Macrophages | *Homo sapiens* (Human) | | |
| C1q | C1QA NP_057075.1, C1QB NP_000482.3, C1QC NP_758957.1 | C1q is multimeric complex that binds to antibody Fc composed of 6 A chains, 6 B chains and 6 C chains | *Homo sapiens* (Human) | | |

IV. Methods for Screening Antibody Fc Domains

In certain aspects there are methods for identifying antibody Fc domains with a specific affinity for a target ligand (e.g., an antibody-binding polypeptide, such as an Fc receptor). Such methods are described herein, as well as in PCT Publn. WO 2008/137475, which is hereby specifically incorporated by reference in its entirety.

The polypeptides screened may comprise a large library of diverse candidate Fc domains, or, alternatively, may comprise particular classes of Fc domains (e.g., engineered point mutations or amino acid insertions) selected with an eye towards structural attributes that are believed to make them more likely to bind the target ligand. In one embodiment, the candidate polypeptide may be an intact antibody, or a fragment or portion thereof comprising an Fc domain.

To identify a candidate Fc domain capable of binding a target ligand, one may carry out the steps of: providing a population of Gram-negative bacterial cells that each expresses a distinct antibody Fc domain; admixing the bacteria and at least a first labeled or immobilized target ligand (FcR polypeptide) capable of contacting the antibody Fc domain; and identifying at least a first bacterium expressing a molecule capable of binding the target ligand.

In some aspects of the aforementioned method, the binding between antibody Fc domain and a labeled FcR polypeptide will prevent diffusion out of a bacterial cell. In this way, molecules of the labeled ligand can be retained in the periplasm of the bacterium comprising a permeabilized outer membrane. Alternatively, the periplasm can be removed, whereby the Fc domain will cause retention of the bound candidate molecule since Fc domains are shown to associate with the inner membrane. The labeling may then be used to isolate the cell expressing a binding polypeptide capable of binding the FcR polypeptide, and the gene encoding the Fc domain polypeptide may be isolated. The molecule capable of binding the target ligand may then be produced in large quantities using in vivo or ex vivo expression methods, and then used for any desired application, for example, for diagnostic or therapeutic applications. Furthermore, it will be understood that isolated antibody Fc domains identified may be used to construct an antibody fragment or full-length antibody comprising an antigen binding domain.

In further embodiments, methods of screening may comprise at least two rounds of selection wherein the sub-population of bacterial cells obtained in the first round of selection is subjected to at least a second round of selection based on the binding of the candidate antibody Fc domain to an FcR. Furthermore in some aspects the sub-population of bacterial cells obtained in the first round of selection may be grown under permissive conditions prior to a second selection (to expand the total number of cells). Thus, in some aspects, methods may comprise 2, 3, 4, 5, 6, 7, 8, 9, 10 or more rounds of selection. Furthermore, in some aspects, a sub-population of bacterial cells obtained from each round of selection will be grown under permissive conditions before a subsequent round of selection. Cells isolated following one or more such rounds of selection may be subjected to additional rounds of mutagenesis. In some cases, selection will be performed after removing FcR polypeptide that is not bound to the antibody. Furthermore, in some cases the stringency of selection may be modified by adjusting the pH, salt concentration, or temperature of a solution comprising bacteria that display antibodies. Thus, in some aspects, it may be preferred that a bacterial cell of the invention is grown at a sub-physiological temperature, such as at about 25° C.

In still further aspects, a method of producing a bacterial cell according to the invention may be further defined as a method of producing a nucleic acid sequence encoding an Fc domain that binds to at least a first FcR. Thus, a bacterial cell produced by the methods herein may be used to clone a nucleic acid sequence encoding the Fc domain having a specific affinity for an FcR polypeptide. Methods for isolating and amplifying such a nucleic acid from a cell for example by PCR are well known in the art and further described below. Thus, a nucleic acid sequence produced by the foregoing methods is included as part of the instant invention. Furthermore, such a sequence may be expressed in a cell to produce an Fc domain having a specific affinity for an FcR. Thus, in some aspects, the invention provides a method for producing an Fc domain having a specific affinity for an FcR. Furthermore, the invention includes antibody Fc domains produced by the methods of the invention. It will be understood however that the antibody Fc domains produced by such a screen may be combined with antibody variable regions that have an affinity for a particular target ligand and these antibodies are also included as part of the invention.

A. Periplasmic Expression of Antibody Fc Domains

In some embodiments, a polypeptide comprising an antibody Fc domain may be expressed in the periplasmic space of Gram-negative bacteria. Furthermore, in some aspects an antibody Fc domain may be anchored to the periplasmic face of the inner membrane. Methods and compositions for the anchoring of polypeptides to the inner membrane of Gram-negative bacteria have previously been described (U.S. Pat. Nos. 7,094,571, 7,419,783, 7,611,866 and U.S. Patent Publn. No. 2003/0219870). For example, an Fc domain may be directly fused to a membrane spanning or membrane bound polypeptide or may interact (e.g., via protein-protein interactions) with a membrane spanning or membrane bound polypeptide. Such a technique may be termed "Anchored Periplasmic Expression" or "APEx." In some cases, a Gram-negative bacterial cell may be defined as an *E. coli* cell. Furthermore, in some aspects a Gram-negative bacterial cell may be defined as a genetically engineered bacterial cell, such as a Jude-1 strain of *E. coli*.

A fusion protein may comprise an N-terminal or C-terminal fusion with an Fc domain and in some case may comprise additional linker amino acids between the membrane anchoring polypeptide and the Fc domain. In certain specific cases, a membrane anchoring polypeptide may be the first six amino acids encoded by the *E. coli* NlpA gene, one or more transmembrane α-helices from an *E. coli* inner membrane protein, a gene III protein of filamentous phage or a fragment thereof, or an inner membrane lipoprotein or fragment thereof. Thus, as an example, a membrane anchoring polypeptide may be an inner membrane lipoprotein or fragment thereof such as from AraH, MglC, MalF, MalG, MalC, MalD, RbsC, RbsC, ArtM, ArtQ, GlnP, ProW, HisM, HisQ, LivH, LivM, LivA, LivE, DppB, DppC, OppB, AmiC, AmiD, BtuC, ThuD, FecC, FecD, FecR, FepD, NikB, NikC, CysT, CysW, UgpA, UgpE, PstA, PstC, PotB, PotC, PotH, Pod, ModB, NosY, PhnM, LacY, SecY, TolC, DsbB, DsbD, TouB, TatC, CheY, TraB, ExbD, ExbB, or Aas.

In still further cases, a population of Gram-negative bacteria according to the invention may be defined as comprising at least about $1 \times 10^3$, $1 \times 10^4$, $1 \times 10^5$, $1 \times 10^6$, $1 \times 10^7$, $1 \times 10^8$, $10 \times 10^9$ or more distinct antibodies Fc domains. In some specific cases, a population of Gram-negative bacterial cells may be produced by a method comprising the steps of: (a) preparing a plurality of nucleic acid sequences encoding a plurality of distinct antibody Fc domains; and (b) transforming a population of Gram-negative bacteria with said nucleic acids wherein the Gram-negative bacteria comprise a plurality of antibody Fc domains expressed in the periplasm.

B. Permeabilization of the Outer Membrane

Methods for disrupting, permeabilizing, or removing the outer membrane of bacteria are well known in the art, for example, see U.S. Pat. No. 7,094,571. For instance, prior to contacting the bacterial cells with an FcR polypeptide, the outer membrane of the bacterial cell may be treated with hyperosmotic conditions, physical stress, lysozyme, EDTA, a digestive enzyme, a chemical that disrupts the outer membrane, by infecting the bacterium with a phage, or a combination of the foregoing methods. Thus, in some cases, the outer membrane may be disrupted by lysozyme and EDTA treatment. Furthermore, in certain embodiments, the bacterial outer membrane may be removed entirely.

Methods may be employed for increasing the permeability of the outer membrane to one or more labeled ligands. This can allow screening access of labeled ligands otherwise unable to cross the outer membrane. However, certain classes of molecules, for example, hydrophobic antibiotics larger than the 650 Da exclusion limit, can diffuse through the bacterial outer membrane itself, independent of membrane porins (Farmer et al., 1999). The process may actually permeabilize the membrane on so doing (Jouenne and Junter, 1990). Also, certain long chain phosphate polymers (100 Pi) appear to bypass the normal molecular sieving activity of the outer membrane altogether (Rao and Torriani, 1988).

While conditions have been identified that lead to the permeation of ligands into the periplasm without loss of viability or release of the expressed proteins from the cells, the invention may be carried out without maintenance of the outer membrane. For Fc domains expressed or anchored in the periplasmic space, the need for maintenance of the outer membrane (as a barrier to prevent the leakage of the binding protein from the cell) to detect bound labeled ligand is removed. As a result, cells expressing binding proteins anchored to the outer (periplasmic) face of the cytoplasmic membrane can be labeled simply by incubating with a solution of labeled ligand in cells that either have a partially permeabilized membrane or a nearly completely removed outer membrane.

Treatments, such as hyperosmotic shock, can improve labeling significantly. It is known that many agents, including calcium ions (Bukau et al., 1985) and even Tris buffer (Irvin et al., 1981), alter the permeability of the outer-membrane. Further, phage infection stimulates the labeling process. Both the filamentous phage inner membrane protein pIII and the large multimeric outer membrane protein pIV can alter membrane permeability (Boeke et al., 1982) with mutants in pIV known to improve access to maltodextrins normally excluded (Marciano et al., 1999). Using the techniques of the invention, comprising a judicious combination of strain, salt, and phage, a high degree of permeability may be achieved (Daugherty et al., 1999). Cells comprising anchored or periplasm-associated polypeptides bound to labeled ligands can then be easily isolated from cells that express binding proteins without affinity for the labeled ligand using flow cytometry or other related techniques. However, in some cases, it will be desired to use less disruptive techniques in order to maintain the viability of cells. EDTA and lysozyme treatments may also be useful in this regard.

C. Labeled Target Ligands

As indicated above, it will typically be desired to provide an FcR polypeptide that has been labeled with one or more detectable agent(s). This can be carried out, for example, by linking the ligand to at least one detectable agent to form a conjugate. For example, it is conventional to link or covalently bind or complex at least one detectable molecule or moiety. A "label" or "detectable label" is a compound and/or element that can be detected due to specific functional properties, and/or chemical characteristics, the use of which allows the ligand to which it is attached to be detected, and/or further quantified if desired. Examples of labels that could be used include, but are not limited to, enzymes, radiolabels, haptens, fluorescent labels, phosphorescent molecules, chemiluminescent molecules, chromophores, luminescent molecules, photoaffinity molecules, colored particles, or ligands, such as biotin.

In one embodiment of the invention, a visually-detectable marker is used such that automated screening of cells for the label can be carried out. Examples of agents that may be detected by visualization with an appropriate instrument are known in the art, as are methods for their attachment to a desired ligand (see, e.g., U.S. Pat. Nos. 5,021,236; 4,938,948; and 4,472,509, each incorporated herein by reference). Such agents can include paramagnetic ions; radioactive isotopes; fluorochromes; NMR-detectable substances; and substances for X-ray imaging. In particular, fluorescent labels are beneficial in that they allow use of flow cytometry for isolation of cells expressing a desired binding protein or antibody.

Another type of FcR conjugate is where the ligand is linked to a secondary binding molecule and/or to an enzyme (an enzyme tag) that will generate a colored product upon contact with a chromogenic substrate. Examples of such enzymes include urease, alkaline phosphatase, (horseradish) hydrogen peroxidase, or glucose oxidase. In such instances, it will be desired that cells selected remain viable. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149; and 4,366,241, each incorporated herein by reference.

Molecules containing azido groups may be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide-binding proteins in crude cell extracts (Owens and Haley, 1987; Atherton et al., 1985). The 2- and 8-azido nucleotides have also been used to map nucleotide-binding domains of purified proteins (Khatoon et al., 1989; King et al., 1989; Dholakia et al., 1989) and may be used as ligand binding agents.

Labeling can be carried out by any of the techniques well known to those of skill in the art. For instance, FcR polypeptides can be labeled by contacting the ligand with the desired label and a chemical oxidizing agent, such as sodium hypochlorite, or an enzymatic oxidizing agent, such as lactoperoxidase. Similarly, a ligand exchange process could be used. Alternatively, direct labeling techniques may be used, e.g., by incubating the label, a reducing agent such as $SNCl_2$, a buffer solution such as sodium-potassium phthalate solution, and the ligand. Intermediary functional groups on the ligand could also be used, for example, to bind labels to a ligand in the presence of diethylenetriaminepentaacetic acid (DTPA) or ethylene diaminetetracetic acid (EDTA).

Other methods are also known in the art for the attachment or conjugation of a ligand to its conjugate moiety. Some attachment methods involve the use of an organic chelating agent, such as diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the ligand (U.S. Pat. Nos. 4,472,509 and 4,938,948, each incorporated herein by reference). FcR polypeptides also may be reacted with an enzyme in the presence of a coupling agent such as glutaraldehyde or periodate. Conjugates with fluorescein markers can be prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In still further aspects an FcR polypeptide may be fused to a reporter protein, such as an enzyme as described supra or a fluorescence protein.

D. Isolation of Bacterial Cells Bound to Labeled Target Ligand

1. Column- or Bead-Based Immobilization

The skilled artisan will understand that methods for selecting cells based upon their interaction (binding) with an FcR are well-known in the art. For example, an FcR may be immobilized on a column or bead (e.g., a magnetic bead) and the bacterial cell binding to the FcR separated by repeated washing of the bead (e.g., magnetic separation) or column. Furthermore, in some aspects a target ligand may be labeled, such as with a fluorophore, a radioisotope, or an enzyme. Thus, bacterial cells may, in some cases, be selected by detecting a label on a bound FcR. Furthermore, in some aspects, bacterial cells may be selected based on binding or lack of binding to two or more FcR polypeptides. For instance, bacteria may be selected that display antibodies that bind to two FcR polypeptides, wherein each FcR is used to select the bacteria sequentially. Conversely, in certain aspects, bacteria may be selected that display antibody Fc domains that bind to one FcR (such as an FcR comprising a first label) but not to a second FcR (e.g., comprising a second label). The foregoing method maybe used, for example, to identify antibody Fc domains that bind to a specific FcR but not a second specific FcR.

2. Flow Cytometry

In one embodiment of the invention, fluorescence activated cell sorting (FACS) screening or other automated flow cytometric techniques may be used for the efficient isolation of a bacterial cell comprising a labeled ligand bound to an Fc domain. Instruments for carrying out flow cytometry are known to those of skill in the art and are commercially available to the public. Examples of such instruments include FACS Star Plus, FACScan and FACSort instruments from Becton Dickinson (Foster City, Calif.), Epics C from Coulter Epics Division (Hialeah, Fla.), and MOFLO™ from Cytomation (Colorado Springs, Colo.).

Flow cytometric techniques in general involve the separation of cells or other particles in a liquid sample. Typically, the purpose of flow cytometry is to analyze the separated particles for one or more characteristics thereof, for example, presence of a labeled ligand or other molecule. The basic steps of flow cytometry involve the direction of a fluid sample through an apparatus such that a liquid stream passes through a sensing region. The particles should pass one at a time by the sensor and are categorized based on size, refraction, light scattering, opacity, roughness, shape, fluorescence, etc.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination that is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent-tagged antibodies, which are used to mark one or more cell types for separation.

Other examples of methods for flow cytometry include, but are not limited to, those described in U.S. Pat. Nos. 4,284,412; 4,989,977; 4,498,766; 5,478,722; 4,857,451; 4,774,189; 4,767,206; 4,714,682; 5,160,974; and 4,661,913, each of which are specifically incorporated herein by reference.

For the present invention, an important aspect of flow cytometry is that multiple rounds of screening can be carried out sequentially. Cells may be isolated from an initial round of sorting and immediately reintroduced into the flow cytometer and screened again to improve the stringency of the screen. Another advantage known to those of skill in the art is that nonviable cells can be recovered using flow cytometry. Since flow cytometry is essentially a particle sorting technology, the ability of a cell to grow or propagate is not necessary. Techniques for the recovery of nucleic acids from such non-viable cells are well known in the art and may include, for example, use of template-dependent amplification techniques including PCR.

E. Cloning of Fc Domain Coding Sequences

After a bacterial cell is identified that produces molecules of the desired specificity, affinity, and/or activity, the corresponding coding sequence may be cloned. In this manner, DNA encoding the molecule can be isolated and sequenced using conventional procedures (e.g., by using oligonucleotide probes that are capable of binding specifically to genes encoding the antibody or binding protein). It will be understood by those of skill in the art that nucleic acids may be cloned from viable or inviable cells. In the case of inviable cells, for example, it may be desired to use amplification of the cloned DNA, for example, using PCR. This may also be carried out using viable cells either with or without further growth of cells.

Once isolated, the antibody Fc domain DNA may be placed into expression vectors, which can then be transfected into host cells, such as bacteria. The DNA also may be modified, for example, by the addition of sequence for human heavy and light chain variable domains, or by covalently joining to the immunoglobulin coding sequence all or part of the coding sequence for a non-immunoglobulin polypeptide. In that manner, "chimeric" or "hybrid" binding proteins are prepared to have the desired binding specificity. For instance, an identified antibody Fc domain may be fused to a therapeutic polypeptide or a toxin and used to target cells (in vitro or in vivo) that express a particular FcR.

Chimeric or hybrid Fc domains also may be prepared in vitro using known methods in synthetic protein chemistry, including those involving crosslinking agents. For example, targeted-toxins may be constructed using a disulfide exchange reaction or by forming a thioether bond. Examples of suitable reagents for this purpose include iminothiolate and methyl-4-mercaptobutyrimidate.

V. Nucleic Acid-Based Expression Systems

Nucleic acid-based expression systems may find use, in certain embodiments of the invention, for the expression of recombinant proteins. For example, one embodiment of the invention involves transformation of Gram-negative bacteria with the coding sequences for an antibody Fc domain, or preferably a plurality of distinct Fc domains.

A. Methods of Nucleic Acid Delivery

Certain aspects of the invention may comprise delivery of nucleic acids to target cells (e.g., Gram-negative bacteria). For example, bacterial host cells may be transformed with nucleic acids encoding candidate Fc domains potentially capable binding an FcR. In particular embodiments of the invention, it may be desired to target the expression to the periplasm of the bacteria. Transformation of eukaryotic host cells may similarly find use in the expression of various candidate molecules identified as capable of binding a target ligand.

Suitable methods for nucleic acid delivery for transformation of a cell are believed to include virtually any method by which a nucleic acid (e.g., DNA) can be introduced into a cell, or even an organelle thereof. Such methods include, but are not limited to, direct delivery of DNA, such as by injection (U.S. Pat. Nos. 5,994,624; 5,981,274; 5,945,100; 5,780,448; 5,736,524; 5,702,932; 5,656,610; 5,589,466; and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Publn. Nos. WO 94/09699 and 95/06128; U.S. Pat. Nos. 5,610,042; 5,322,783; 5,563,055; 5,550,318; 5,538,877; and 5,538,880, and each incorporated herein by reference); or by agitation with silicon carbide fibers (Kaeppler et al., 1990; U.S. Pat. Nos. 5,302,523 and 5,464,765, each incorporated herein by reference); by desiccation/inhibition-mediated DNA uptake (Potrykus et al., 1985). Through the application of techniques such as these, cells may be stably or transiently transformed.

B. Vectors

Vectors may find use with the current invention, for example, in the transformation of a cell with a nucleic acid sequence encoding a candidate Fc domain. In one embodiment of the invention, an entire heterogeneous "library" of nucleic acid sequences encoding polypeptides may be introduced into a population of cells, thereby allowing screening of the entire library. The term "vector" is used to refer to a carrier nucleic acid molecule into which a nucleic acid sequence can be inserted for introduction into a cell where it can be replicated. A nucleic acid sequence can be "exogenous" or "heterologous," which means that it is foreign to the cell into which the vector is being introduced or that the sequence is homologous to a sequence in the cell but in a position within the host cell nucleic acid in which the sequence is ordinarily not found. Vectors include plasmids, cosmids, and viruses (e.g., bacteriophage). One of skill in the art may construct a vector through standard recombinant techniques, which are described in Maniatis et al., 1988 and Ausubel et al., 1994, both of which are incorporated herein by reference.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well.

1. Promoters and Enhancers

A "promoter" is a control sequence that is a region of a nucleic acid sequence at which initiation and rate of transcription are controlled. It may contain genetic elements to which regulatory proteins and molecules may bind, such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. Those of skill in the art of molecular biology generally are familiar with the use of promoters, enhancers, and cell type combinations for protein expression, for example, see Sambrook et al. (1989), incorporated herein by reference.

2. Initiation Signals

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs prepared in accordance with the present invention will generally comprise at least one termination signal. A "termination signal" or "terminator" is comprised of the DNA sequences involved in specific termination of an RNA transcript by an RNA polymerase. Thus, in certain embodiments, a termination signal that ends the production of an RNA transcript is contemplated. A terminator may be necessary in vivo to achieve desirable message levels. Terminators contemplated for use in the invention include any known terminator of transcription known to one of ordinary skill in the art, including, but not limited to, rho dependent or rho independent terminators. In certain embodiments, the termination signal may be a lack of transcribable or translatable sequence, such as due to a sequence truncation.

5. Origins of Replication

In order to propagate a vector in a host cell, it may contain one or more origins of replication sites (often termed "ori"), which is a specific nucleic acid sequence at which replication is initiated.

6. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers, such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

C. Host Cells

In the context of expressing a heterologous nucleic acid sequence, "host cell" refers to a prokaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

In particular embodiments of the invention, a host cell is a Gram-negative bacterial cell. These bacteria are suited for use with the invention in that they possess a periplasmic space between the inner and outer membrane and, particularly, the aforementioned inner membrane between the periplasm and cytoplasm, which is also known as the cytoplasmic membrane. As such, any other cell with such a periplasmic space could be used in accordance with the invention. Examples of Gram-negative bacteria that may find use with the invention may include, but are not limited to, *E. coli, Pseudomonas aeruginosa, Vibrio cholera, Salmonella typhimurium, Shigella flexneri, Haemophilus influenza, Bordotella pertussi, Erwinia amylovora, Rhizobium* sp.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5a, JM109, and KC8, as well as a number of commercially available bacterial hosts such as SURE® Competent Cells and SOLOPACK™ Gold Cells (Stratagene®, La Jolla). Alternatively, bacterial cells such as *E. coli* LE392 could be used as host cells for bacteriophage.

Examples of mammalian host cells include Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658). The foregoing being illustrative but not limitative of the many possible host organisms known in the art.

Mammalian host cells expressing the polypeptide are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

Many host cells from various cell types and organisms are available and would be known to one of skill in the art. Similarly, a viral vector may be used in conjunction with a prokaryotic host cell, particularly one that is permissive for replication or expression of the vector. Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

D. Expression Systems

Numerous expression systems exist that comprise at least a part or all of the compositions discussed above. Such systems could be used, for example, for the production of a polypeptide product identified in accordance with the invention as capable of binding a particular ligand. Prokaryote-based systems can be employed for use with the present invention to produce nucleic acid sequences, or their cognate polypeptides, proteins, and peptides. Many such systems are commercially and widely available. Other examples of expression systems comprise of vectors containing a strong prokaryotic promoter such as T7, Tac, Trc, BAD, lambda pL, Tetracycline or Lac promoters, the pET Expression System, and an *E. coli* expression system.

In certain aspects of the invention, nucleic acid sequences encoding a polypeptide are disclosed. Depending on which expression system is used, nucleic acid sequences can be selected based on conventional methods. For example, if the polypeptide is derived from a human polypeptide and contains multiple codons that are rarely utilized in *E. coli*, then that may interfere with expression in *E. coli*. Therefore, the respective genes or variants thereof may be codon optimized for *E. coli* expression. Various vectors may be also used to express the protein of interest. Exemplary vectors include, but are not limited, plasmid vectors, viral vectors, transposon, or liposome-based vectors.

VI. Protein Purification

Protein purification techniques are well known to those of skill in the art. These techniques involve, at one level, the homogenization and crude fractionation of the cells, tissue, or organ into polypeptide and non-polypeptide fractions.

The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, size-exclusion chromatography, reverse phase chromatography, hydroxyapatite chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC). As is generally known in the art, it is believed that the order of conducting the various purification steps may be changed, or that certain steps may be omitted, and still result in a suitable method for the preparation of a substantially purified protein or peptide.

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size-exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase. The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

VII. Pharmaceutical Compositions

Where clinical application of a pharmaceutical composition containing a polypeptide or antibody is undertaken, it will generally be beneficial to prepare a pharmaceutical or therapeutic composition appropriate for the intended application. Generally, pharmaceutical compositions may comprise an effective amount of one or more polypeptide or additional agents dissolved or dispersed in a pharmaceutically acceptable carrier. In certain embodiments, pharmaceutical compositions may comprise, for example, at least about 0.1% of a polypeptide or antibody. In other embodiments, a polypeptide or antibody may comprise between about 2% to about 75% of the weight of the unit, or between about 25% to about 60%, for example, and any range derivable therein. The amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by FDA Office of Biological Standards.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Examples of carriers or diluents include fats, oils, water, saline solutions, lipids, liposomes, resins, binders, fillers, and the like, or combinations thereof. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, antioxidants, preservatives (e.g., antibacterial or antifungal agents, antioxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present invention, the composition is combined with the carrier in any convenient and practical manner, i.e., by solution, suspension, emulsification, admixture, encapsulation, absorption, grinding, and the like. Such procedures are routine for those skilled in the art.

Certain embodiments of the present invention may comprise different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). Typically, such compositions can be prepared as either liquid solutions or suspensions; solid forms suitable for use to prepare solutions or suspensions upon the addition of a liquid prior to injection can also be prepared; and, the preparations can also be emulsified.

The polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine.

In further embodiments, the present invention may concern the use of a pharmaceutical lipid vehicle composition that includes polypeptides, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the polypeptide or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects. The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

VIII. Methods of Treating

Certain aspects of the present invention provide a polypeptide for treating diseases, such as tumors. Particularly, the polypeptide may have human polypeptide sequences and thus may prevent allergic reactions in human patients, allow repeated dosing, and increase the therapeutic efficacy.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an antibody that targets CDC to cancer cells without triggering cancer cell proliferation.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary;

acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The polypeptide may be used herein as an antitumor agent in a variety of modalities for triggering complement activation in tumor tissue or for triggering complement activation where it is considered desirable. In a particular embodiment, the invention contemplates methods of using a polypeptide as an antitumor agent, and therefore comprises contacting a population of tumor cells with a therapeutically effective amount of a polypeptide for a time period sufficient to inhibit tumor cell growth.

In one embodiment, the contacting in vivo is accomplished by administering, by intravenous intraperitoneal, or intratumoral injection, a therapeutically effective amount of a physiologically tolerable composition comprising a polypeptide of this invention to a patient. The polypeptide can be administered parenterally by injection or by gradual infusion over time. The polypeptide can be administered intravenously, intraperitoneally, orally, intramuscularly, subcutaneously, intracavity, transdermally, dermally, can be delivered by peristaltic means, or can be injected directly into the tissue containing the tumor cells.

Therapeutic compositions comprising polypeptides are conventionally administered intravenously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial and booster administration are also contemplated and are typified by an initial administration followed by repeated doses at one or more hour intervals by a subsequent injection or other administration. Exemplary multiple administrations are described herein and are particularly preferred to maintain continuously high serum and tissue levels of polypeptide. Alternatively, continuous intravenous infusion sufficient to maintain concentrations in the blood in the ranges specified for in vivo therapies are contemplated.

It is contemplated that a polypeptide of the invention can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

A therapeutically effective amount of a polypeptide is a predetermined amount calculated to achieve the desired effect, i.e., to trigger CDC in the tumor tissue, and thereby mediate a tumor-ablating pro-inflammatory response. Thus, the dosage ranges for the administration of polypeptide of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

IX. Combination Therapy

In certain embodiments, the compositions and methods of the present embodiments involve administration of a polypeptide or antibody in combination with a second or additional therapy. Such therapy can be applied in the treatment of any disease that is responsive to CDC. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a polypeptide or antibody and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a polypeptide or an anticancer agent), or by exposing the tissue, tumor, and/or cell with two or more distinct compositions or formulations, wherein one composition provides 1) a polypeptide or antibody, 2) an anti-cancer agent, or 3) both a polypeptide or antibody and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic polypeptide or antibody and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A polypeptide or antibody may be administered before, during, after, or in various combinations relative to an anti-cancer treatment. The administrations may be in intervals ranging from concurrently to minutes to days to weeks. In embodiments where the polypeptide or antibody is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the polypeptide and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a polypeptide or antibody is "A" and an anti-cancer therapy is "B":

Administration of any polypeptide or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaII); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine;

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | | androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. Checkpoint inhibitors, such as, for example, ipilumimab, are another such example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p9'7), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

X. Kits

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a polypeptide, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes a polypeptide that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

XI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—the Strategy of Libraries for Engineering Fc Domain

*E. coli* does not encode protein glycosylation machinery and therefore the Fc domains of IgG expressed in the periplasm of *E. coli* are aglycosylated, lacking the glycan that is normally appended to N297 of the Fc domain. Aglycosylated Fc domains display a greater degree of conformational flexibility that results in highly attenuated or no detectable binding to effector FcγRs (FcγRIA, FcγRIIA, FcγRIIB, FcγRIIc, FcγRIIIA, FcγRIIIB) and C1q (Jefferis et al., 2005; Borrok et al., 2012). To isolate aglycosylated Fc domain variants containing mutations that enable binding to C1q despite the absence of the N297 glycan, three different libraries were constructed. In the first library (S-library), random amino acids were introduced at Glu231, Leu232, Leu233, Gly234, Gly235, Ile334, Ser335, Lys336, Ala337, Lys338, Gly339, Gln340, Pro341, Arg342, and Glu343 using spiked oligonucleotides with codons for conserving wild-type amino acid sequences of around 50% (Lanio et al., 1998). In order to introduce these random 15 amino acids, eight primers (SEQ ID NOs: 24-31) were designed (Table 15). The second library (SE-library) has additional random mutants based on S-library using error-prone PCR (Fromant et al., 1995). In order to introduce additional random mutation into the CH2 domain of the S-library, the two primers PCH018 (SEQ ID NO: 26) and PCH023 (SEQ ID NO: 31) were designed. In order to construct third library (E-library), standard error-prone PCR was employed using a wild-type Fc template and two primers PCH018 (SEQ ID NO: 26) and PCH021 (SEQ ID NO: 29).

Example 2—the Construction of Libraries for Engineering Fc Domain

Figure 1B:
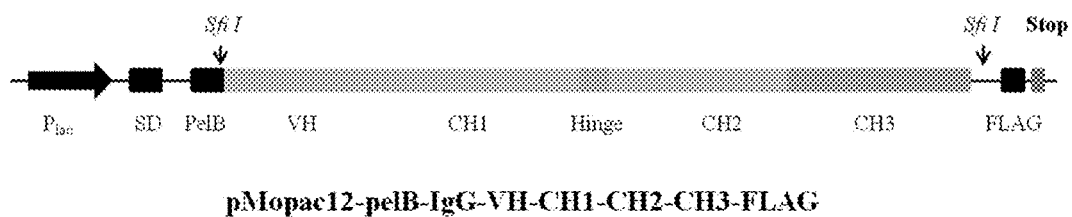
Figure 2:
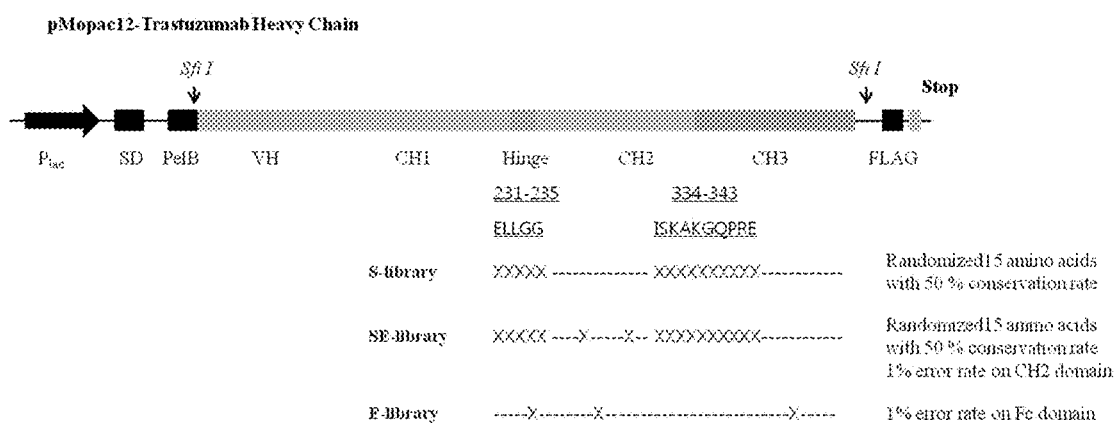
FIG. 2. Brief scheme of the specific strategies for constructing libraries of mutated Fc polypeptides.

All plasmids and primers are described in Tables 10 and 11. All primers were synthesized by Integrated DNA Technologies. IgG polypeptides were displayed on the inner membrane of *E. coli* using two vectors: pBAD30-PelB-VL-Ck-NlpA-VL-Ck-His-cMyc and pMopac12-pelB-IgG-VH-CH1-CH2-CH3-FLAG (Jung et al., 2012) (FIG. 1). In order to construct the S-library, the eight primers (SEQ ID NOs: 24-31) were used (Table 15 and FIG. 2). Two specific primers (PCH017 and PCH020; SEQ ID NOs: 25 and 28, respectively) among the eight primers contain degenerate codons using the spiked oligonucleotides to conserve wild-type amino acids sequences with approximately 50% possibility. The three fragments of the heavy chain gene of IgG1 were amplified with the eight primers and overlapped with PCH016 (SEQ ID NO: 24) and PCH021 (SEQ ID NO: 29) (S-library, Table 15 and FIG. 2). For another sub-library, standard error-prone PCR was employed on CH2 domain with Fc library genes from the S-library with PCH018 (SEQ ID NO: 26) and PCH023 (SEQ ID NO: 31) (SE-library). As a result, the SE-library contains 15 random amino acids as were generated during S-library construction and an additional 1% random mutations in the CH2 domain. For the E-library, standard error-prone PCR was employed on Fc domain with a wild-type Fc gene with PCH018 (SEQ ID NO: 26) and PCH021 (SEQ ID NO: 29). The three amplified heavy chain library genes were ligated in frame into a SfiI digested bacterial display vector, pMopac12-pelB-IgG-VH-CH1-CH2-CH3-FLAG. The resulting plasmids were transformed into *E. coli* JUDE-1-pBAD30-PelB-VL-Ck-NlpA-VL-Ck-His-cMyc. (Jung et al., 2010; Jung et al., 2012) The sizes of sub-libraries were $2 \times 10^8$ (S-library), $3 \times 10^8$ (SE-library), and $1 \times 10^9$ (E-library).

Example 3—the Preparation of C1q, Dimeric FcγRs, Tetrameric FcγR, and Dimeric FcRn The C1q protein from human serum was purchased from Abcam. Plasmids for mammalian expression of Fc receptors were constructed as described previously (Jung et al., 2012). FcγRI-His, FcγRIIa-$_{H131}$-GST, FcγRIIa-$_{R131}$-GST, FcγRIIb-GST, FcγRIIIa-$_{V158}$-GST, FcγRIIIa-$_{F158}$-GST, and FcγRIIIa-$_{V158}$-Streptavidin (FcγRIIIa-$_{V158}$-SA), and FcRn-GST were produced by transient transfection of HEK293F cells (Invitrogen) using the pMAZ-IgH (U.S. Pat. No. 8,043,621) derived expression vectors described in Table 16. The transfected HEK293F cells were cultured for 5 days in a 5% CO$_2$ incubator at 37° C. The supernatant was collected by centrifugation at 4,000×g for 10 min and filtered by 0.22 μm polyethersulfone (PES) membrane filter (PALL). The FcγRI-His was purified with Ni-NTA (GE Healthcare) affinity columns according to the manufacturer's instructions. The Fc receptors-GST fusion proteins were purified with Glutathione Sepharose (GE Healthcare) affinity columns according to the manufacturer's instructions. The FcγRIIIa-$_{V158}$-SA was purified with Strep-Tactin (IBA-Life Science, Germany) affinity columns according to the manufacturer's instructions. To remove lipopolysaccharide (LPS) and non-specifically bound protein, the FcγRs-bound resins were washed with 50 mL of PBS containing 0.1% Triton® X-114 (Sigma-Aldrich) and 50 mL of PBS. The FcγRI-His was eluted with PBS containing 250 mM imidazole, the Fc receptors-GST were eluted with PBS containing 10 mM reduced L-glutathione, and FcγRIIIa$_{V158}$-SA was eluted with elution buffer (pH 8.0, 100 mM Tris-HCl, 150 mM NaCl, 2.5 mM desthiobiotin, and 1 mM EDTA). The buffer of all eluted Fc receptors was exchanged to PBS by Amicon Ultra-4 (Millipore). The human C1q (Abcam) or purified FcγRIIIa$_{V158}$-SA was labeled with R-phycoerythrin (R-PE) using an EasyLink R-PE Conjugation Kit (Abcam) according to the manufacturer's instructions.

Example 4—Screening of Fc Libraries for C1q Binding

E. coli JUDE-1 were cultured overnight at 37° C. and 250 rpm in Terrific Broth (TB) with chloramphenicol (40 µg/mL) and kanamycin (50 µg/mL). Following overnight growth, cells were diluted 1:50 in fresh 100 mL TB media with two antibiotics. E. coli JUDE-1 cells were cultured at 37° C. and 250 rpm until OD$_{600}$ reached a value of approximately 0.4. Then, 1 mM isopropyl-β-D-thiogalactopyranoside (IPTG, Sigma Aldrich) and 2% L-arabinose (Sigma-Aldrich) were added to the E. coli JUDE-1 cells to facilitate the protein expression, and the E. coli JUDE-1 cells were then further incubated at 25° C. for 20 h. E. coli JUDE-1 cells (8 mL) were harvested by centrifugation and washed two times in 1 mL of ice-chilled 10 mM Tris-HCl (pH 8.0). The washed cells were resuspended in 1 mL of ice-chilled STE solution (0.5 M sucrose, 10 mM Tris-HCl, 10 mM EDTA, pH 8.0) and incubated at 37° C. for 30 min. The cells were centrifuged at 13,000 rpm for 1 min and washed with 1 mL of Solution A (0.5 M sucrose, 20 mM MgCl$_2$, 10 mM MOPS, pH 6.8). The washed cells were incubated in 1 mL of Solution A with 1 mg/mL hen egg lysozyme (Sigma-Aldrich) at 37° C. for 15 min. After centrifugation at 13,000 rpm for 1 min, the pelleted spheroplasts were resuspended in 1 mL of cold PBS (Jung et al., 2010; Jung et al., 2012).

In order to determine the optimal concentration of target protein for screening, the spheroplasts were labeled with 10 nM human C1q-PE or 10 nM FcγRIIIa$_{V158}$-SA-PE. As a control, PA domain 4-expressing spheroplasts (Leysath et al., 2009) were incubated with the high affinity, glycosylated anti-PA antibody M18. Spheroplasts that bound the control glycosylated M18 IgG showed extremely high signals following labeling with C1q relative to non-labeled control spheroplasts (FIG. 3A; Table 3).

C1q has the ability to bind lipopolysaccharide (LPS), which is expressed on the outer membrane of E. coli (Zohair et al., 1989). As expected, LPS was detected in all spheroplasts by anti-LPS IgG-PE (Abcam) (FIG. 3B; Table 3). To eliminate background binding of C1q on LPS, several different buffers were tested, and high salt (50 mM phosphate, 330 mM NaCl, pH 7.4) was found to inhibit the interaction between C1q-PE and LPS. IgG displays normal binding for C1q under this high salt buffer condition (FIG. 3C; Table 3). Next, the FcγRIIIA$_{V158}$-SA-PE binding ability of spheroplasts displaying aglycosylated IgG from the three Fc libraries or glycosylated M18 IgG were examined. Under labeling conditions with 10 nM FcγRIIIA$_{V158}$-SA-PE, spheroplasts displaying glycosylated M18 IgG showed binding signals but those displaying aglycosylated IgG or the three Fc libraries did not (FIG. 3D; Table 3).

TABLE 3

FACS analysis for confirming of labeling condition with C1q or FcγRIIIa (data correspond to FIGS. 3A-D)

Figure 3A:
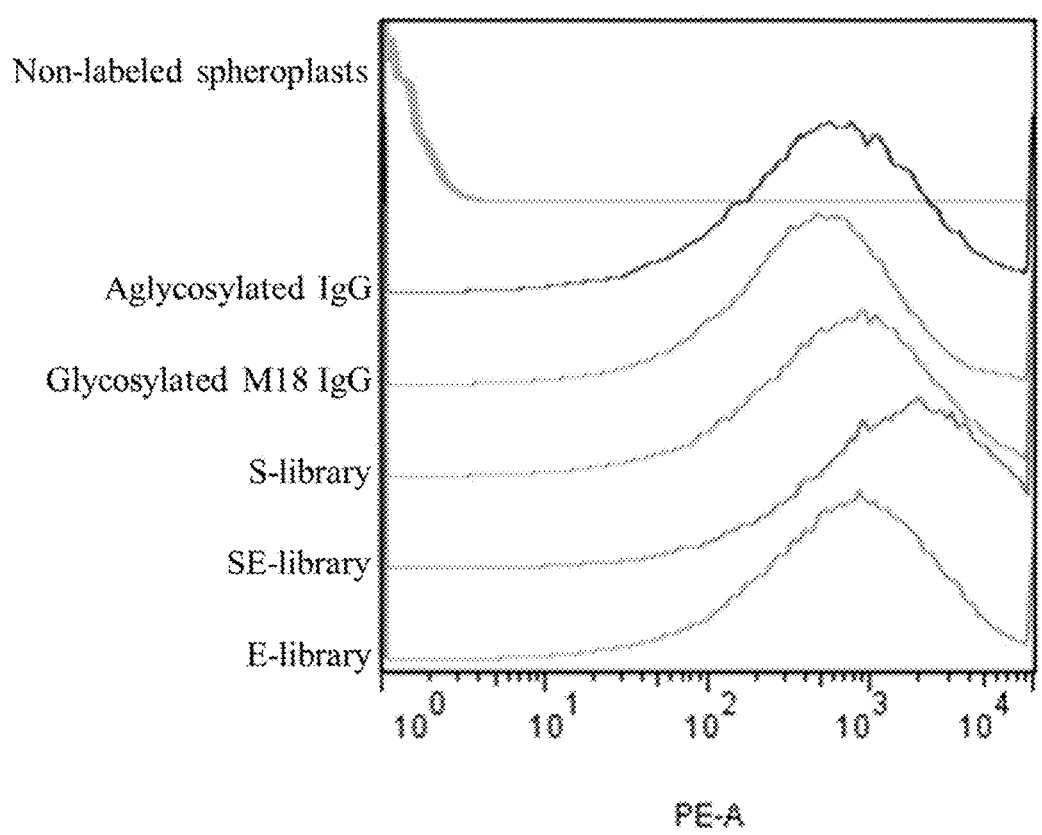
FIGS. 3A-D. FACS analysis for confirmation of labeling condition with C1q or FcγRIIIa.
Figure 3B:
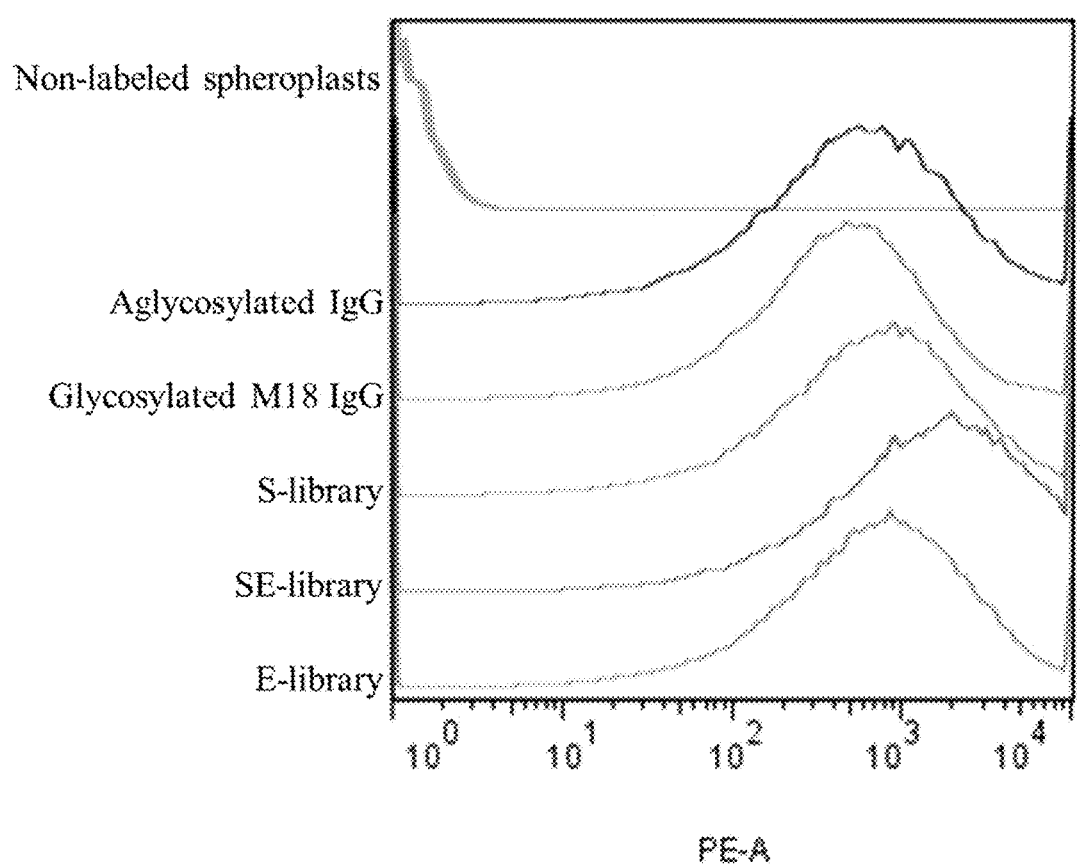
Figure 3C:
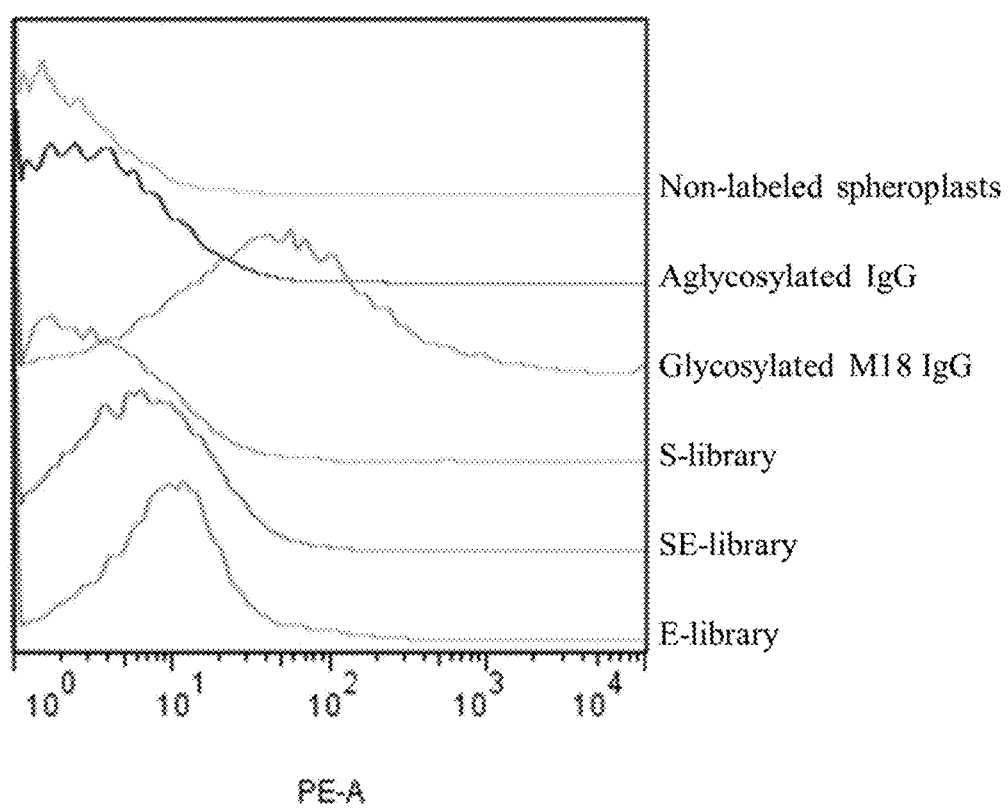
Figure 3D:
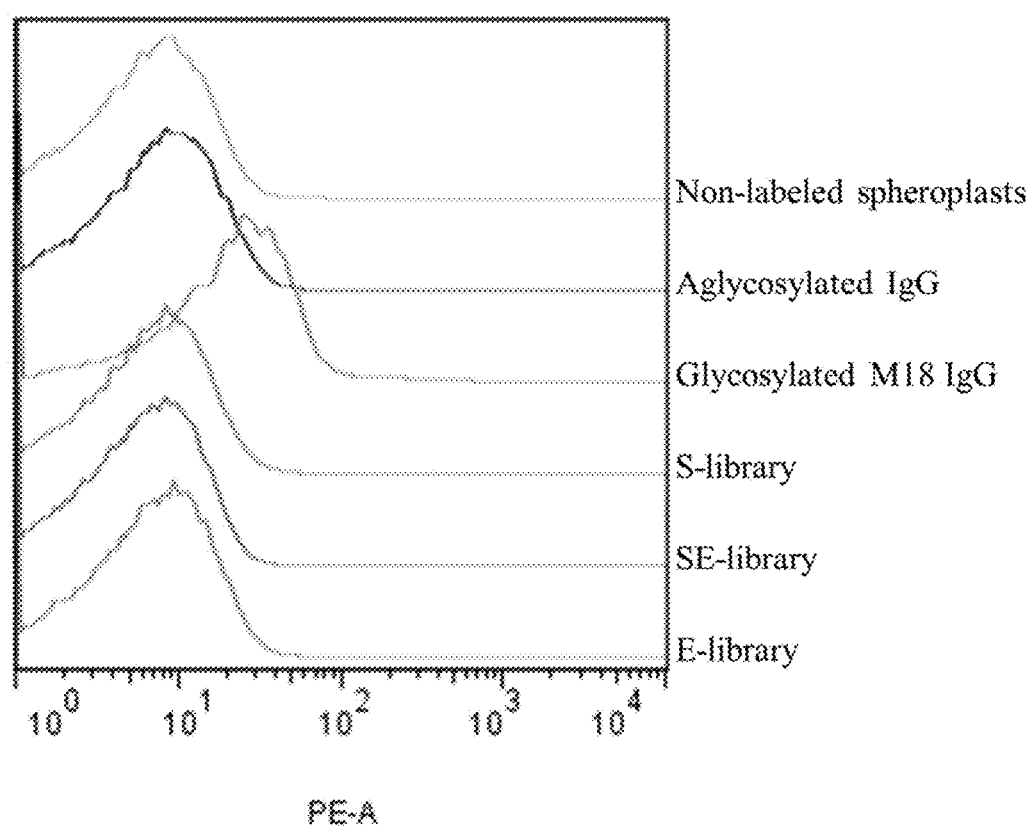

| | Mean Fluorescence Intensity (MFI) | | | |
| --- | --- | --- | --- | --- |
| | FIG. 3A | FIG. 3B | FIG. 3C | FIG. 3D |
| Non-labeled spheroplasts | 1.03 | 1.88 | 3.35 | 5.40 |
| Aglycosylated IgG | 1084 | 114 | 14.9 | 6.44 |
| Glycosylated M18 IgG | 817 | 144 | 105 | 25.1 |
| S-library | 1172 | 134 | 14.3 | 5.93 |
| SE-library | 2417 | 134 | 12.7 | 4.63 |
| E-library | 1184 | 217 | 16.0 | 5.62 |

Figure 4A:
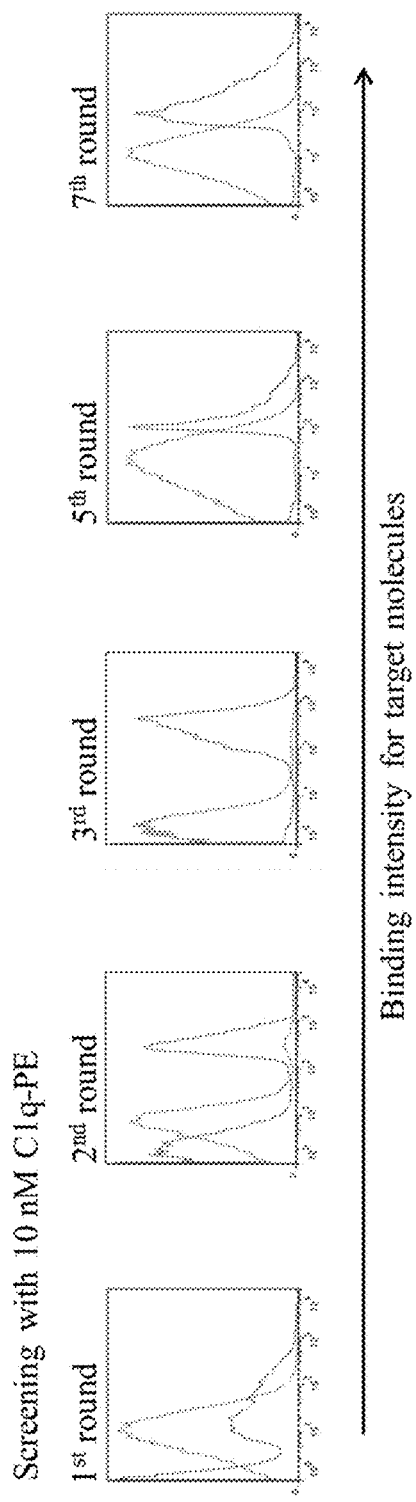
FIGS. 4A-B. FACS analysis histograms showing enrichment of high affinity clones binding to C1q following Fc library sorting and resorting.
Figure 4B:
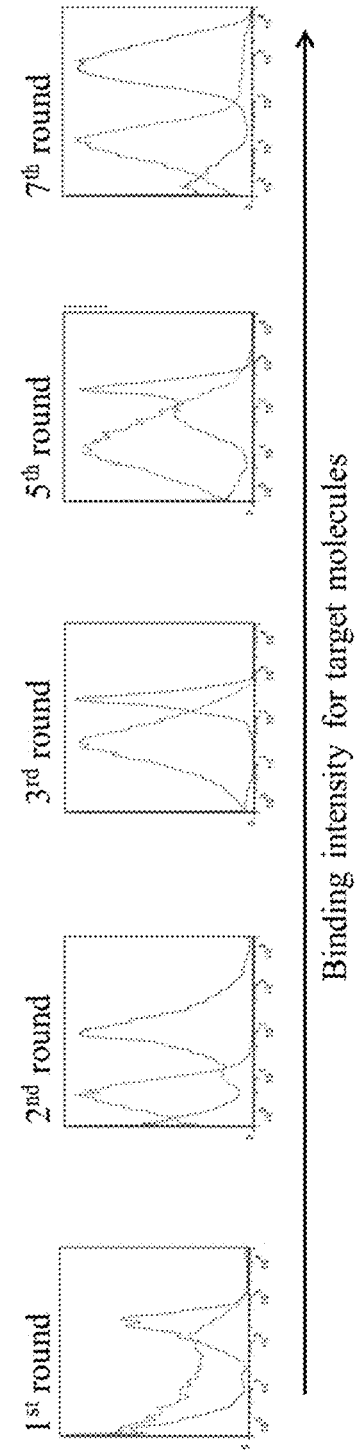

To isolate C1q-specific aglycosylated IgG variants, cells expressing the three sub-libraries described in Examples 1 and 2 were labeled with 10 nM C1q-PE in the presence of 1 µM FcγRs as a competitor and screening on a FACSAria™ (BD Biosciences). In each round, the top 1% of the population showing the highest fluorescence was recovered and these spheroplasts were resorted immediately to remove false positives. The heavy chain genes in the sorted spheroplasts were rescued by PCR using two primers (PCH16 and PCH21) after boiling for 5 min and ligated into SfiI-cut pMopac12 vector. The ligated plasmids were transformed in E. coli JUDE-1 cells. The transformants were selected on chloramphenicol- and kanamycin-containing media and the spheroplasts were prepared for the next round screens. Seven rounds of screening were carried out with 10 nM C1q-PE (FIG. 4A). To isolate C1q- and FcγRIIIa-binding IgG variants, the three sub-libraries were screened sequentially with 10 nM C1q-PE or 10 nM FcγRIIIa$_{V158}$-SA-PE with the same methods. The first, third, fifth, and seventh rounds of screening were undertaken with 10 nM C1q-PE, and the second, fourth, and sixth rounds of screening were undertaken with 10 nM FcγRIIIa$_{V158}$-SA-PE (FIG. 4B).

Figure 5:
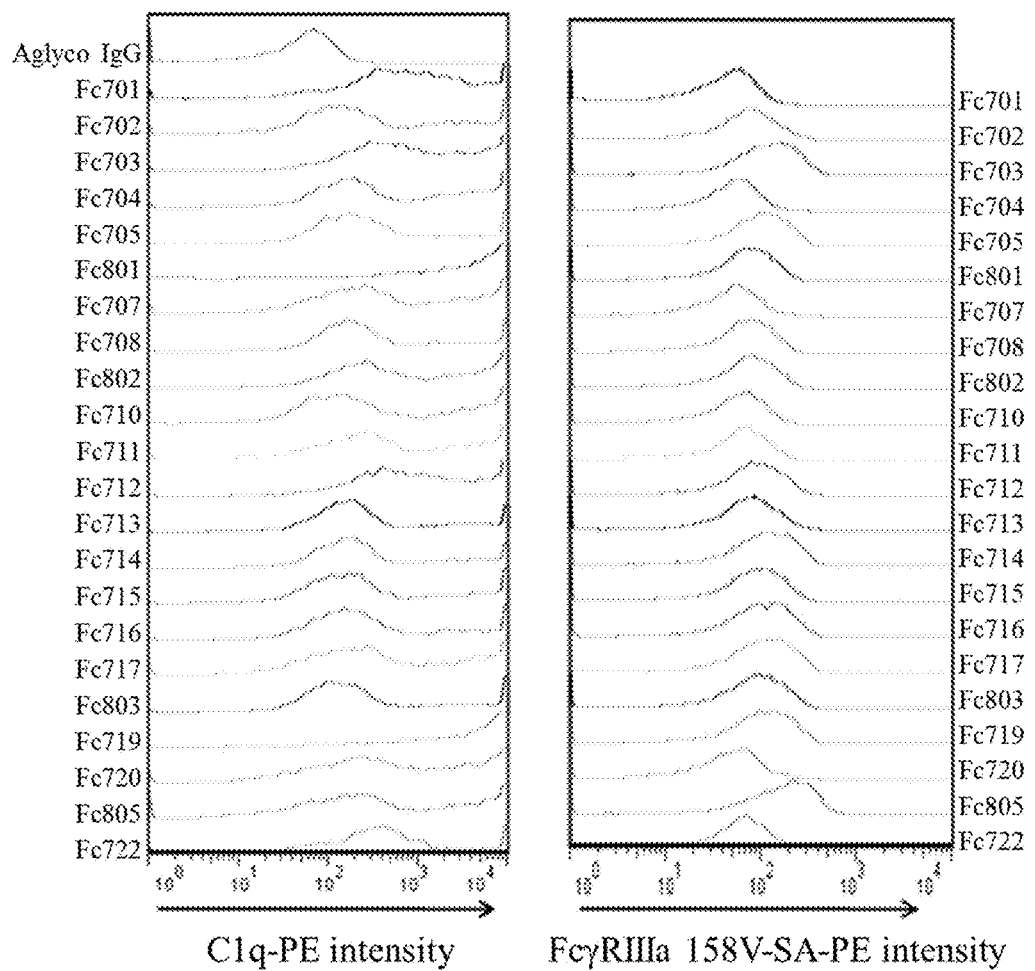
FIG. 5. Binding analysis of the 22 isolated IgG variants with C1q-PE or FcγRIIIa-SA-PE using FACS. Left histogram shows C1q binding intensities of the isolated IgG variants for C1q. Right histogram shows FcγRIIIa-SA-PE binding intensities of the isolated IgG variants for FcγRIIIa-SA-PE. Mean fluorescence intensities are listed in Table 4.

Example 5—FACS Analysis of IgG Variants 12 randomly selected IgG variants from the last round of sorting from the libraries screened with C1q-PE were sequenced (SEQ ID NOs: 2-13). Similarly, 10 randomly selected IgG variants from the libraries screened with C1q-PE and FcγRIIIa$_{V158}$-SA-PE were sequenced (SEQ ID NOs: 14-23). The respective genes were transformed in E. coli JUDE-1 cells, which were spheroplasted and analyzed with 10 nM C1q-PE and 10 nM FcγRIIIa$_{V158}$-SA-PE by FACS. As shown in FIG. 5 and Table 4, all 22 IgG variants showed 24-113 fold higher mean fluorescence intensity (MFI) values relative to wild-type aglycosylated IgG for C1q. In particular, Fc801, Fc802, and Fc803 showed 113.1, 56.5, and 92.8 fold increased MFI values, respectively, relative to wild-type aglycosylated IgG for C1q. Further, these three IgG clones showed relatively similar MFI values for 10 nM FcγRIIIa$_{V158}$-SA-PE with aglycosylated IgG, which does not have affinity for FcγRIIIa. Additionally, Fc702, Fc713, Fc720, and Fc805 showed 3.4, 3.2, 4, and 4.8 fold enhanced MFI values, respectively, relative to wild-type aglycosylated IgG when labeled with 10 nM FcγRIIIa$_{V158}$-SA-PE, and 24.6-48.6 fold enhanced MFI values relative to wild-type aglycosylated IgG for C1q-PE (FIG. 5). Fc801 and Fc802 were selected for further study. Fc801 has two mutations of K320E and Q386R; Fc802 has four mutations of L235K, G236M, G237R, and L351Q. As a binder for C1q and FcγRIIIa, Fc805 was selected, and found to have eight mutations of V308A, S337P, K338Q, K340R, Q342P, R344G, E345Y, and F372L.

TABLE 4

Binding analysis of the isolated twenty two IgG variants with C1q-PE or FcγRIIIa-SA-PE using FACS (data correspond to FIG. 5)

| | C1q-PE | | FcγRIIIa 158V-SA-PE | |
|---|---|---|---|---|
| | MFI | Increasing Fold | MFI | Increasing Fold |
| Aglyco IgG | 54.7 | 1 | 36.6 | 1 |
| Fc701 | 2011 | 36.76 | 81.8 | 2.23 |
| Fc702 | 1545 | 28.24 | 123 | 3.36 |
| Fc703 | 2629 | 48.06 | 51 | 1.39 |
| Fc704 | 2362 | 43.18 | 99.5 | 2.72 |
| Fc705 | 1456 | 26.62 | 72.4 | 1.98 |
| Fc801 | 6186 | 113.09 | 57.7 | 1.58 |
| Fc707 | 2447 | 44.73 | 73.5 | 2.01 |
| Fc708 | 1478 | 27.02 | 77.2 | 2.11 |
| Fc802 | 3091 | 56.51 | 57.5 | 1.57 |
| Fc710 | 2680 | 48.99 | 65.5 | 1.79 |
| Fc711 | 2251 | 41.15 | 90.3 | 2.47 |
| Fc712 | 2521 | 46.09 | 86.7 | 2.37 |
| Fc713 | 1345 | 24.59 | 116 | 3.17 |
| Fc714 | 1396 | 25.52 | 89.2 | 2.44 |
| Fc715 | 1699 | 31.06 | 107 | 2.92 |
| Fc716 | 1444 | 26.4 | 111 | 3.03 |
| Fc717 | 2153 | 39.36 | 90.7 | 2.48 |
| Fc719 | 1430 | 26.14 | 107 | 2.92 |
| Fc803 | 5078 | 92.83 | 54.5 | 1.49 |
| Fc720 | 2657 | 48.57 | 145 | 3.96 |
| Fc805 | 2170 | 39.67 | 175 | 4.78 |
| Fc722 | 1308 | 23.91 | 64.8 | 1.77 |

Example 6—Expression and Purification of the Selected IgG Variants

Figure 6A:
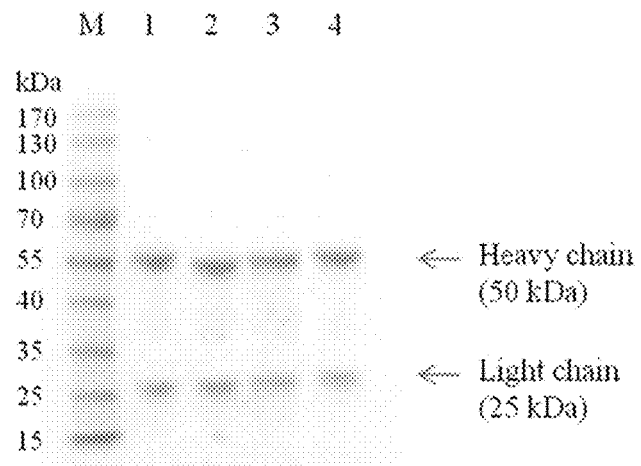
FIGS. 6A-B. SDS-PAGE analysis under reducing (FIG. 6A) or non-reducing (FIG. 6B) conditions, after purifying the wild-type IgG, Rituximab, and the selected IgG variants RAI (anti-CD20 Rituximab Fab and aglycosylated Fc802), RAII (anti-CD20 Rituximab Fab and aglycosylated Fc801), and RAIII (anti-CD20 Rituximab Fab and aglycosylated Fc805). M: Protein size marker; 1: Rituximab; 2: RAI; 3: RAII 3: RAIII FIG. 7. Size exclusion chromatography (SEC) analysis to confirm that the purified IgG variants were present as a monomer in solution.
Figure 6B:
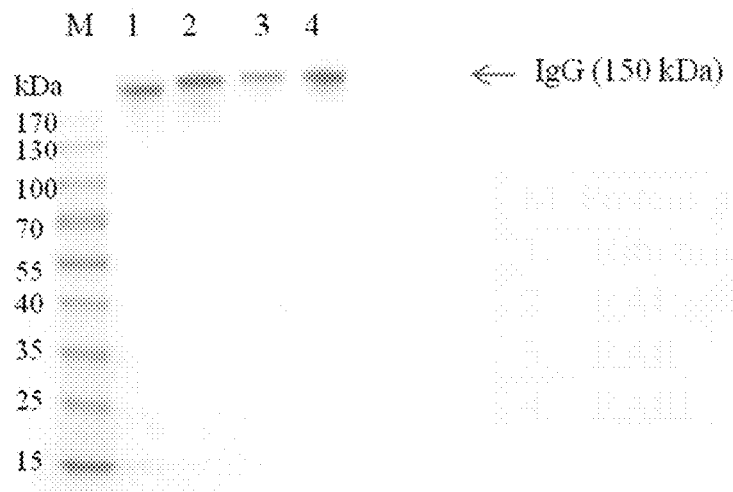
Figure 7:
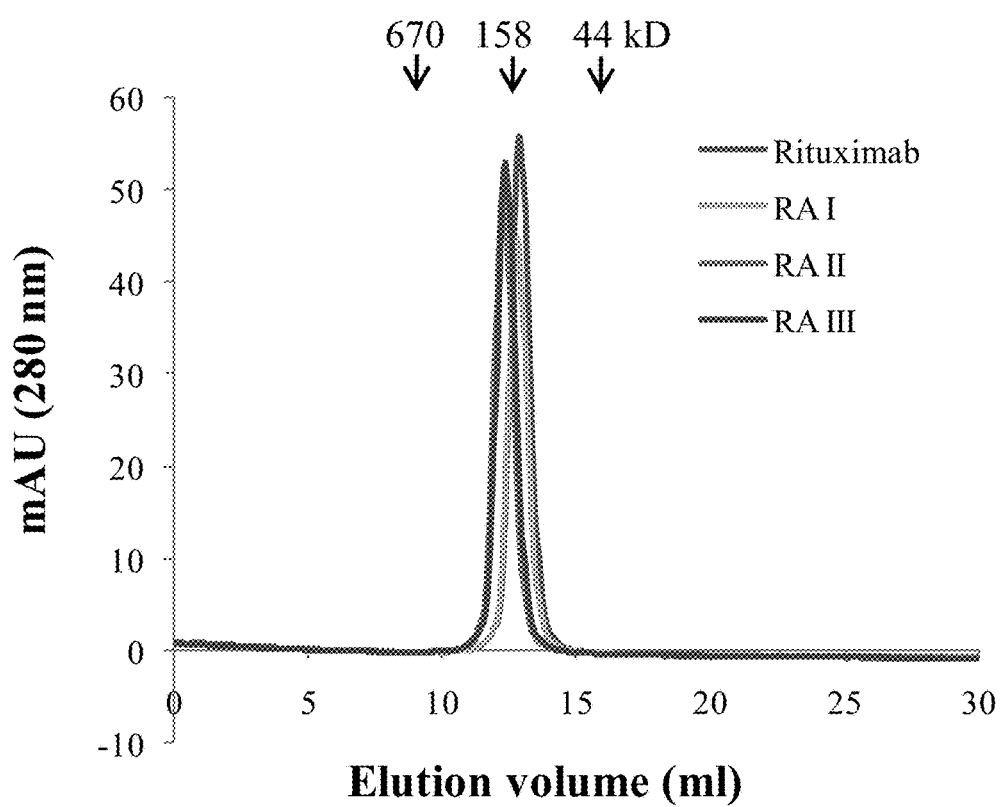
Figure 8A:
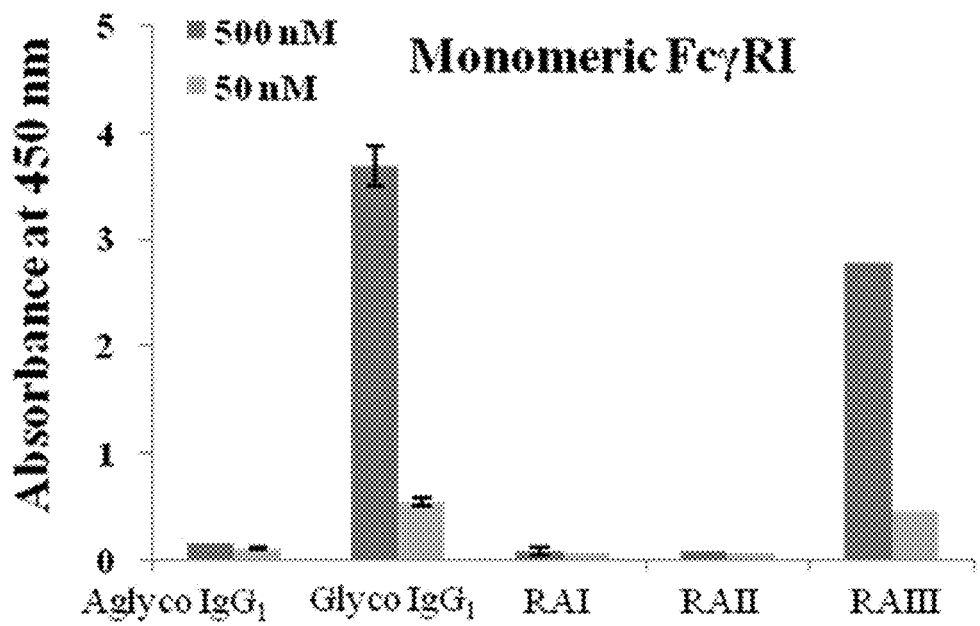
FIGS. 8A-F. ELISA results of aglycosylated Rituximab (Aglyco IgG1), glycosylated Rituximab (Glyco IgG1), and the selected IgG variants RAI, RAII, and RAIII to FcγRs; monomeric FcγRI (FIG. 8A), dimeric FcγRIIa$_{H131}$ (FIG. 8B), dimeric FcγRIIa$_{R131}$ (FIG. 8C), dimeric FcγRIIb (FIG. 8D), dimeric FcγRIIIa$_{V157}$ (FIG. 8E), and dimeric FcγRIIIa$_{F157}$ (FIG. 8F).
Figure 8B:
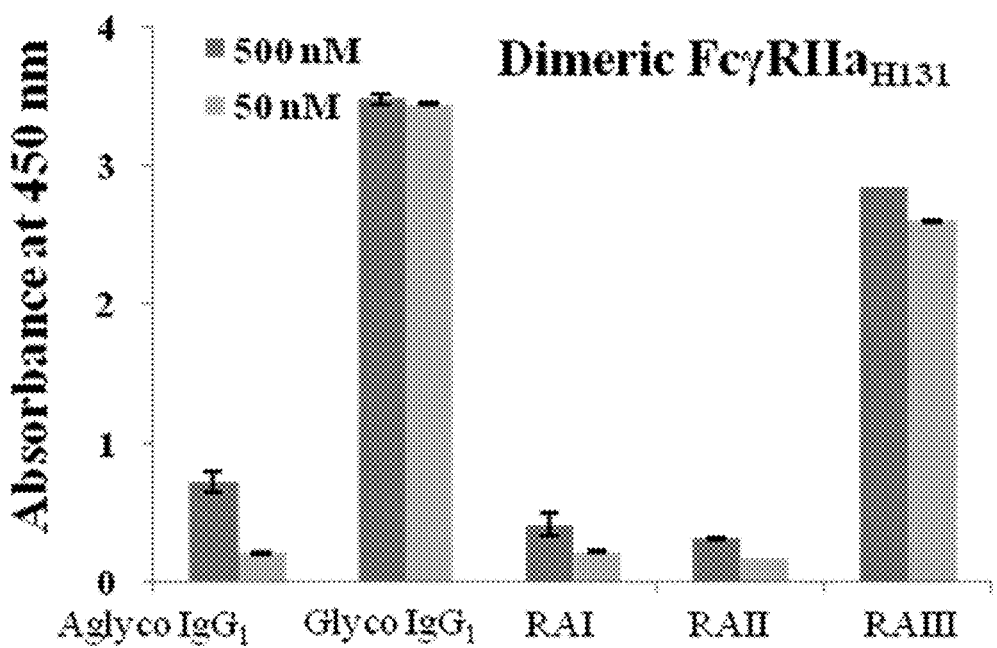
Figure 8C:
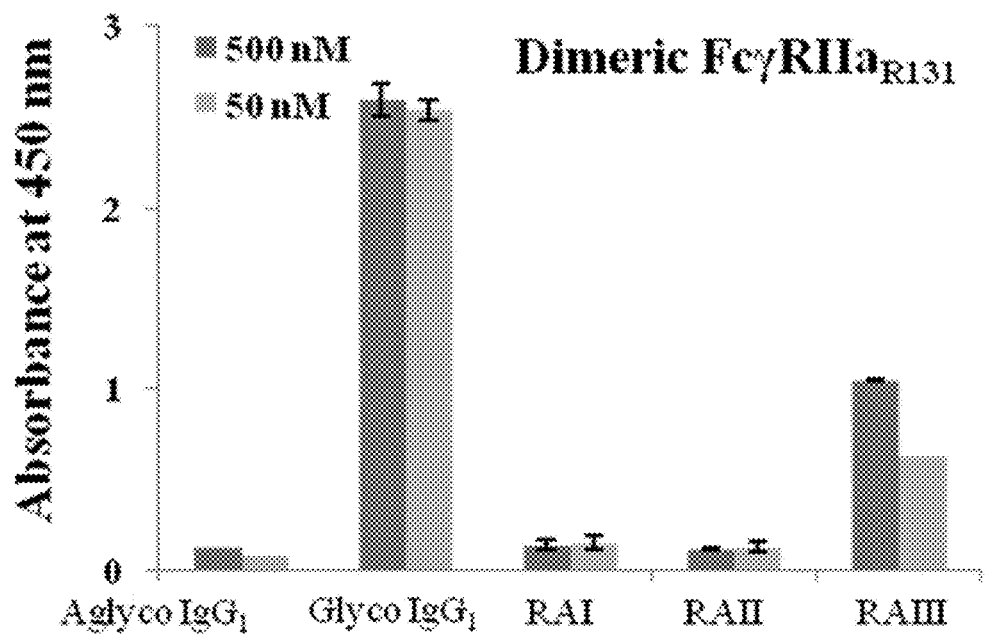
Figure 8D:
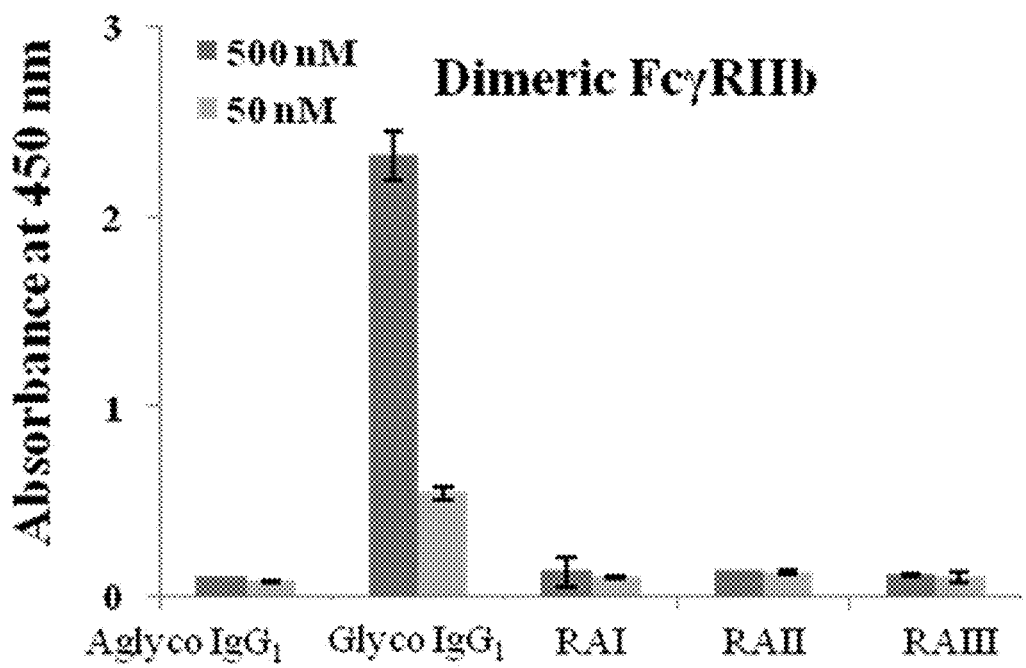
Figure 8E:
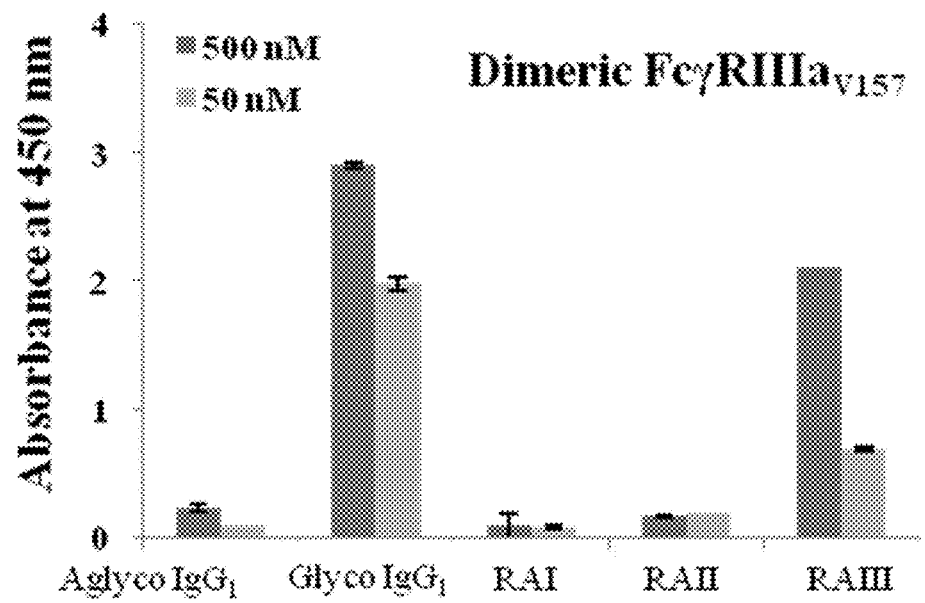
Figure 8F:
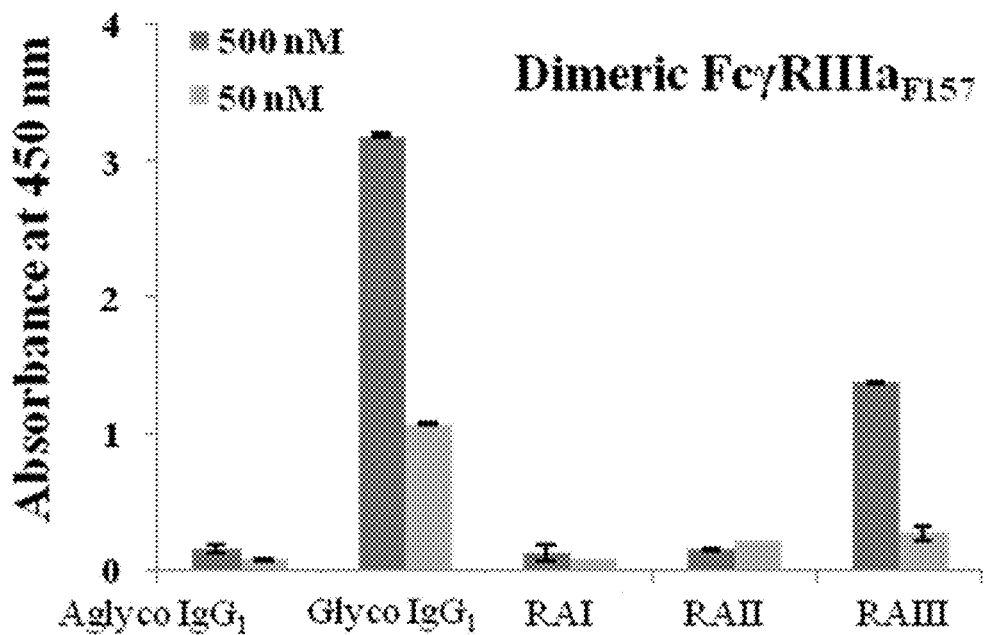

IgGs were cloned in frame into the mammalian expression vector pcDNA3.4 (Life technologies, USA) using a Gibson Assembly® cloning kit (NEB) (Jung et al., 2012). To construct Rituximab, which Fc replaced Fc801, Fc802, and Fc805, the three Fc genes were amplified from pMopac12-pelB-IgG-VH-CH1-CH2-CH3-FLAG using primers PCH001 (SEQ ID NO: 32) and TH084 (SEQ ID NO: 33). The three Fc genes were amplified for cloning into pcDNA3.4 by PCR using plasmid pcDNA3.4-Rituximab Heavy Chain as the DNA template. After treatment with Dpn1 (NEB, UK), the PCR products were transformed into E. coli JUDE-1 cells and their sequences confirmed. Newly constructed Rituximab-Fc variants received the names RGI (Fc802), RGII (Fc801), and RGIII (Fc805). These three Fc variants still have N-glycosylation sites on their CH2 domains. In order to construct their aglycosylated format, a T299L mutation, which does not affect the binding ability of the Fc domain with FcγRs or C1q, was introduced using two specific primers (WK68 (SEQ ID NO: 34) and WK69 (SEQ ID NO: 35)) as described previously (Jung et al., 2012). These newly constructed Rituximab-Fc variants received the new names of RAI (Fc802), RAII (Fc801), and RAIII (Fc805). The heavy chain genes of RAI, RAII, and RAIII were transiently transfected with an equal mass of light chain plasmid in HEK293F cells (Invitrogen). After incubation in a 5% CO$_2$ incubator at 37° C. for six days, the supernatants were collected by centrifugation at 4,000×g for 10 min and filtered using a 0.22 μm PES membrane filter (PALL). The filtered supernatants were passed over Protein A high capacity agarose resin (Thermo Scientific) three times. To remove LPS and non-specifically bound protein, the IgG-bound resins were washed with 50 mL PBS containing 0.1% Triton® X-114 (Sigma-Aldrich) and 50 mL PBS. All IgG variants were eluted with 100 mM glycine buffer (pH 3.0) and immediately neutralized with 1 M Tris-HCl buffer (pH 8.0). The buffers of all eluted Rituximab-Fc variants were exchanged to PBS by Amicon® Ultra-4 (Millipore). The purity of reduced or non-reduced proteins of RAI, RAII, and RAIII and Rituximab were assessed by 4%-20% gradient SDS-PAGE gel (NuSep) under reducing (FIG. 6A) and non-reducing (FIG. 6B) conditions. Like Rituximab, RAI, RAII, and RAIII were properly assembled with over 95% purity. In order to determine whether RAI, RAII, and RAIII exist as monomers or multimers in solution, RAI, RAII, RAIII, and Rituximab were analyzed by size exclusion chromatography (Superdex™ 200 10/300 GC, GE Healthcare). Thyroglobulin (670 kDa), bovine gamma globulin (158 kDa), and chicken ovalbumin (44 kDa) were used as protein size markers. The RAI, RAII, and RAIII elution profiles were similar with Rituximab and there was no peak of aggregates. The elution times of all IgG variants were very close to the 158 kDa protein size marker and therefore indicated the presence of monomeric IgG (FIG. 7). The results suggest that RAI, RAII, and RAIII do not make multimeric IgGs and they exist as assembled monomers in solution.

Example 7—Binding Properties of the Selected IgG Variants to C1q, FcγRs, and FcRn The affinities of RAI, RAII, and RAIII for C1q and FcγRs were evaluated using enzyme-linked immunosorbent assay (ELISA) and surface plasmon resonance (SPR).

ELISA Measurements of RAI, RAII, and RAIII with FcγRs:

The 1 μg of RAI, RAII, RAIII, aglycosylated Rituximab, and glycosylated Rituximab were coated onto a 96-well EIA/RIA plate (Qiagen) at 4° C. overnight, and the plated were washed three times with PBS containing 0.05% Tween® 20 (PBST). The plates were blocked for 1 h at room temperature with 3% skim milk in PBS and washed three times with PBST. 50 nM and 500 nM of monomeric FcγRI, dimeric FcγRIIaR131, dimeric FcγRIIaH131, dimeric FcγRIIb, dimeric FcγRIIIaV131, and dimeric FcγRIIIaF131 were then added to the plates. After 1 h of incubation at room temperature, the plates were washed with PBST and were incubated with 50 μL of PBS containing 1:5000 goat anti-His or anti-GST HRP (GE Healthcare) for 1 h. After three times of washing with PBST, 50 μL TMB substrate was added per well (Thermo Scientific), 50 μL of 1 M H$_2$SO$_4$ was added to neutralize, and the absorbance at 450 nm was recorded. The RAI and RAII did not show binding signals with any FcγRs, but RAIII showed similar or slightly reduced binding intensities with all FcγRs except FcγRIIb (FIGS. 8A-F).

Figure 9A:
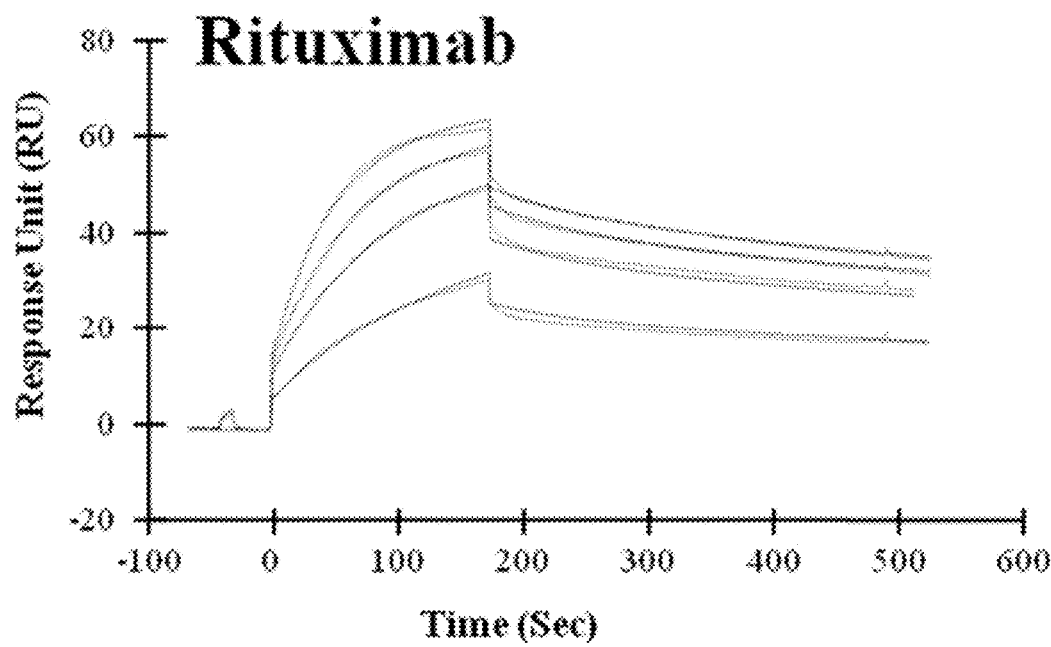
FIGS. 9A-D. The kinetic properties and surface plasmon resonance (SPR) sensorgrams of Rituximab, RAI, RAII, RGI, and RGII with C1q.
Figure 9B:
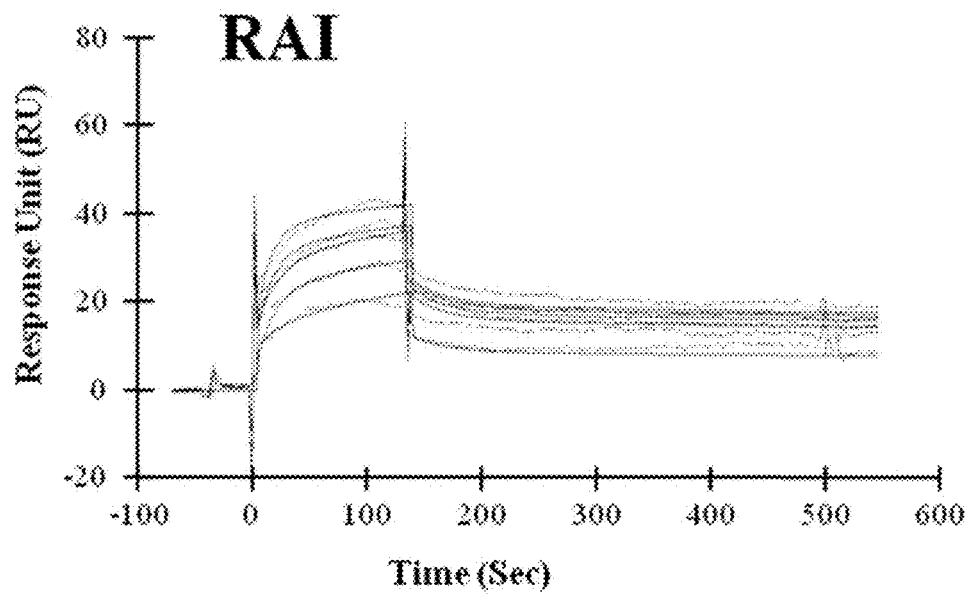
Figure 9C:
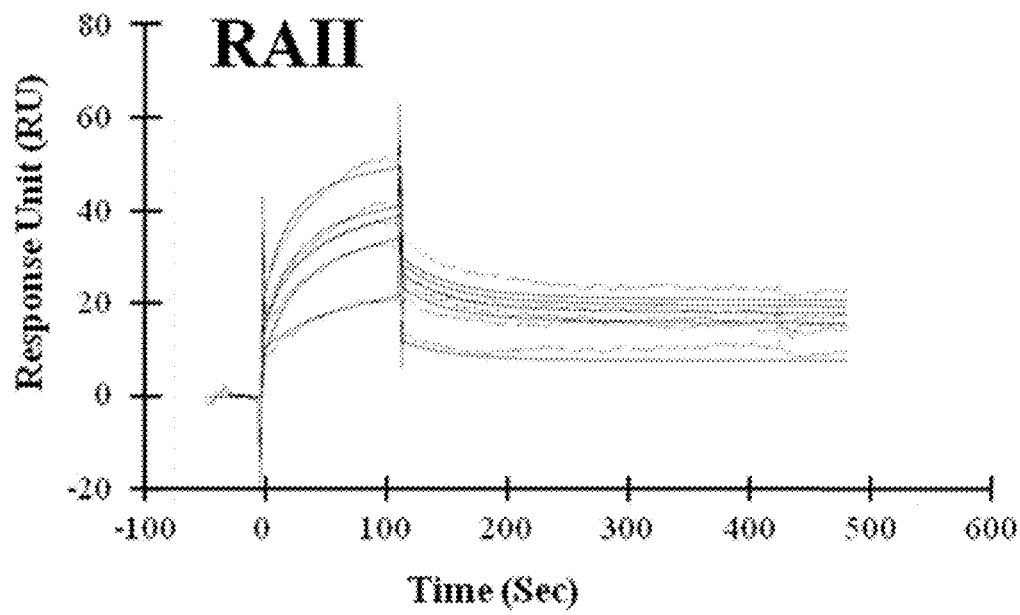
Figure 9D:
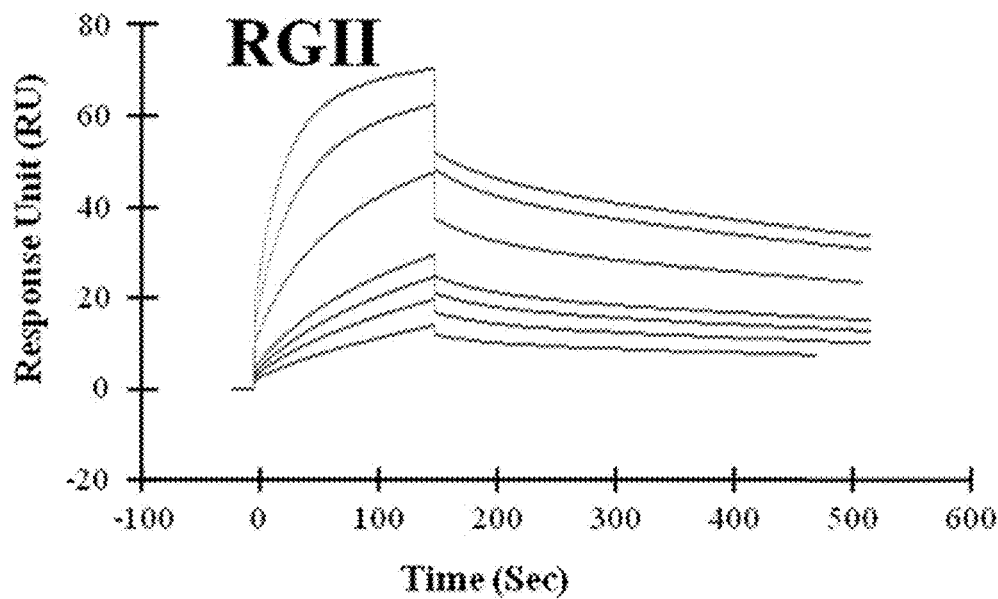
Figure 10:
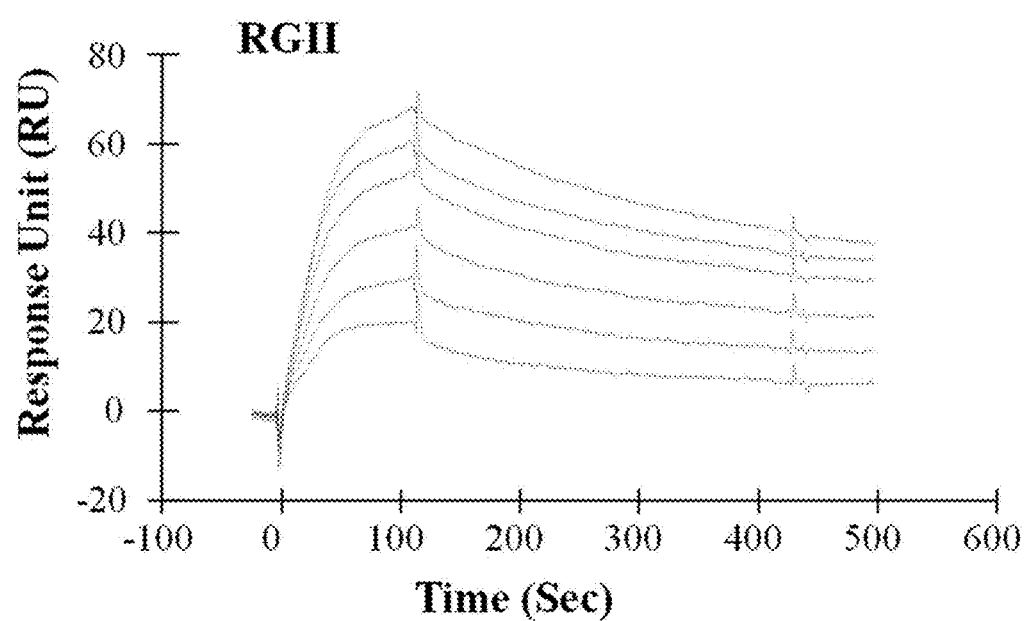
FIG. 10. The binding kinetic properties and surface plasmon resonance (SPR) sensorgrams of RGII with FcγRI. The kinetic values of RGII for monomeric FcγRI are summarized in Table 6.
Figure 11A:
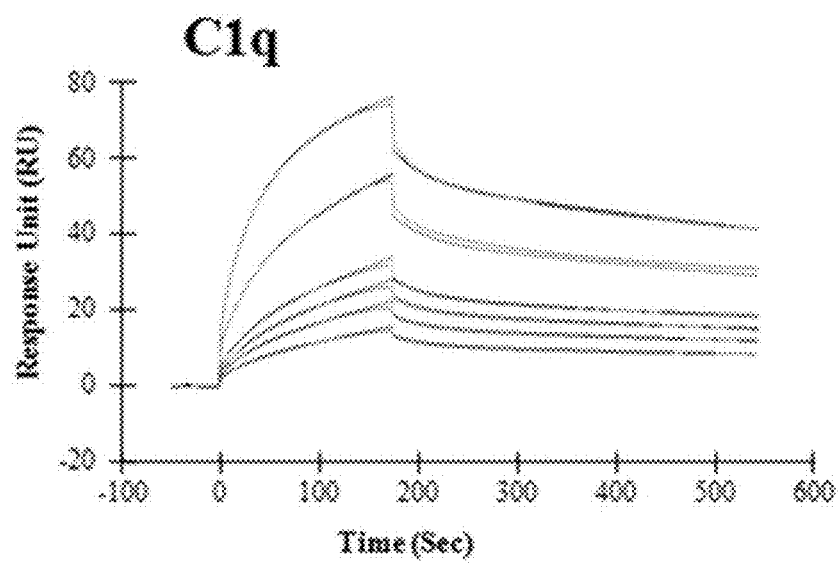
FIGS. 11A-F. SPR results of RAIII to C1q and FcγRs.
Figure 11B:
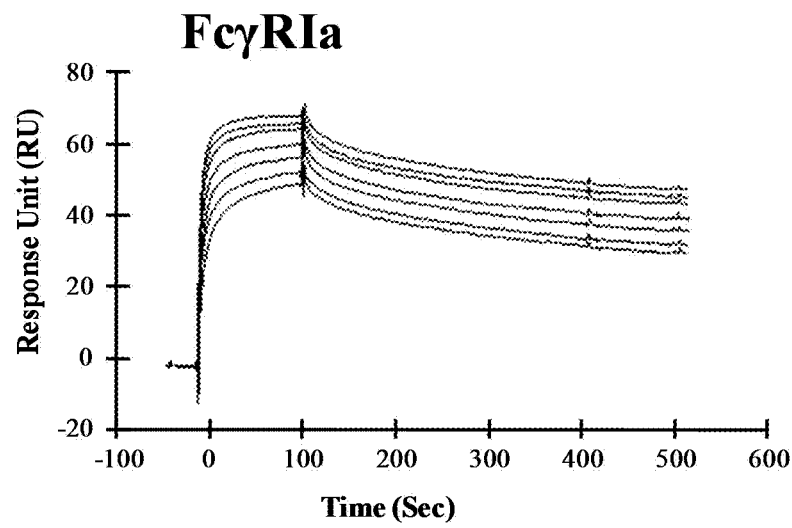
Figure 11C:
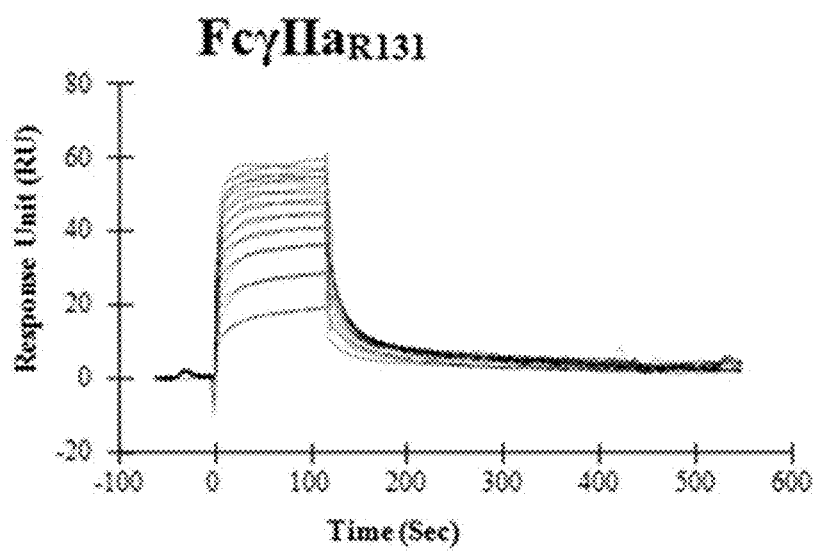
Figure 11D:
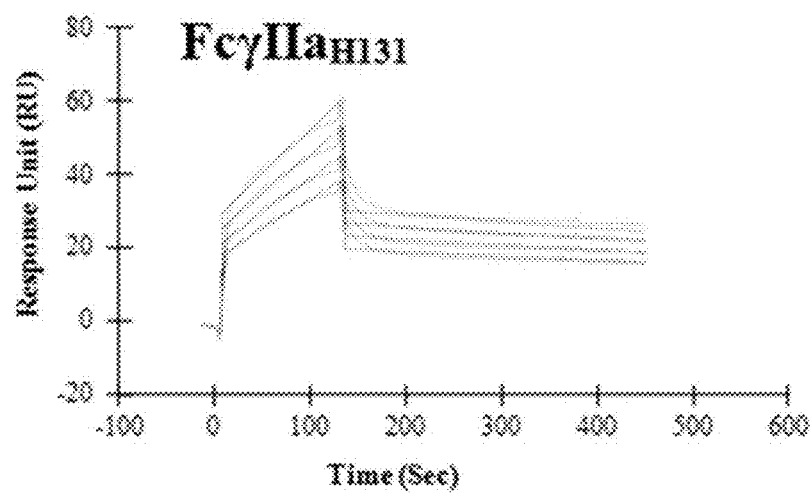
Figure 11E:
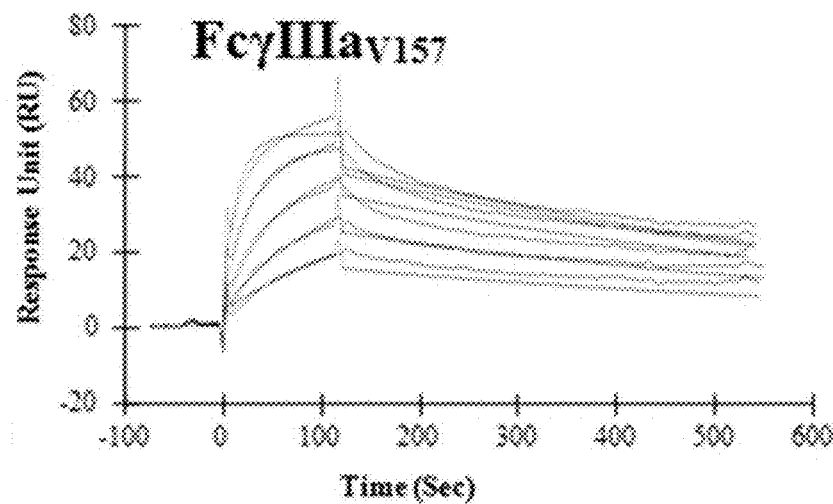
Figure 11F:
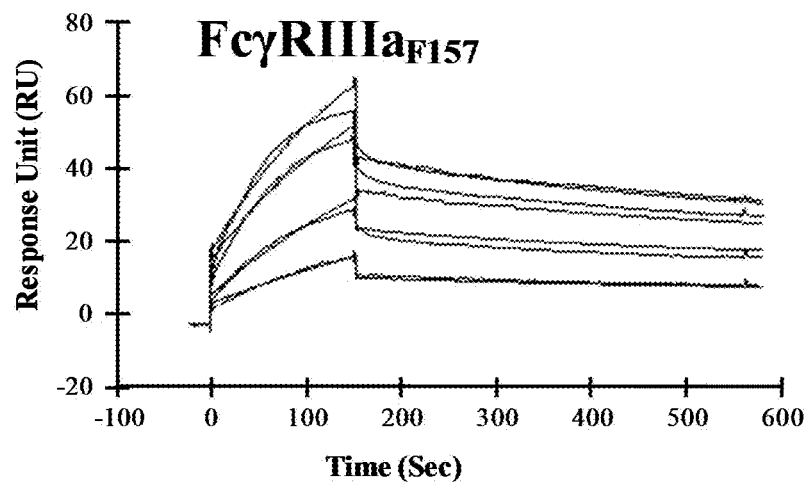

SPR Measurements:

SPR measurements were performed on a Biacore® 3000 (GE Healthcare) instrument. Bovine serum albumin (BSA) was immobilized in reference channels of the CM5 sensor chip to subtract buffer effect and non-specific binding signal. Rituximab, RAI, RAII, RGI, and RGII were immobilized on the CM5 sensor chips by amine coupling at pH 5.0. The serial diluted C1q (1 nM-40 nM), monomeric FcγRI (1 nM-40 nM), dimeric FcγRIIa$_{R131}$ (50 nM-400 nM), dimeric FcγRIIa$_{H131}$ (50 nM-400 nM), dimeric FcγRIIb (100 nM-1000 nM), dimeric FcγRIIIa$_{V131}$(50 nM-400 nM), and dimeric FcγRIIIa$_{F131}$(50 nM-400 nM) were injected in the CM5 chip at 30 μL/min for 2 min. The chip was regenerated after each binding event with 10 mM glycine (pH 3.0) with a contact time of 1 min. The resulting sensorgrams were fit with a global two-state binding model for C1q, 1:1 Langmuir isotherm model for monomeric FcγRI, and bivalent model for dimeric FcγRs using Biaevaluation 3.0 software (FIGS. 9A-D and 10; Tables 5-6). Interestingly, RAI showed C1q specific binding profiles from SPR analysis but RGI, which is the glycosylated version of RAI, lost C1q binding ability. The overall K$_D$ of RAI is 145±1 pM, an increase of 159-fold over wild-type Rituximab (FIGS. 9A-B; Table 5). RAII also showed C1q specific binding profiles from SPR analysis but unlike RAII, RGII, which is the glycosylated version of RAIL maintains C1q binding ability and had affinity for Fc$\gamma$RI. The overall $K_D$ of RAII is 108±1 pM, an increase of 213-fold over wild-type Rituximab (FIGS. 9A and C; Table 5). The $K_D$ of RGII is 385±4 pM with C1q, an increase of 60-fold over wild-type Rituximab (FIGS. 9A and D; Table 5). RGII also had a 648±16 nM $K_D$ with Fc$\gamma$RI (FIG. 10; Table 6). For other Fc$\gamma$Rs, there was no response (Table 6).

TABLE 5

Kinetic properties and surface plasmon resonance (SPR) sensorgrams of Rituximab, RAI, RAII, RGI, and RGII with C1q (data correspond to FIGS. 9A-D)

| | $k_{on}1$ (1/Ms) | $k_{off}1$ (1/s) | $k_{on}2$ (1/RU) | $k_{off}2$ (1/s) | $K_{D1}$ | $K_{D2}$ | $K_D{}^a$ (nM) | Fold[b] | chi$^2$ |
|---|---|---|---|---|---|---|---|---|---|
| Rituximab | $1.80 \times 10^5$ | $4.75 \times 10^{-2}$ | $1.03 \times 10^{-2}$ | $9.84 \times 10^{-4}$ | $2.64 \times 10^{-7}$ | $9.55 \times 10^{-2}$ | 23.0 ± 0.8 | 1 | 3.44 |
| RAI | $5.36 \times 10^6$ | $2.33 \times 10^{-2}$ | $1.15 \times 10^{-3}$ | $3.96 \times 10^{-4}$ | $4.35 \times 10^{-9}$ | $3.44 \times 10^{-2}$ | 0.145 ± 0.001 | 159 | 0.925 |
| RGI | No detectable response | | | | | | | | |
| RAII | $2.98 \times 10^6$ | $1.49 \times 10^{-2}$ | $9.11 \times 10^{-3}$ | $2.01 \times 10^{-4}$ | $5.00 \times 10^{-9}$ | $2.21 \times 10^{-2}$ | 0.108 ± 0.001 | 213 | 1.05 |
| RGII | $7.54 \times 10^5$ | $2.34 \times 10^{-3}$ | $1.62 \times 10^{-3}$ | $2.29 \times 10^{-4}$ | $3.10 \times 10^{-9}$ | $1.41 \times 10^{-1}$ | 0.385 ± 0.004 | 60 | 1.21 |

$K_D{}^a = K_{D1}/(1 + 1/K_{D2})$ from a global two-state binding fit of SPR data
Fold[b] = $K_D$ (Native IgG1)/$K_D$(IgG variant)

TABLE 6

Kinetic values of RGII for monomeric Fc$\gamma$RI (data correspond to FIG. 10)

| | Monomeric Fc$\gamma$RI | | | | Dimeric Fc$\gamma$RIIa, Fc$\gamma$RIIb, and |
|---|---|---|---|---|---|
| | $k_{on}$ (1/Ms) | $k_{off}$ (1/s) | $K_D$ (nM) | chi$^2$ | Fc$\gamma$RIIIa |
| RAI | No detectable response | | | | |
| RGI | No detectable response | | | | |
| RAII | No detectable response | | | | |
| RGII | $2.27 \times 10^3$ | $1.47 \times 10^{-3}$ | 648 ± 16 | 2.45 | No detectable response |

In order to analyze the pH-dependent-binding of RA801 and RA802 to the FcRn-GST fusion proteins (730 nM) was injected in the CM5 chip at 30 μl/min of pH 7.4 HBS-EP (GE-Healthcare) for 90 seconds. The chip was regenerated after each binding event with 10 mM Glycine pH 3.0 with a contact time of 1 minute. SPR measurements with monomeric FcRn (50-400 nM) was injected in the CM5 chip at 30 μl/min of pH 6.0 PBS for 90 seconds and the chip was regenerated after each binding event with 10 mM Glycine pH 3.0 for 1 minute. RAI and RAII showed pH-dependent binding properties. The $K_D$ of RAI is 110±8 nM with FcRn, an increase of 5.66-fold over wild-type Rituximab at pH 6.0 (FIG. 18B; Table 7). The $K_D$ of RAII is 959±69 nM with FcRn, or 0.65-fold over wild-type Rituximab at pH 6.0 (FIG. 18C; Table 7). No binding was observed at pH 7.4 (FIG. 18D; Table 7).

TABLE 7

Kinetic values of RAI and RAII for FcRn (data correspond to FIG. 18)

| | Monomeric FcRn at pH 6.0 | | | | Dimeric FcRn at pH 7.4 | | | |
|---|---|---|---|---|---|---|---|---|
| | $k_{on}$ (1/Ms) | $k_{off}$ (1/s) | $K_D$ (nM) | chi$^2$ | $k_{on}$ (1/Ms) | $k_{off}$ (1/s) | $K_D$ (nM) | chi$^2$ |
| Rituximab | $8.32 \times 10^5$ | $4.91 \times 10^{-1}$ | 623 ± 35 | 1.59 | No detectable response | | | |
| RAI | $3.92 \times 10^5$ | $4.23 \times 10^{-2}$ | 110 ± 8 | 1.77 | No detectable response | | | |
| RAII | $5.81 \times 10^5$ | $5.39 \times 10^{-1}$ | 959 ± 69 | 2.49 | No detectable response | | | |

SPR Measurements of RAIII:

Using the same method, the serial diluted C1q and FcγRs were injected in the CM5 sensor chip after immobilization of RAIII The SPR sensorgrams were fitted using the same methods as described above. RAIII had affinities for C1q and FcγRs, except FcγRIIb, as follows: 1.60±0.03 nM for C1q (FIG. 11A; Table 8), 13.4±0.4 nM for monomeric FcγRI (FIG. 11B; Table 8), 127±1 nM for dimeric FcγRIIa$_{R131}$ (FIG. 11C; Table 8), 102±2 nM for dimeric FcγRIIa$_{H131}$ (FIG. 11D; Table 8), 79.8±0.9 nM for dimeric FcγRIIIa$_{V131}$ (FIG. 11E; Table 8), and 390±8 nM for dimeric FcγRIIIa$_{F131}$ (FIG. 11F; Table 8). Table 9 shows the summarized binding profiles of IgG variants comparing with native IgG1.

TABLE 8

SPR results of RAIII to C1q and FcγRs (data correspond to FIGS. 11A-F)

| | k$_{on}$1 (1/Ms) | k$_{off}$1 (1/s) | k$_{on}$2 (1/RU) | k$_{off}$2 (1/s) | K$_{D1}$ | K$_{D2}$ | K$_D^a$ (nM) | chi$^2$ |
|---|---|---|---|---|---|---|---|---|
| C1q | 3.83 × 10$^5$ | 4.33 × 10$^{-3}$ | 1.35 × 10$^{-2}$ | 2.22 × 10$^{-3}$ | 1.13 × 10$^{-8}$ | 1.64 × 10$^{-1}$ | 1.60 ± 0.03 | 1.78 |
| Monomeric FcγIa | 6.85 × 10$^4$ | 9.15 × 10$^{-4}$ | | | | | 13.4 ± 0.35 | 2.62 |
| Dimeric FcγIIa$_{R131}$ | 4.05 × 10$^4$ | 5.73 × 10$^{-3}$ | 2.08 × 10$^{-5}$ | 1.89 × 10$^{-4}$ | 1.41 × 10$^{-7}$ | 9.09 | 127 ± 1 | 0.685 |
| Dimeric FcγIIa$_{H131}$ | 7.40 × 10$^3$ | 1.72 × 10$^{-3}$ | 1.55 × 10$^{-5}$ | 1.22 × 10$^{-5}$ | 2.32 × 10$^{-7}$ | 7.87 × 10$^{-1}$ | 102 ± 2 | 1.62 |
| Dimeric FcγIIb | | | | No detectable response | | | | |
| Dimeric FcγIIIa$_{V157}$ | 2.85 × 10$^4$ | 2.52 × 10$^{-3}$ | 0.047 | 0.436 | 8.84 × 10$^{-8}$ | 9.28 | 79.8 ± 0.9 | 1.09 |
| Dimeric FcγIIIa$_{F157}$ | 1.37 × 10$^3$ | 1.34 × 10$^{-2}$ | 6.96 × 10$^{-3}$ | 2.89 × 10$^{-4}$ | 9.78 × 10$^{-6}$ | 4.15 × 10$^{-2}$ | 390 ± 8 | 2.10 |

K$_D^a$ = K$_{D1}$/(1 + 1/K$_{D2}$) from a global two-state binding fit or a bivalent model fit of SPR data

TABLE 9

Summary binding profiles of IgG variants with C1q and FcγRs (KD (nM)/fold affinity differences (comparing with Rituximab)

| | N-Glycosylation | C1q | Monomeric FcγRIa | Dimeric FcγRIIa$_{H131}$ | Dimeric FcγRIIa$_{R131}$ | Dimeric FcγRIIb | Dimeric FcγRIIIa$_{V158}$ | Dimeric FcγRIIIa$_{F158}$ |
|---|---|---|---|---|---|---|---|---|
| Native IgG1 | Yes | 23.0 | 1.5 | 120 | 310 | 1300 | 195 | 390 |
| RAI | No | 0.145 (158 fold) | n.b. | n.b. | n.b. | n.b. | n.b. | n.b. |
| RGI | Yes | n.b. | n.b. | n.b. | n.b. | n.b. | n.b. | n.b. |
| RAII | No | 0.108 (213 fold) | n.b. | n.b. | n.b. | n.b. | n.b. | n.b. |
| RGII | Yes | 0.385 (60 fold) | 648 (0.002 fold) | n.b. | n.b. | n.b. | n.b. | n.b. |
| RAIII | No | 1.60 (14.3 fold) | 13.4 (0.11 fold) | 102 (0.81 fold) | 127 (2.4 fold) | n.b. | 79.8 (3.25 fold) | 390 (1 fold) | n.b.: Did not bind
K$_D$ values for C1q are relative affinities for C1q.
IgG data from Jung et al. (2013).

Example 8—Further Engineering of RAIII

Figure 19:
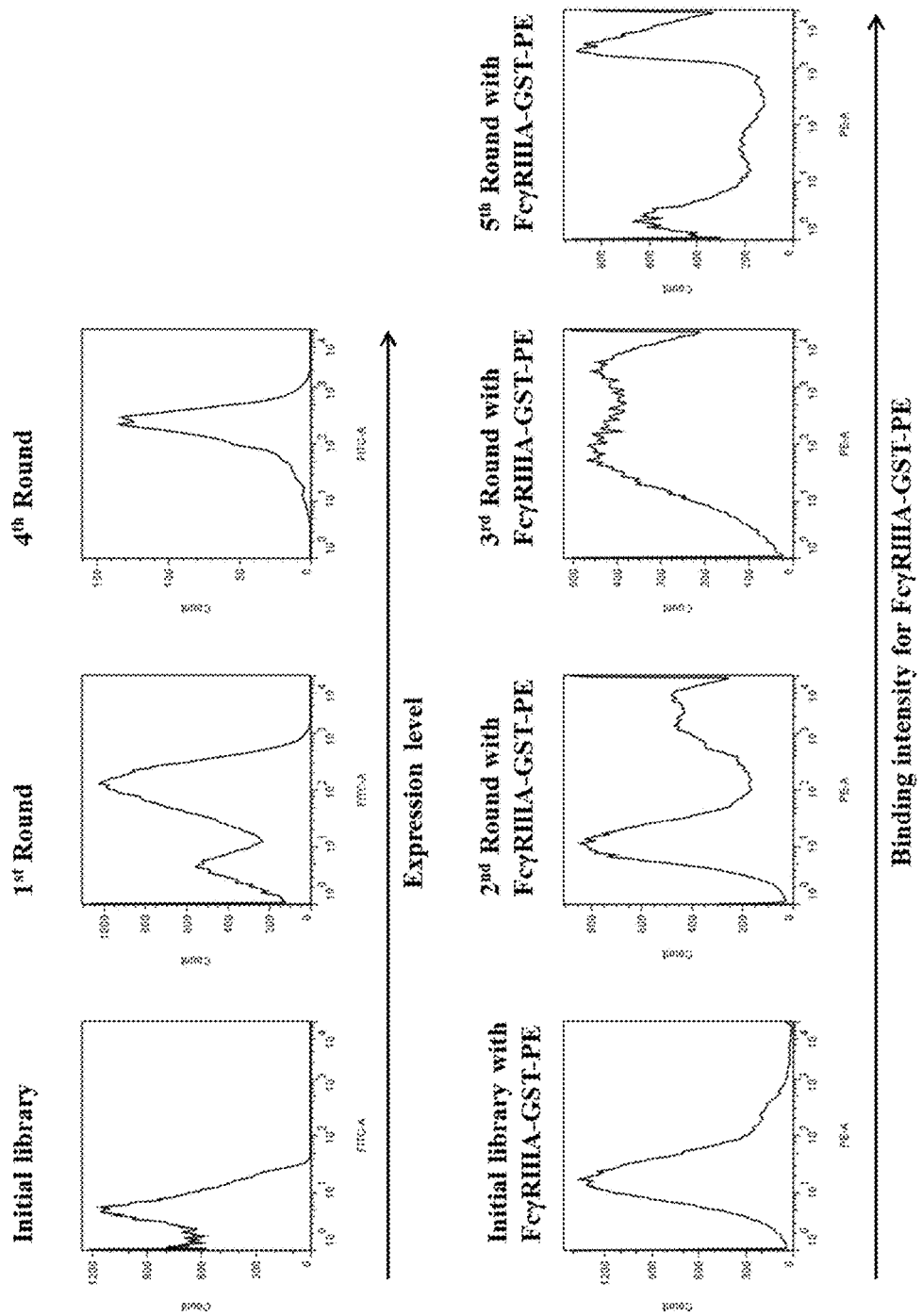
FIG. 19. FACS analysis histograms showing enrichment of the RAIII library. At 1$^{st}$ and 4$^{th}$ rounds, the library was screened by expression level. At 2$^{nd}$, 3$^{rd}$, and 5$^{th}$ rounds, the library was screened by FcγRIIIa.

In order to enhance the yield and stability of RAIII, a library of random mutations of RAIII was constructed by error prone PCR under conditions where the mutation rate was 1%, using the same methods as in Example 2. The library was screened in two different ways. First, the library was labeled and screened with anti-myc Ab-FITC, which can detect the expression level of antibodies, at 1$^{st}$ and 4$^{th}$ rounds by FACSAria™ (BD Biosciences) to select for enhanced expression level. Second, the library was labeled and screened with 100 nM FcγRIIIa-GST-PE in the presence of 1 μM FcγRIIb as a competitor after the 2$^{nd}$, 3$^{rd}$ and 5$^{th}$ rounds by FACSAria™ (BD Biosciences) in order to isolate RAIII variants that maintain the same binding characteristics as RAIII but can be expressed at a higher level than RAIII Fluorescence profiles during screening are shown in FIG. 19.

Example 9—FACS Analysis of the IgG Variants

Figure 20:
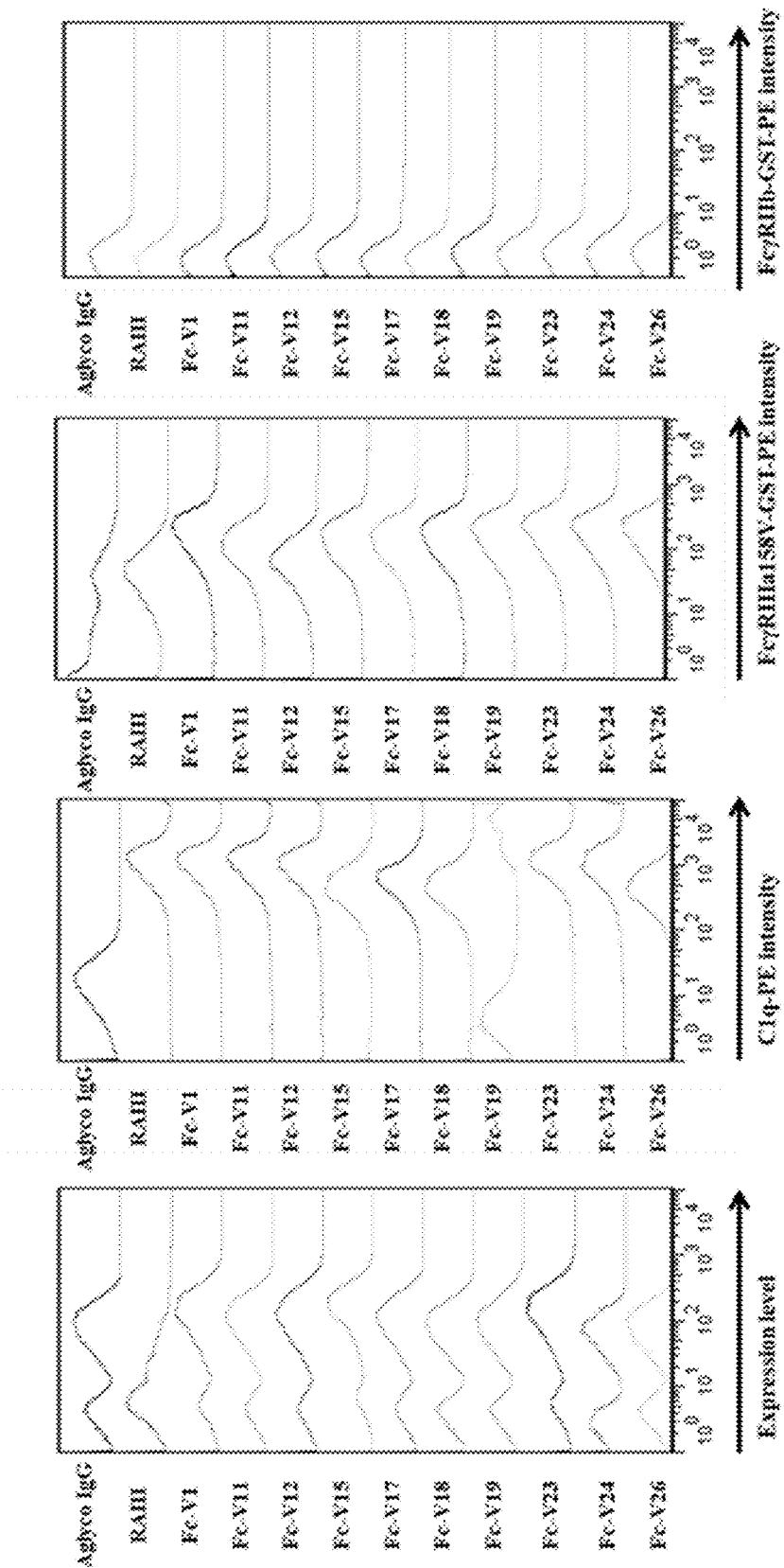
FIG. 20. Binding analysis of the ten isolated IgG variants from RAIII-Fc library using FACS. Left histogram shows expression level by anti-c-myc IgG with FITC. Second histogram shows C1q binding intensities. Third histogram shows FcγRIIIa-GST-PE binding intensities. Fourth histogram shows FcγRIIb-GST-PE binding intensities. Mean fluorescence intensities are listed in Table 10.

Fifty randomly selected IgG variants from the last (5$^{th}$) round of library sorting were sequenced (SEQ ID NOs: 36-45) and found to encode only 10 different Fc variants (represented at multiple copies in the pool of 50 selected clones). Fc-V1 has a single mutation, M252V (SEQ ID NO: 36). Fc-V11 has three mutations, K246N, K322E, and G402D (SEQ ID NO: 37). Fc-V12 has 7 mutations, F242L, N315S, I336M, K340R, Q342D, A378T, and Q386R (SEQ ID NO: 38). Fc-V15 has three mutations, K334E, L351Q, and N421D (SEQ ID NO: 39). Fc-V17 has two mutations, G341A and L351Q (SEQ ID NO: 40). Fc-V18 has three mutations, M252V, G341A, and L351Q (SEQ ID NO: 41). Fc-V19 has four mutations, K246Q, T260A, N315S, and Q386R (SEQ ID NO: 42). Fc-V23 has 6 mutations, K246N, M252V, K322E, R344G, E345Y, and F372L (SEQ ID NO: 43). Fc-V24 has five mutations, F242L, M252V, K338Q, G341A, and E345Y (SEQ ID NO: 44). Fc-V26 has 7 mutations, K334E, G402D, K338Q, Q342P, R344G, E345Y, and F372L (SEQ ID NO: 45). Fc variant-expressing cells were labeled and analyzed with 10 nM of C1q, 100 nM FcγRIIIa$_{V158}$-GST-PE or FcγRIIb-GST-PE (FIG. 20 and Table 10). The isolated ten IgG variants showed 1.5-3.9 fold enhanced expression levels, similar C1q-binding activities (1.3-1.6 fold), and 3.5-5.1 fold enhanced FcγRIIIa$_{V158}$-GST binding activities than RAIII All ten IgG variants showed no detectable binding activity for dimeric FcγRIIb-GST fusion.

TABLE 10

Binding analysis of the isolated ten IgG variants with anti-myc Ab-FITC, C1q-PE, FcγRIIIa-GST-PE, or FcγRIIb-GST-PE using FACS (data correspond to FIG. 20)

| | Expression | | C1q-PE | | FcγRIIIa$_{158V}$-GST-PE | | FcγRIIb-GST-PE | |
|---|---|---|---|---|---|---|---|---|
| | MFI | Increasing Fold | MFI | Increasing Fold | MFI | Increasing Fold | MFI | Increasing Fold |
| Aglyco IgG | 60.5 | 1 | 23.5 | 1 | 3.8 | 1 | 4.5 | 1 |
| RAIII | 39.05 | 0.65 | 806.8 | 34.33 | 34.8 | 9.16 | 7.5 | 1.67 |
| Fc-V1 | 98.2 | 1.62 | 1053.5 | 44.82 | 122.6 | 32.26 | 6.8 | 1.51 |
| Fc-V11 | 118 | 1.95 | 1122.5 | 47.76 | 158.6 | 41.74 | 8.1 | 1.80 |
| Fc-V12 | 86.5 | 1.43 | 1035.5 | 44.06 | 176.5 | 46.45 | 7.9 | 1.76 |
| Fc-V15 | 95.1 | 1.57 | 1305.5 | 55.55 | 129.3 | 34.03 | 11.8 | 2.62 |
| Fc-V17 | 69.7 | 1.15 | 1125.8 | 47.90 | 184.5 | 48.55 | 6.8 | 1.51 |
| Fc-V18 | 88.5 | 1.46 | 1046.5 | 44.53 | 176.5 | 46.45 | 9.8 | 2.18 |
| Fc-V19 | 153.5 | 2.54 | 1333.8 | 56.75 | 166.7 | 43.87 | 6.9 | 1.53 |
| Fc-V23 | 62.7 | 1.04 | 1209.1 | 51.45 | 136.5 | 35.92 | 10.5 | 2.33 |
| Fc-V24 | 79.8 | 1.32 | 1143.7 | 48.66 | 129.8 | 34.16 | 9.4 | 2.09 |
| Fc-V26 | 58.5 | 0.97 | 1210.9 | 51.52 | 135.9 | 35.76 | 7.5 | 1.67 |

Figure 21:
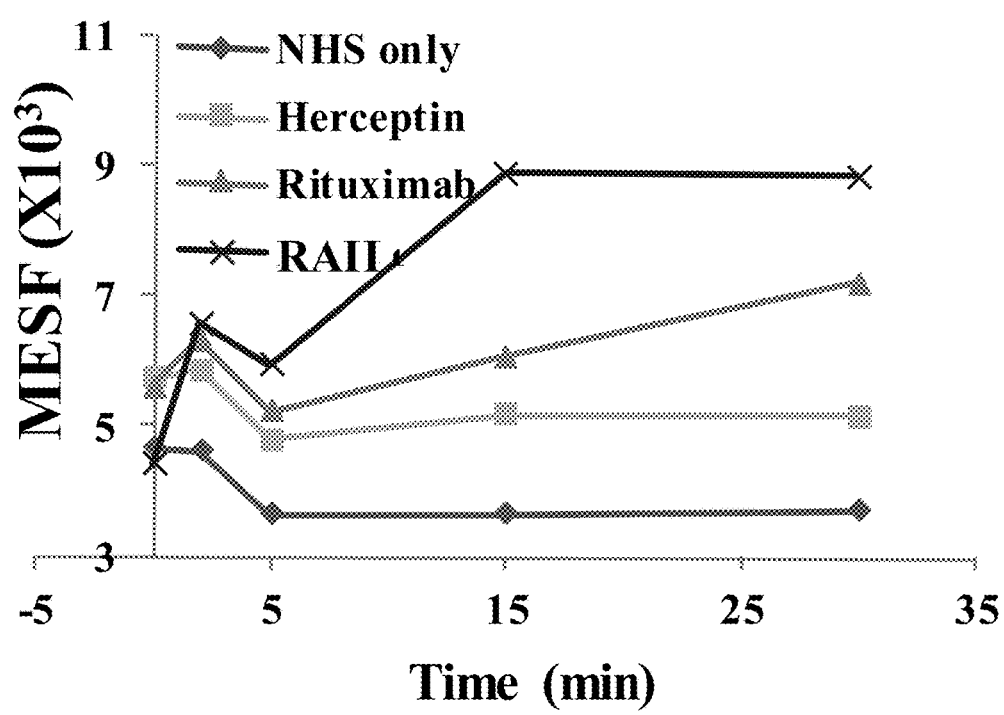
FIG. 21. C1q binding analysis on each antibody opsonized CD20-positive Raji cells. After incubation of C1q with each antibody opsonized CD20-positive Raji cells, C1q-binding intensity was detected by anti-C1q-FITC antibody.

Example 10—C1q-Binding and C3b-Deposition Activities on Raji Cells Opsonized with the Selected IgG Variants C1q binding assays were conducted in complete RPMI 1640 medium (10% FBS). CD20 positive Raji cells (human Burkitt's lymphoma, ATCC CCL-86; Golay, 2000) were suspended on ice at $1 \times 10^7$ cells/ml. C1q was added to give a final concentration of 10 µg/ml, and Herceptin, Rituximab, or RAII were then added and the reaction mixtures immediately transferred to a 37° C. water bath. Aliquots were removed at various times (0-60 min) and quenched with 20 volumes of ice-cold BSA-PBS. Cells were then washed three times with 1% BSA in PBS, probed with FITC anti-C1q for 30 min at room temperature and then washed with 1% BSA in PBS and fixed in PBS containing 2% paraformaldehyde. Flow cytometry was performed on a FACSCalibur flow cytometer (BD Biosciences) and mean fluorescence intensities were converted to molecules of equivalent soluble fluorochrome (MESF) using calibrated beads (Spherotech). RAII showed stronger binding activity to C1q than Rituximab on RAII-opsonized Raji-cell surfaces (FIG. 21).

Figure 22:
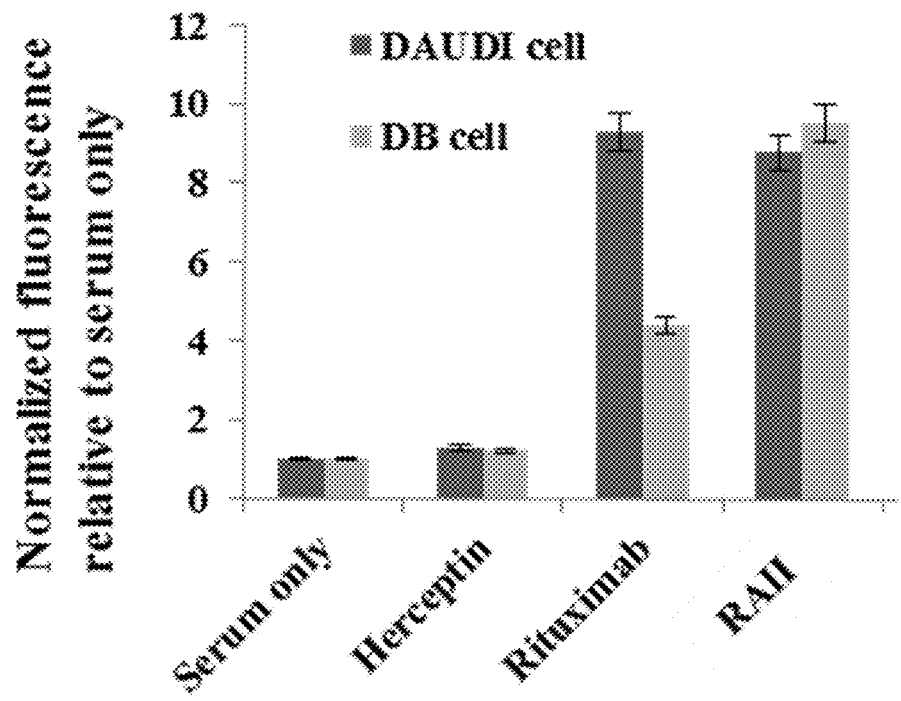
FIG. 22. C3b deposition assay on CD20-positive DAUDI and DB cells by RAII. The deposited C3b was detected by FITC mAb 7C12 (anti-C3b mouse IgG).

The level of C3b-deposition by Rituximab and RAII on CD20-positive DAUDI (human Burkitt's lymphoma, ATCC CCL-213) and on DB cancer cells (human large cell lymphoma, ATCC CRL2289) was determined. Cells in complete RPMI 1640 medium were mixed with an equal volume of NHS (normal human serum), and then mAbs were added to a final concentration of 10 µg/ml. After incubation for 30 minutes at 37° C., cells were washed twice with 1% (BSA-PBS) and developed with FITC mAb 7C12 (anti-C3b mouse IgG). Flow cytometry was performed on a FACSCalibur flow cytometer (BD Biosciences) and the results are shown in FIG. 22. The level of C3b-deposition is represented as the fold-difference compared to a serum-only control. RAII showed a similar level of C3b-deposition in DAUDI cancer cells and a higher level of C3b-deposition in DB cells relative to Rituximab.

Example 11—Solution Phase Complement Activation

Figure 23:
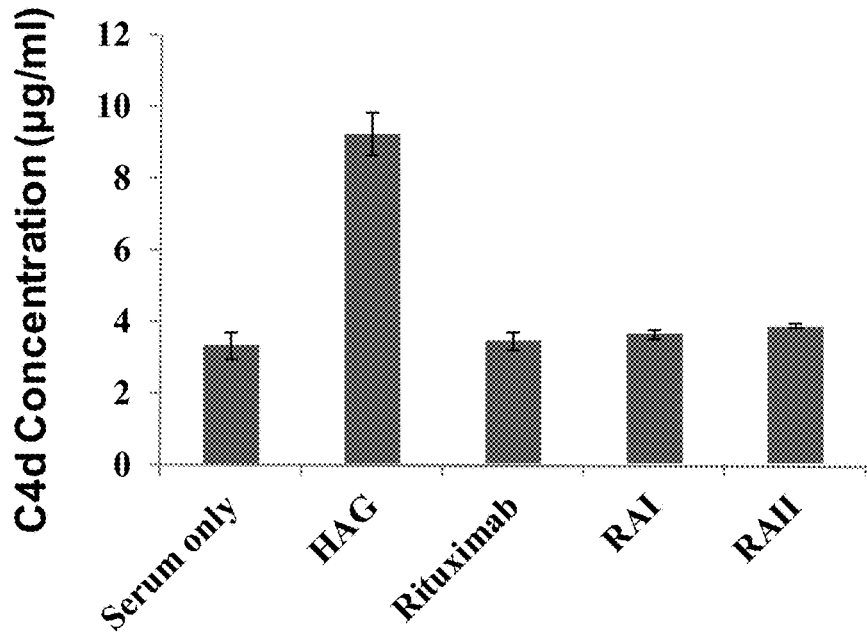
FIG. 23. Solution phase complement activation assay. Complement activation in the absence of tumor cells was determined by measuring C4d concentrations. C4d concentrations were measured in an ELISA (MicroVue C4d EIA kit, Quidel Corporation, San Diego, US) according to the manufacturer's instructions.

Complement activation in the absence of cancer cells was determined by measuring C4d concentrations, a marker for classical pathway complement activation, after incubating 100 µg antibody in 1 mL 90% normal human serum for 1 hour at 37° C. C4d concentrations were measured in an ELISA (MicroVue C4d EIA kit, Quidel Corporation, San Diego, US) according to the manufacturer's instructions. Heat aggregated IgG (HAG) showed the 2.8-fold increased C4d concentration compared to normal human serum control. Rituximab, RAI, and RAII showed the same C4d formation as the normal human serum control (FIG. 23). This result reveals that RAI and RAII cannot activate the classical complement activation pathway in solution in the absence of target cells (where no immune complexes are formed).

Example 12—Complement Dependent Cytotoxicity Assay for the Killing of Cancer Cells by the Selected IgG Variants CDC Assay:

In order to evaluate the efficacy of the RAI, RAII, or RAIII mediated complement dependent cytotoxicity (CDC), Raji cells and Ramos cells (human Burkitt's lymphoma, ATCC CCL-86) were used as the target cells. Raji and Ramos cells were cultured in RPMI 1640 medium (Invitrogen, USA) supplemented with 10% FBS (Invitrogen, USA) and collected by centrifugation at 300×g for 5 min. The harvested cells were washed in PBS and labeled with 4 µM Calcein AM (Life Technologies, USA) in PBS at 37° C. with 5% $CO_2$ for 30 min. The labeled Raji cells were washed in PBS twice, resuspended in RPMI 1640 medium containing 10% FBS, and seeded into a 96-well plate at 5,000 cells/well. Normal human blood from healthy donor was collected in red/grey clot activator tubes with gel, left to stand for 30 min, and centrifuged at 1500×g for 15 min. Then 25 µL of normal human serum was added to each well. The IgG variants at various concentrations were added to each well, mixed, and incubated at 37° C. with 5% $CO_2$ for 1 h. The plates were centrifuged at 2000 rpm for 10 min, and then the supernatants were collected. The released calcein AM was detected at excitation and emission wavelengths of 485 nm and 535 nm, respectively. The percent of tumor cell lysis was calculated according to the following formula: 100× (E−S)/(M−S), where E is the fluorescence of the experimental well, S is the fluorescence in the absence of antibody (tumor cells were incubated with medium and complement alone), and M is that of tumor cells with lysis buffer (Triton® X-100 at 2% v/v, SDS at 1% w/v, 100 mM NaCl, and 1 mM EDTA). The $EC_{50}$ of RAI was 9.05±0.90 nM, an increase of 3.77-fold over wild-type Rituximab in Raji cells. The $EC_{50}$ of RAII was 4.48±0.26 nM, an increase of 7.62-fold over wild-type Rituximab in Raji cells. The $EC_{50}$ of RAIII was 7.35±0.22 nM, an increase of 4.64-fold over wild-type Rituximab in Raji cells (FIG. 12; Table 11). The $EC_{50}$ of RAI was 0.46±0.02 nM, an increase of 2.0-fold over wild-type Rituximab in Ramos cells. The $EC_{50}$ of RAII was 0.16±0.01 nM, an increase of 5.7-fold over wild-type Rituximab in Ramos cells (FIG. 24; Table 11). The isotype control antibody, Herceptin, did not show any significant response in Raji and Ramos cells (FIG. 12; Table 11). The same CDC assay was also performed with human acute lymphoblastic leukemia (ALL) primary cells from an ALL patient donor (from MD Anderson). IgG variants mediated cell lysis by complement showed similar profiles with previous results of CDC assay (FIG. 13). RAI, RAII, and RAIII induced concentration-dependent CDC-mediated tumor cell lysis better than Rituximab.

TABLE 11

Figure 12:
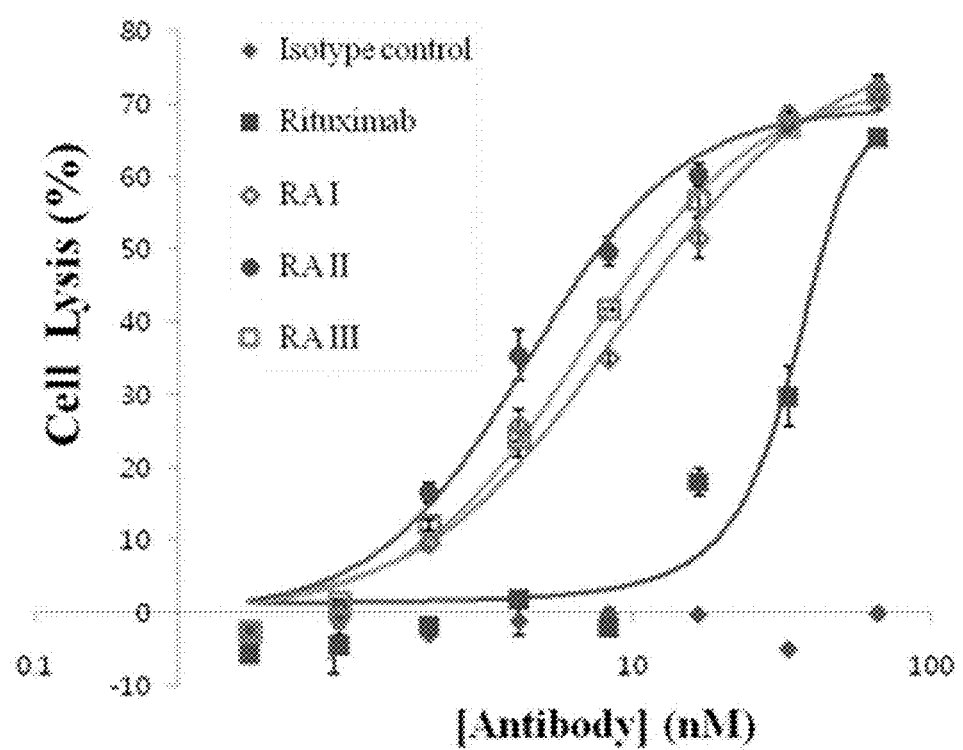
FIG. 12. Complement dependent cytotoxicity (CDC) assay of IgG variants using normal human serum and CD20 positive Raji cells as targets. The EC$_{50}$ values and fold change are presented in Table 11.
Figure 13:
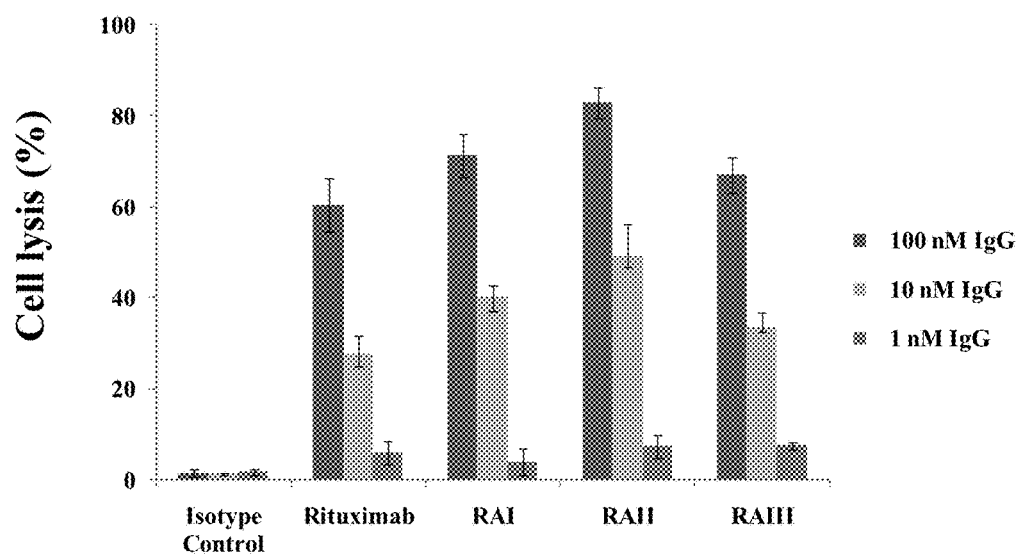
FIG. 13. CDC assay of IgG variants using normal human serum and primary cells from ALL patients. The columns for each variant represent, from left to right, 100 nM IgG; 10 nM IgG; and 1 nM IgG.
Figure 24:
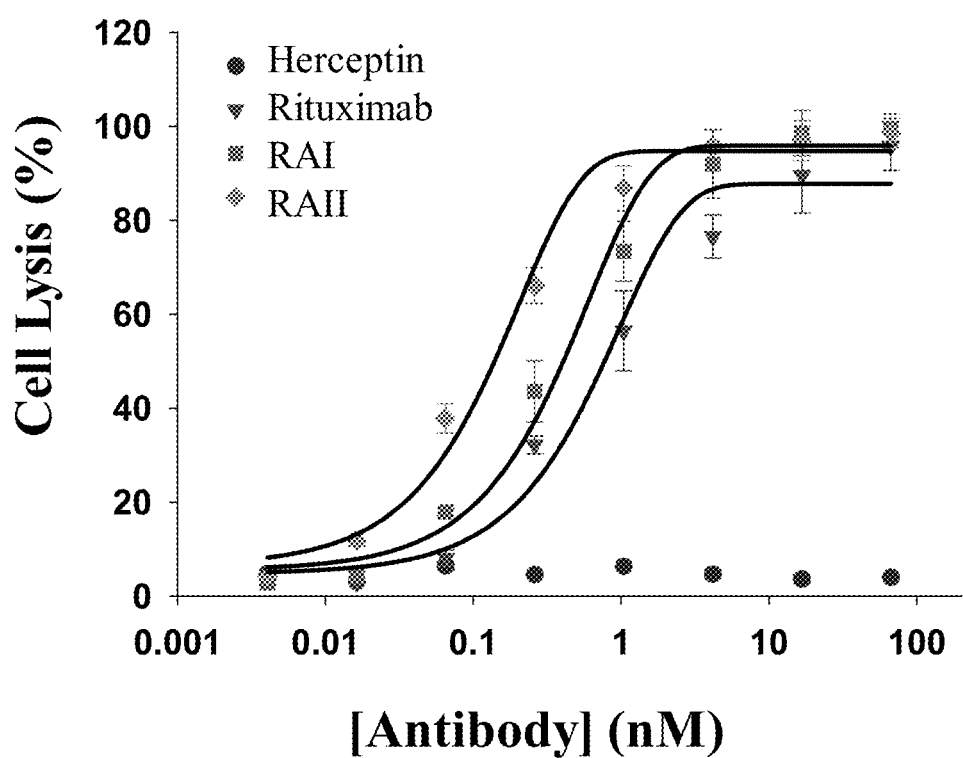
FIG. 24. Complement dependent cytotoxicity (CDC) assay of IgG variants using normal human serum and CD20 positive Ramos cells as targets. The EC$_{50}$ values and fold change are presented in Table 11.
Figure 25A:
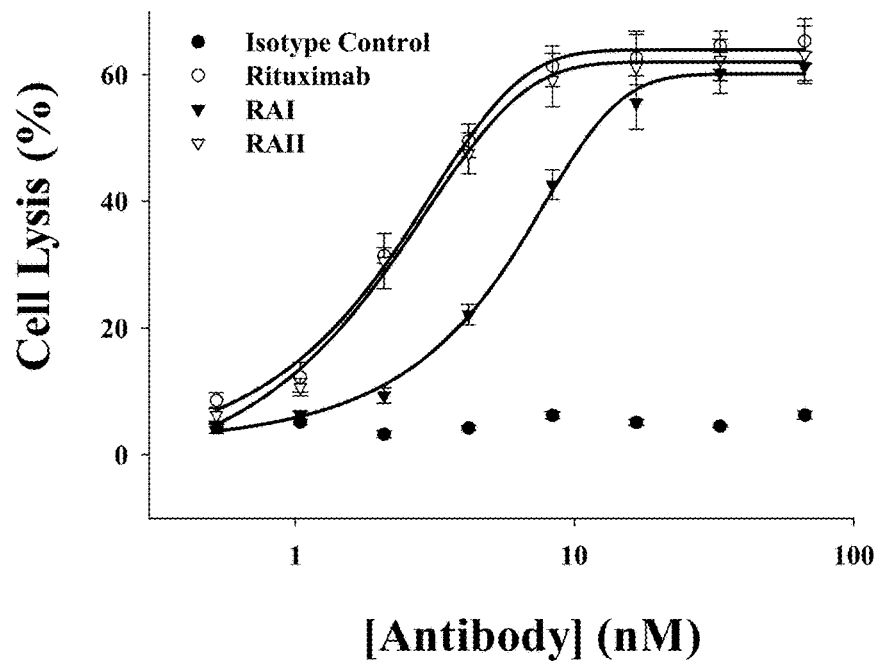
FIGS. 25A-D. CDCC assay of IgG variants using CD20 positive Raji cells as targets and PBMC (FIG. 25A) or PMN (FIG. 25B) or using CD20 positive Ramos cells as targets and PBMC (FIG. 25C) or PMN (FIG. 25D). The EC$_{50}$ values and fold change are presented in Table 12.
Figure 25B:
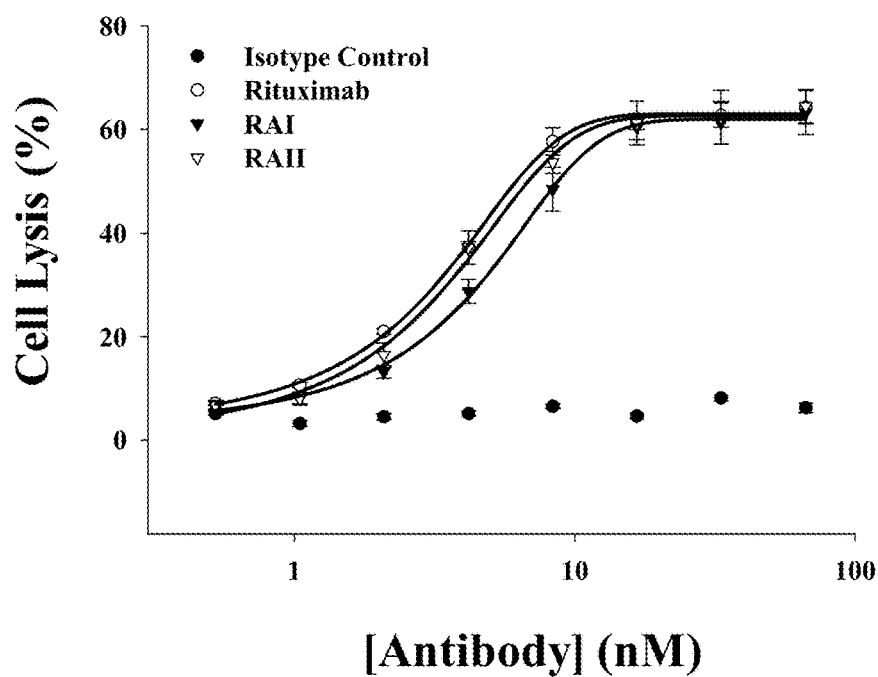
Figure 25C:
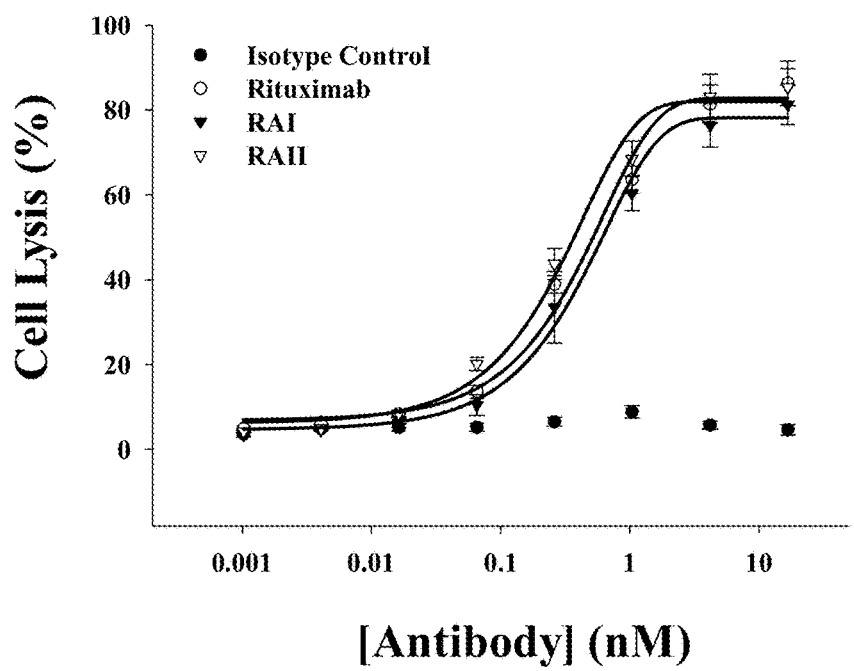
Figure 25D:
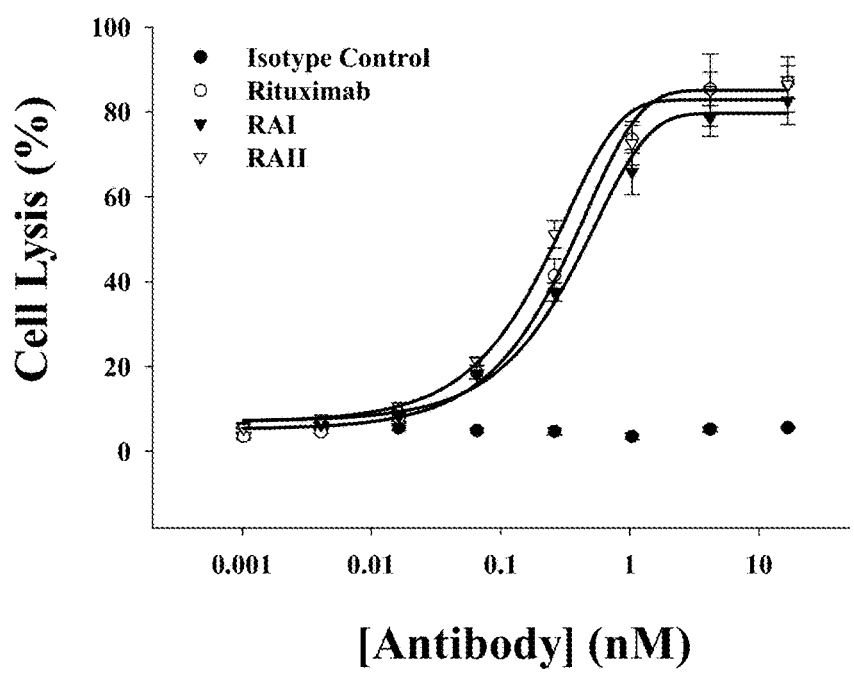

CDC assay of IgG variants (data correspond to FIGS. 12 and 24)

|  | Raji cells | | Ramos cells | |
| --- | --- | --- | --- | --- |
|  | $EC_{50}$ (nM) | Fold | $EC_{50}$ (nM) | Fold |
| Isotype Control |  |  | No Response |  |
| Rituximab | 34.15 ± 2.29 | 1 | 0.92 ± 0.08 | 1 |
| RAI | 9.05 ± 0.90 | 3.77 | 0.46 ± 0.02 | 2.0 |
| RAII | 4.48 ± 0.26 | 7.62 | 0.16 ± 0.01 | 5.7 |
| RAIII | 7.35 ± 0.22 | 4.64 | Not tested |  |

Figure 14:
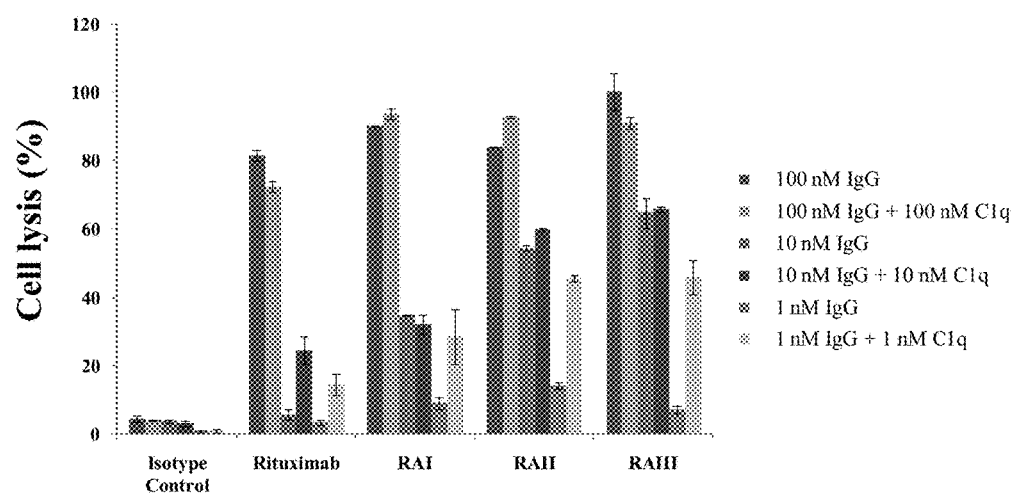
FIG. 14. CDC assay of preincubated IgG variants with C1q using normal human serum and CD20 positive Raji cells as targets. The columns for each IgG variant represent, from left to right, 100 nM IgG, 100 nM IgG+100 nM C1q; 10 nM IgG, 10 nM IgG+10 nM C1q; 1 nM IgG; and 1 nM IgG+1 nM C1q.
Figure 15A:
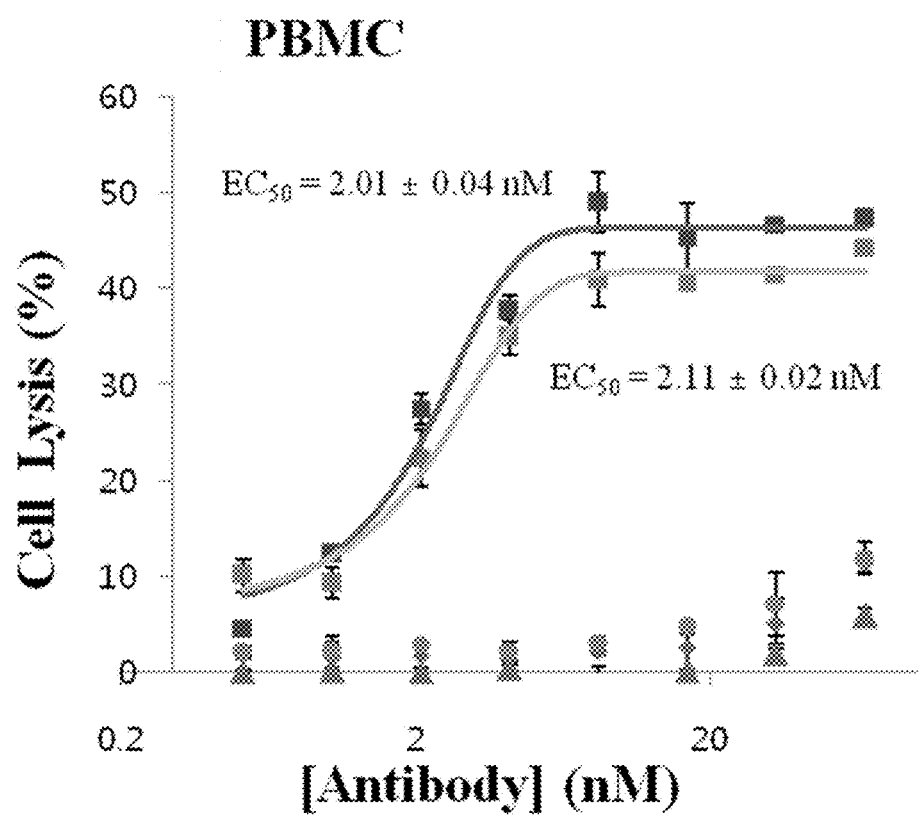
FIGS. 15A-B. ADCC assay of IgG variants using CD20 positive Raji cells as targets and PBMC (FIG. 15A) or PMN (FIG. 15B). Triangles: Isotype control; Light gray squares: Rituximab; Diamonds: RAI; Circles; RAII; Dark gray squares: RAIII FIG. 16. Whole blood assay of IgG variants using normal human blood and CD20 positive Raji cells as targets. The columns for each IgG concentration represent, from left to right, Isotype control, Rituximab, RAI, RAII, and RAIII FIG. 17. Evaluation of the in vivo efficacy of Rituximab and RAII in NOD SCID IL2R$^{-/-}$ mice with Raji cells.
Figure 15B:
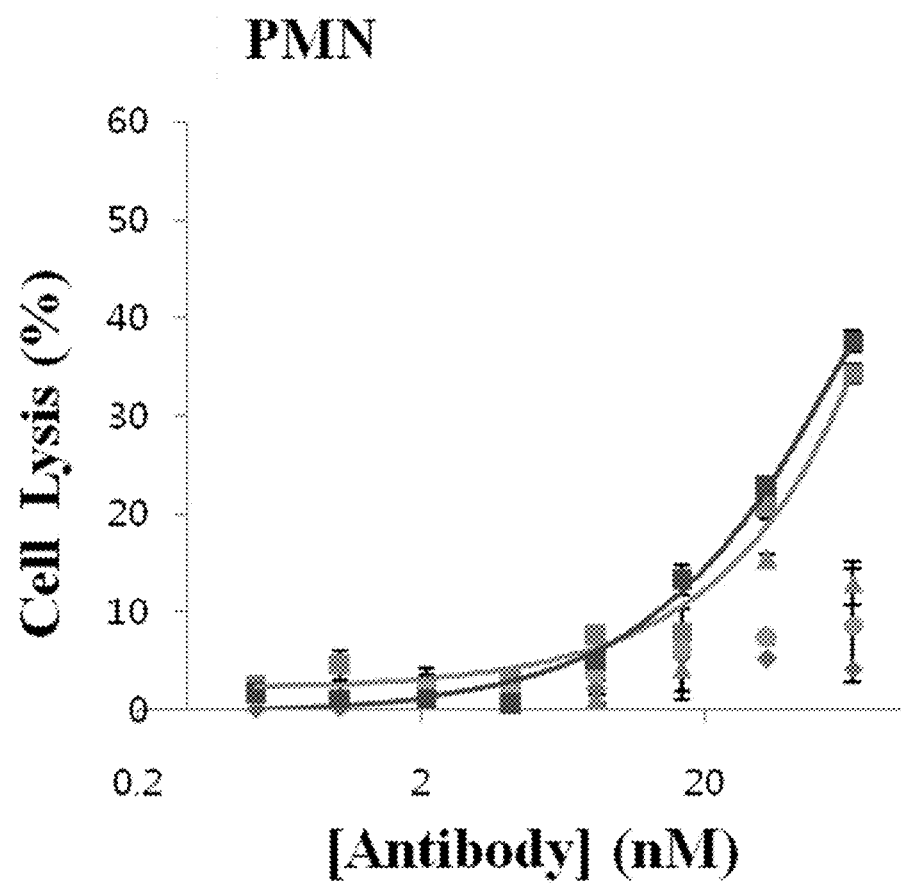

CDC Assay of Preincubated IgG with C1q:

IgG circulates with complement proteins in human blood. Therefore, CDC activities of RA I and RA II were measured after preincubation with the same molar C1q proteins at room temperature for 1 h. As results in FIG. 14 show, preincubation of IgG variants and C1q did not show significant differences when IgG alone had approximately over 40% killing activities. However, while IgG alone had below 20% killing activity, the preincubation increased their efficacies significantly. Preincubation of RA I or RA II variants with C1q showed high cell lysis compared to no-preincubation with C1q only at lower antibody concentrations.

Example 13—Antibody-Dependent Cell Cytotoxicity Assay for the Killing of Cancer Cells by IgG Variants ADCC Assay:

Human peripheral blood mononuclear cell (PBMC) and polymorphonuclear leukocytes (PMN) were isolated from human blood from healthy donor on the day prior to the ADCC assay. 50 mL of human blood was collected in heparinized vials (BD biosciences) and mixed well by gently inverting the tube several times. 25 mL of blood was layered over 25 mL of room temperature Ficoll Histopaque (Invitrogen) in a 50 mL conical tube. The tubes were centrifuged at 2,500 rpm for 30 min in a swing-bucket rotor without brakes. The human PBMCs were aspirated in the interphase between histopaque and medium, and the human PMN were collected from the pellet. Both human PBMC and PMN were resuspended with red blood cell (RBC) lysis buffer (155 mM $NH_4Cl$, 12 mM $NaHCO_3$, and 0.1 mM EDTA), and washed twice with PBS. The isolated human PBMCs or PMNs were mixed with calcein AM-labeled Raji cells and various concentrations of IgG variants in 96-well plates. The PMNs were activated by 10 ng/mL of GM-CSF (Life Technologies). The ratio of tumor versus effector cell was 1:10 and the plates incubated at 37° C. with 5% $CO_2$ for 4 h. The quantities of lysed tumor cells were detected by the same method using a CDC assay. The percent of tumor cell lysis was calculated according to the following formula: 100×(E−S)/(M−S), where E is the fluorescence of the experimental well, S is that in the absence of antibody (tumor cells were incubated with medium and effector cells), and M is that of tumor cells with lysis buffer. As described in Example 7, RAI and RAII did not show any ADCC activities with PBMC or PMN because they did not have affinities for FcγRs (FIGS. 9A-D and 15A-B). But RAIII has affinity for FcγRs, except FcγRIIb, thus, RAIII showed almost the same ADCC activities as Rituximab (FIGS. 11A-F and 15A-B). The $EC_{50}$ value in PBMC of RAIII was 2.01±0.02 nM and the $EC_{50}$ value in PBMC of Rituximab was 2.11±0.02 nM.

Example 14—Complement-Dependent Cell Cytotoxicity Assay for the Killing of Cancer Cells Human peripheral blood mononuclear cell (PBMC) and polymorphonuclear leukocytes (PMN) were isolated from human blood from a healthy donor on the day prior to the CDCC and CMC assays. In the presence of serum and immune cells, antibody can activate ADCC and complement-mediated cytotoxicity (CMC) which is the result of cell lysis due to both CDC and due to complement dependent cell cytotoxicity (CDCC). Since C1q-specific IgG variants do not exhibit ADCC activity they can induce only CMC. Additionally the effectiveness of CDCC alone in the absence of cell lysis (due to the formation of the terminal complement complex TCC) can be determine using C9-depleted serum. The C9 protein is critical for the formation of TCC and in its absence, cell lysis by antibodies that do not bind to Fc receptors can only occur via CDCC. For CDCC assays, CD20+ cancer cells were incubated with antibody, 25% C9-depleted serum, and PBMC or polymorphonuclear (PMN) cells. PMNs were activated by 10 ng/mL of GM-CSF (Life Technologies). The ratio of tumor versus effector cell was 1:10 and the plates incubated at 37° C. with 5% $CO_2$ for 4 hours. The quantities of lysed tumor cells were detected by same method used for CDC assays as in Example 12. The percent of tumor cell lysis was calculated according to the following formula: 100×(E−S)/(M−S), where E is the fluorescence of experimental well, S is that in the absence of antibody (tumor cells were incubated with medium and effector cells), and M is that of tumor cells with lysis buffer. With C9-depleted serum and immune cells, RAI and RAII activate only CDCC but Rituximab can activate both of ADCC and CDCC. RAI and RAII showed the similar tumor-cell killing activities by CDCC with Rituximab by ADCC and CDCC in Raji and Ramos cells (FIGS. 25A-D; Table 12).

TABLE 12

CDCC and CMC assays of IgG variants (data correspond to FIGS. 25A-D)

| | | CDCC (or ADCC + CDCC) | | | |
|---|---|---|---|---|---|
| Condition | Serum | | | C9-depleted serum | |
| | Cancer Cell | Raji | | Ramos | |
| | Effector Cell | PBMC | PMN | PBMC | PMN |
| $EC_{50}$ (nM) in Raji cell/ Increasing Fold | Isotype Control | No Response | | | |
| | Rituximab | 2.46 ± 0.14 | 1.90 ± 0.11 | 0.43 ± 0.03 | 0.32 ± 0.02 |
| | RAI | 6.24 ± 0.27/ 0.39 | 3.34 ± 0.24/ 0.57 | 0.45 ± 0.03/ 0.95 | 0.37 ± 0.02/ 0.86 |
| | RAII | 2.56 ± 0.18/ 0.96 | 2.10 ± 0.15/ 0.90 | 0.30 ± 0.02/ 1.43 | 0.22 ± 0.01/ 1.45 |

Example 15—Complement-Dependent Cell Phagocytosis Assay for the Killing of Cancer Cells by the Selected IgG Variants PBMCs were purified from fresh human blood by Histopaque density gradient centrifugation, and CD14+ monocytes were isolated by magnetic bead separation. Monocytes were differentiated into macrophages by culturing for 7 days in RPMI medium containing 15% FBS and 50 ng/ml GM-CSF and then were mixed at a 10:1 effector:tumor cell ratio with Calcein-labeled Raji cells and antibodies as shown. For complement dependent cell phagocytosis (CDCP) assays, Raji cells were incubated with 25% C9-depleted serum, antibodies and macrophages. After 2 hr at 37° C., the cells were labeled with anti-CD11b-APC and anti-CD14-APC. Phagocytosis was evaluated by FACS on an LSRFortessa (BD Bioscience), and reported as the fraction of double positive cells over the total number of tumor cells in the sample. RAI and RAII could induce CDCP and showed better tumor cell-engulfing activities than Rituximab, which can induce both of the ADCP and CDCP. The $EC_{50}$ of RAI is 4.61±0.05 nM, an increase of 3.78-fold over wild-type Rituximab in Raji cells. The $EC_{50}$ of RAII is 3.72±0.04 nM, an increase of 4.69-fold over wild-type Rituximab in Raji cells (FIG. 26; Table 13).

TABLE 13

Figure 26:
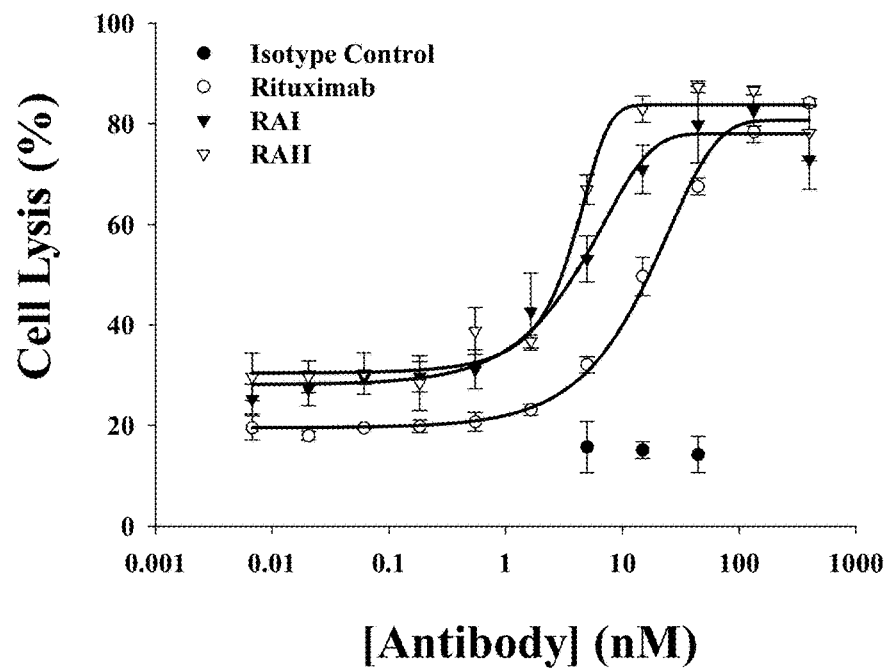
FIG. 26. CDCP assay of IgG variants using CD20 positive Raji cells as targets and Ml-macrophage. The EC$_{50}$ values and fold change are presented in Table 13.
Figure 27A:
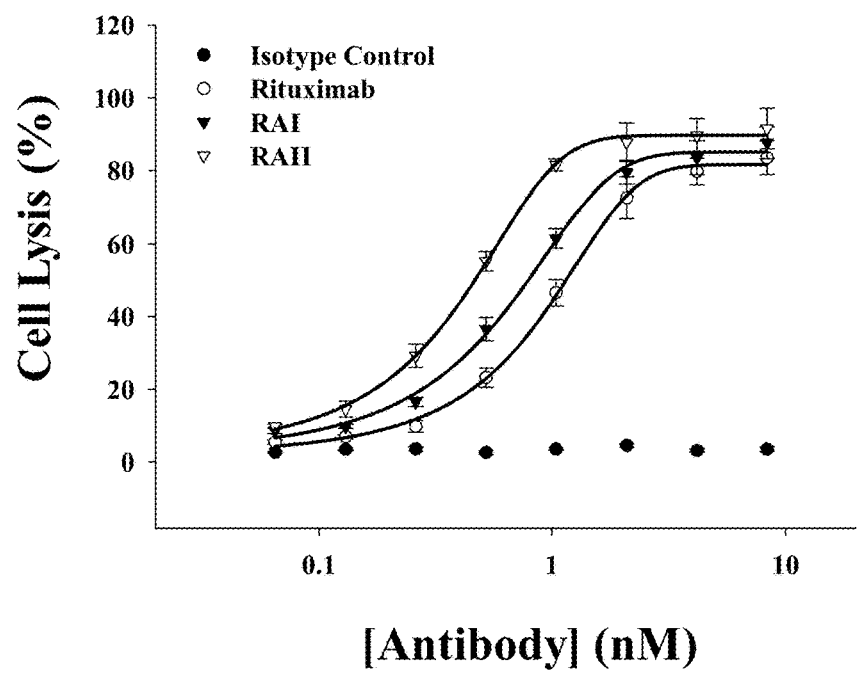
FIGS. 27A-D. CMC assay of IgG variants using CD20 positive Raji cells as targets and PBMC (FIG. 27A) or PMN (FIG. 27B) or using CD20 positive Ramos cells as targets and PBMC (FIG. 27C) or PMN (FIG. 27D). The EC$_{50}$ values and fold change are presented in Table 14.
Figure 27B:
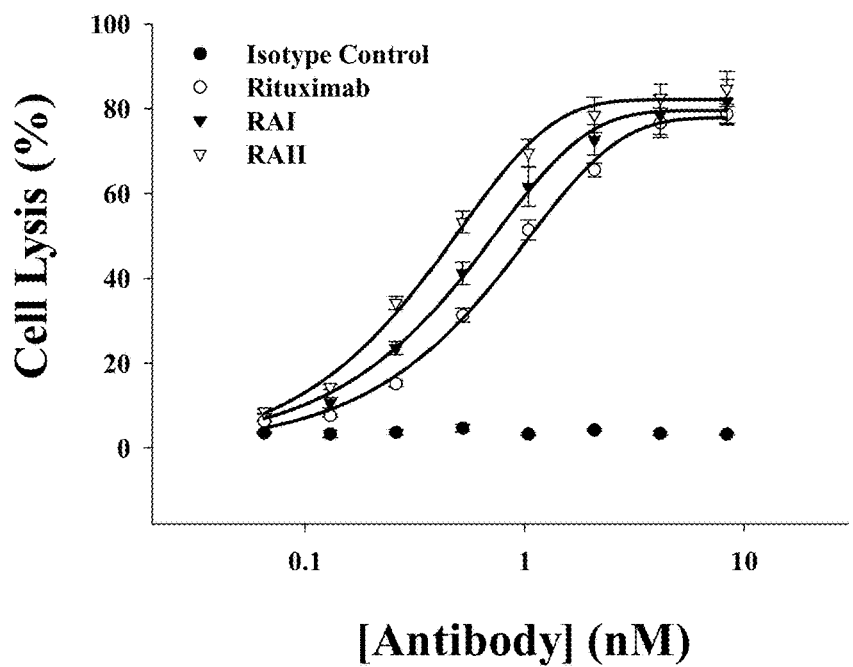
Figure 27C:
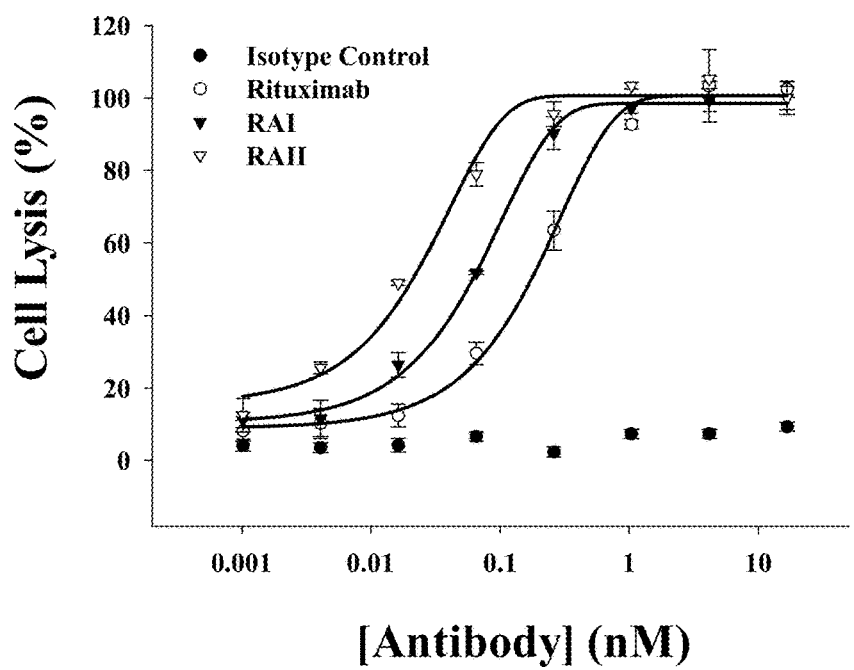
Figure 27D:
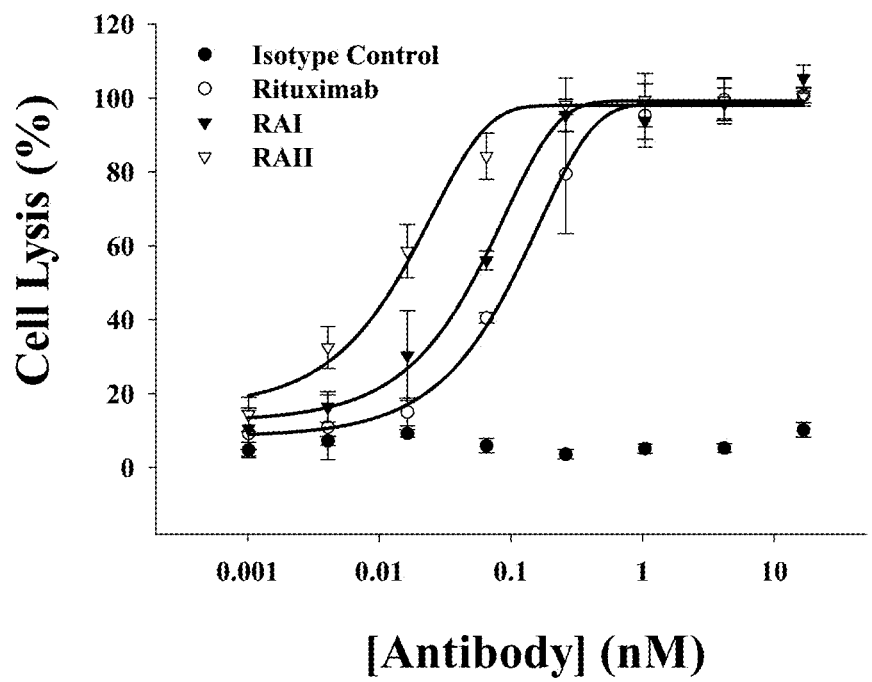

CDCP assays of IgG variants (data correspond to FIG. 26)

| | EC50 (nM) | Fold |
|---|---|---|
| Isotype Control | No Response | |
| Rituximab | 17.44 ± 0.18 | 1 |
| RAI | 4.61 ± 0.05 | 3.78 |
| RAII | 3.72 ± 0.04 | 4.69 |

Example 16—Complement-Mediated Cytotoxicity Assay for the Killing of Cancer Cells Human peripheral blood mononuclear cell (PBMC) and polymorphonuclear leukocytes (PMN) were isolated from human blood from a healthy donor on the day prior to CDCC, and CMC assays. For CMC assays, cancer cells incubated with antibody, 25% pooled human serum (PHS), and PBMC (or PMN). The PMNs were activated by 10 ng/mL of GM-CSF (Life Technologies). The ratio of tumor versus effector cell was 1:10 and the plates incubated at 37° C. with 5% $CO_2$ for 4 hours. The quantities of lysed tumor cells were detected by same method with CDC assay. With PHS and immune cells, RAI and RAII can mediate only CMC whereas Rituximab can mediate cell killing by all effector functions, ADCC in addition to CMC. RAI and RAII showed enhanced $EC_{50}$ values with Raji and Ramos cells with PBMC or PMN. RAI showed 1.4-fold enhanced $EC_{50}$ values with Raji using PBMC as effector cells, 1.3-fold enhanced $EC_{50}$ values with Raji cells using with PMNs as effector cells and 2.7-fold enhanced $EC_{50}$ values with Ramos cells using PBMC, and 1.8-fold enhanced $EC_{50}$ values with Ramos and PMN (all compared to rituximab). RAII also showed 2.1-fold enhanced $EC_{50}$ values with Raji and PBMC as effectors, 1.9-fold enhanced $EC_{50}$ values with Raji and PMN, 6.9-fold enhanced $EC_{50}$ values with Ramos and PBMC, and 6.1-fold enhanced $EC_{50}$ values with Ramos and PMN, all relative to Rituximab (FIGS. 27A-D; Table 14).

TABLE 14

CMC assays of IgG variants (data correspond to FIGS. 27A-D)

| | | CMC (or ADCC + CMC) | | | |
|---|---|---|---|---|---|
| Condition | Serum | PHS | | | |
| | Cancer Cell | Raji | | Ramos | |
| | Effector Cell | PBMC | PMN | PBMC | PMN |
| $EC_{50}$ (nM) in Raji cell/ Increasing Fold | Isotype Control | No Response | | | |
| | Rituximab | 0.98 ± 0.07 | 0.78 ± 0.02 | 0.20 ± 0.01 | 0.11 ± 0.01 |
| | RAI | 0.70 ± 0.03/ 1.4 | 0.58 ± 0.05/ 1.3 | 0.073 ± 0.005/ 2.7 | 0.061 ± 0.004/ 1.8 |
| | RAII | 0.46 ± 0.02/ 2.1 | 0.41 ± 0.02/ 1.9 | 0.029 ± 0.002/ 6.9 | 0.018 ± 0.001/ 6.1 |

Figure 16:
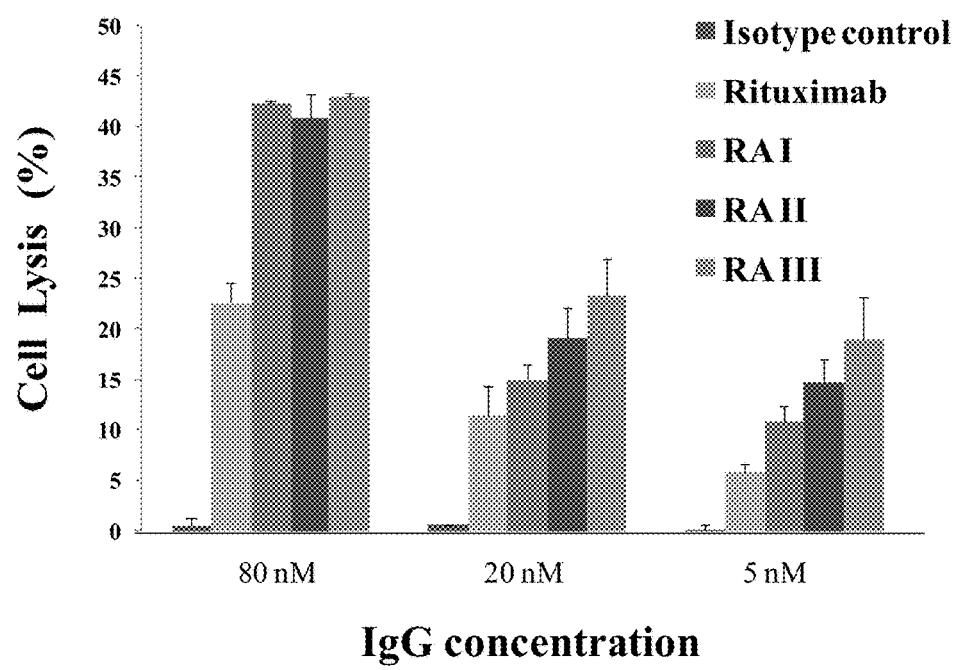

Example 17—Whole Blood Assay for the Killing of Cancer Cells by Complement Binding Enhanced IgG Variants Whole blood from healthy donor was incubated with IgG variants and calcein AM-labeled Raji cells in 96-well plates at 37° C. with 5% $CO_2$ for 4 h. The tumor cell killing activities were measured by the same CDC assay as in Example 8. The percent of tumor cell lysis was calculated using same formula as in Example 8. As shown in FIG. 16, CDC efficacy of RAI and RAII showed better tumor cell killing activities than Rituximab even though the latter mediates ADCC and CDC in a concentration-dependent manner. RAIII, which can induce both ADCC and CDC, also showed higher tumor cell lysis activities than Rituximab.

Figure 28A:
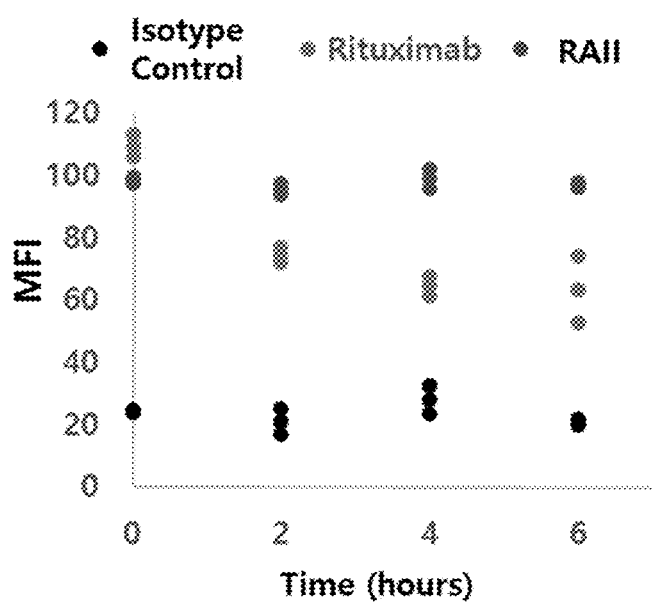
FIGS. 28A-B. FcγRIIb-mediated internalization assay in TMD8 (FIG. 28A) or and HBL-1 (FIG. 28B). The tumor cell surface bound antibodies were detected by anti-human Fc-FITC after incubation with tumor cells for 0, 2, 4, and 6 hrs.
Figure 28B:
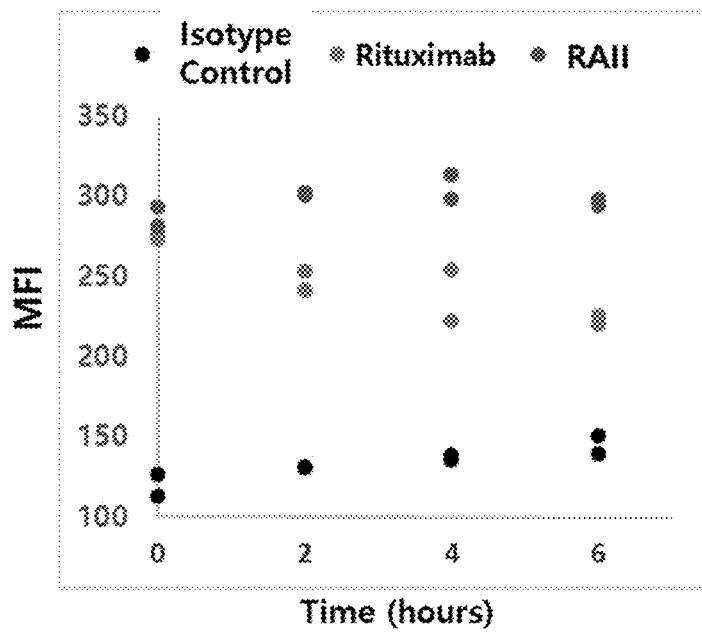
Figure 29:
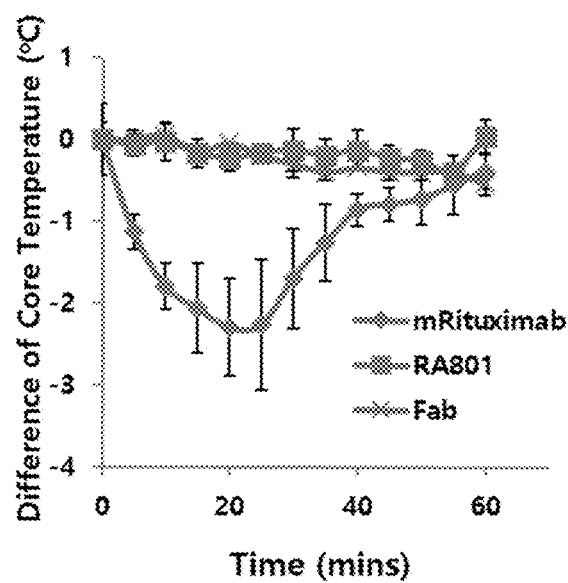
FIG. 29. Anaphylaxis assay in C57BL/6J mice. Heat aggregated antibodies were injected into mice (n=3) and the core temperature was detected every five minutes.

Example 18—CD20 and FcγRIIB-Mediated Internalization Assay by the Selected IgG Variants The co-ligation of Rituximab with FcγRIIB and CD20 induces the internalization of the CD20-antibody complex, which is followed by degradation of the CD20 ligand by the endolysosomal pathway. This mechanism results in reduction of CD20 expression on target cells and is considered to be a critical mechanism for cancer cell resistance to rituximab. The internalization of CD20-positive in TMD8 (a human ABC-DLBCL cell line) and in HBL-1 (a Human diffuse large B-cell lymphoma) cells was evaluated. TMD8 and HBL-1 cells were cultured in RPMI 1640 medium (Invitrogen, USA) supplemented with 10% FBS (Invitrogen, USA) and then cells were incubated with isotype control, Rituximab, or RAII for 0, 2, 4, or 6 hrs. The level of cell-surface bound antibodies was detected by goat anti-human Fc with FITC (Abcam). Rituximab showed the decreasing MFI values as a function of time for both cell lines. In contrast, incubation with RAII resulted in no CD20 internalization in the target cells, which thus showed similar MFI values at all time points for both cell lines (FIG. 28A-B). These experiments were repeated three times independently.

Example 19—Anaphylaxis Assays

All animal experiments were performed under a protocol approved by institutional Animal Care and Use Committee of the University of Texas at Austin (heat-aggregation of protein here). Immune complexes may cause an anaphylaxis response, mediated by FcγRs-expressing cells. To evaluate anaphylaxis responses immune complexes were formed by heat aggregated Fabs as negative control were prepared, as well as by murine Rituximab as positive control, and also by RAII by incubation at 63° C. for 1 hr. 600 µg of each heat aggregated antibody was injected into C57BL/6J mice (n=3) (The Jackson Laboratory) intravenously. One of the common symptom of an anaphylaxis response is decreasing body temperature. Therefore, mouse core body temperature was measured using rectal thermoprobe every 5 minutes. For the mRituximab-treated mice, core body temperature decreased about 2.4° C. for the first 20 minutes and gradually recovered to 38° C. In contrast, RAII-treated mice did not show any change of core body temperature like Fab because RAII does not bind to FcγRs.

Example 20—Evaluation of In Vivo Anti-Tumor Efficacy by RAII

Figure 17:
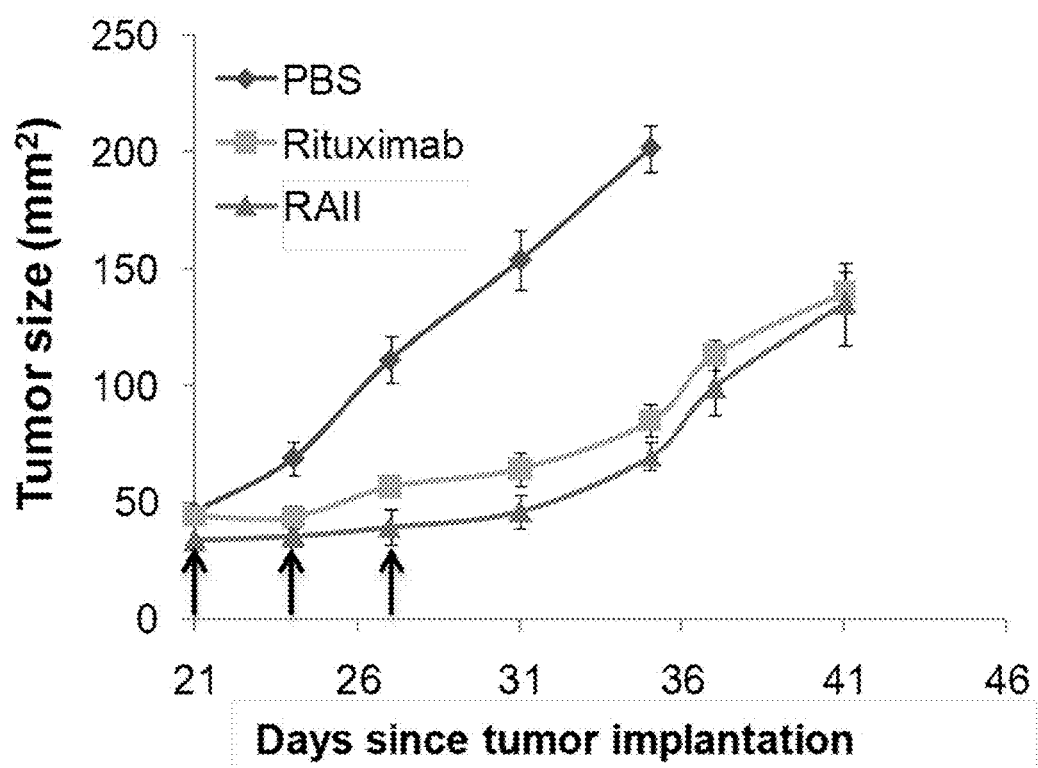
Figure 18A:
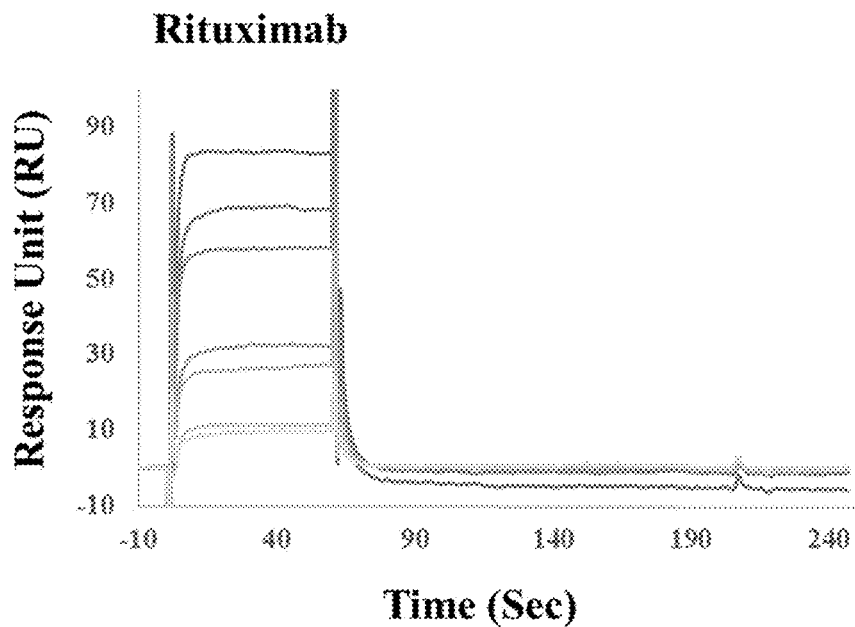
FIGS. 18A-D. SPR results of RAI and RAII to FcRn at pH 6.0 or pH 7.4.
Figure 18B:
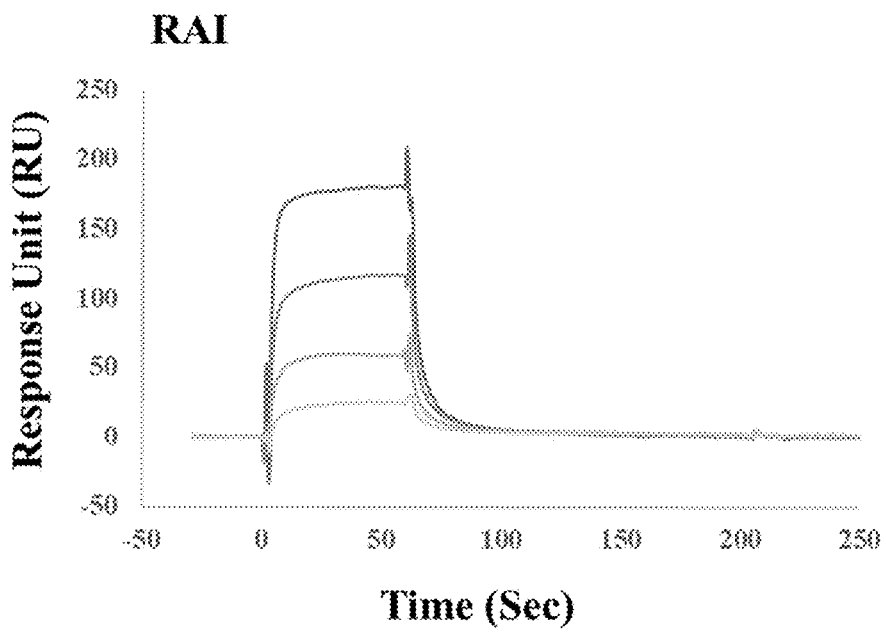
Figure 18C:
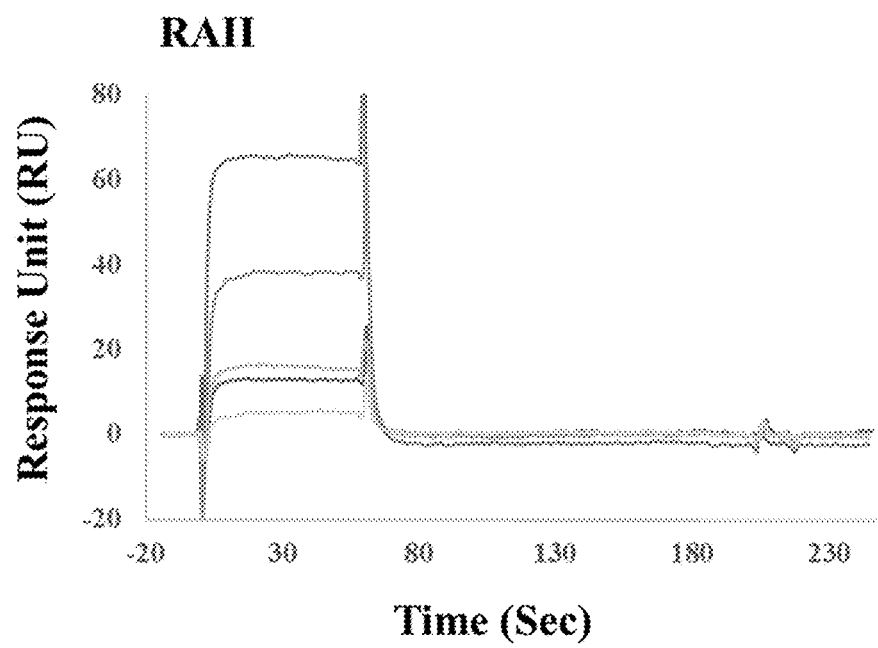
Figure 18D:
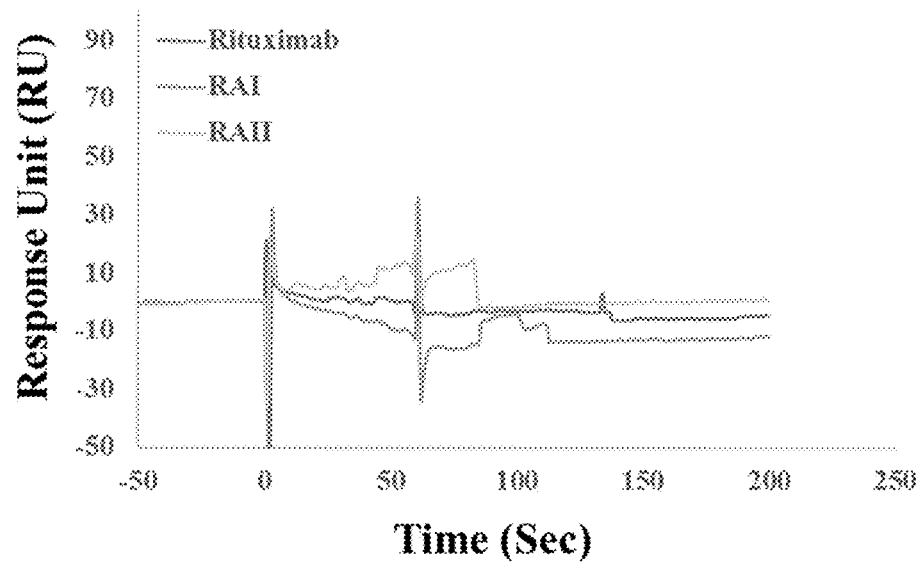

The in vivo anti-tumor efficacy of RAII was evaluated in a xenograft model with Raji and Ramos cells. Cells were cultured in RPMI 1640 medium (Life Technologies) with 10% fetal bovine serum (Life Technologies), penicillin, and streptomycin. Then $2.5 \times 10^5$ Raji cells in 200 µL RPMI 1640 medium with 50% Matrigel (BD bioscience) were injected subcutaneously in the right flank of each NOD-SCID $IL2R^{-/-}$ mouse (n=3). Tumor development was determined by caliper measurement. When the average tumor size was 50 $mm^2$ (day 21), PBS, Rituximab, and RAII were administered by intraperitoneal (i.p.) injection of a single dose of 400 µg antibody per mouse (20 mg/kg) at Day 21, Day 24, and Day 27. Tumors were measured at least twice per week using calipers until a tumor volume of 200 $mm^2$. RAII significantly inhibited tumor growth compared to PBS (one-way ANOVA; p<0.0005), and RAII showed anti-tumor activities comparable to Rituximab despite the complete lack of ADCC (FIG. 17).

Figure 30:
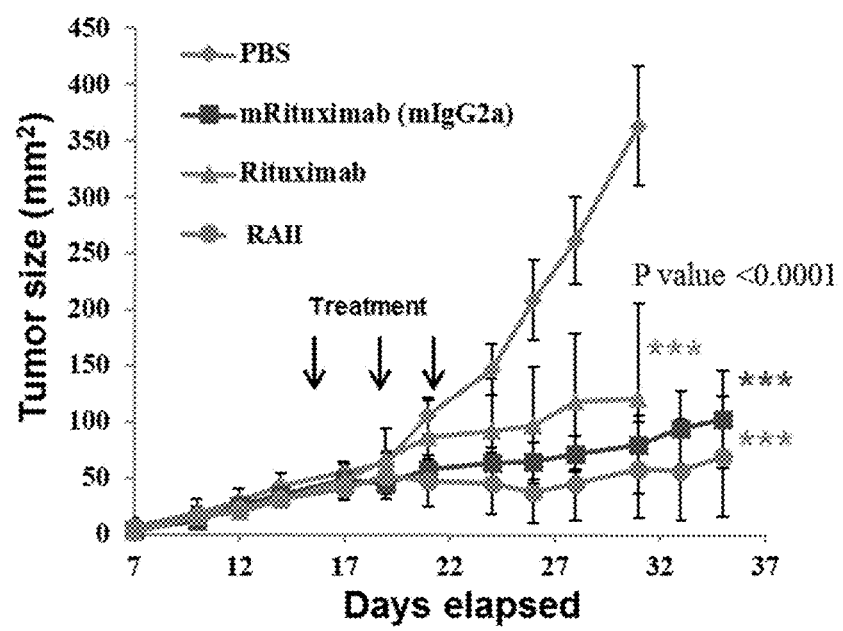
FIG. 30. Evaluation of the in vivo efficacy of RAII in nude mice with Ramos cells.

Next, $1 \times 10^6$ Ramos cells in 200 µL RPMI 1640 medium with 50% Matrigel (BD bioscience) were injected subcutaneously in the right flank of each Athymic nude mice (n=6, The Jackson Laboratory). Administration of antibodies or PBS was started when the tumor area size reached to 10-50 $mm^2$, and repeated total three times at Day 15, Day 18, and Day 21. Tumor diameters were measured every 3-4 days with caliper and tumor areas calculated by the formula (length)×(width)×π, respectively. Mice were euthanized when the tumor size reached 2500 $mm^3$ in volume. RAII significantly inhibited tumor growth compared to PBS (one-way ANOVA; p<0.00001), and RAII showed better anti-tumor activities than mRituximab despite the complete lack of ADCC (FIG. 30).

TABLE 15

Primers used in this study (provided as SEQ ID NOs: 24-35)

| SEQ ID NO: | Primer Name | Primer nucleotide sequence (5'→3') |
|---|---|---|
| 24 | PCH016 | GTTATTACTCGCGGCCCAGCCG |
| 25 | PCH017 | GGGGAAGAGGAAGACTGACGGN (A10% T70% G10% C10%)N (A10% T10% G10% C70%)N (A10% T10% G10% C70%)N (A10% T10% G10% C70%)N (A10% T10% G10% C70%)N (A10% T10% G10% C70%)N (A70% T10% G10% C10%)N (A10% T10% G70% C10%)N (A10% T10% G70% C10%)N (A70% T10% G10% C10%)N (A10% T10% G70% C10%)N (A10% T70% G10% C10%)N (A10% T70% G10% C10%)N (A10% T10% G10% C70%) AGGTGCTGGGCACGGTGGG |
| 26 | PCH018 | CCGTCAGTCTTCCTC TTCCCC |
| 27 | PCH019 | GGTTTTCTCGATGGG GGCTGGG |
| 28 | PCH020 | CCCAGCCCCCATCGAGAAAACCN (A70% T10% G10% C10%)N (A10% T70% G10% C10%)N (A10% T10% G10% C70%)N (A10% T70% G10% C10%)N (A10% T10% G10% C70%)N (A10% T10% G10% C70%)N (A70% T10% G10% C10%)N (A70% T10% G10% C10%)N (A70% T10% G10% C10%)N (A10% T10% G70% C10%)N (A10% T10% G10% C70%)N (A10% T10% G10% C70%)N (A70% T10% G10% C10%)N |

TABLE 15-continued

Primers used in this study
(provided as SEQ ID NOs: 24-35)

| SEQ ID NO: | Primer Name | Primer nucleotide sequence (5'→3') |
|---|---|---|
| | | (A70% T10% G10% C10%)N |
| | | (A70% T10% G10% C10%)N |
| | | (A10% T10% G70% C10%)N |
| | | (A10% T10% G70% C10%)N |
| | | (A10% T10% G70% C10%)N |
| | | (A10% T10% G70% C10%)N |
| | | (A70% T10% G10% C70%)N |
| | | (A70% T10% G10% C10%)N |
| | | (A10% T10% G70% C10%)N |
| | | (A10% T10% G10% C70%)N |
| | | (A10% T10% G10% C70%)N |
| | | (A10% T10% G10% C70%)N |
| | | (A10% T10% G70% C10%)N |
| | | (A70% T10% G10% C10%)N |
| | | (A10% T10% G70% C10%)N |
| | | (A70% T10% G10% C10%) CCACAGGTGTACACCCTGCCC |
| 29 | PCH021 | CGGCCGCGAATTCGGCCCC |
| 30 | PCH022 | GGGGAAGAGGAAGACTGACGG |
| 31 | PCH023 | GGTTTTCTCGATGGGGCTGGG |
| 32 | PCH001 | CACCAAGGTCGACAAGAAAGTTG |
| 33 | TH084 | CTCGAGCGGCCGCTCATTTACCC GGGGACAGGGAGAGGTTTACCCG GGGACAGGGAGAGG |
| 34 | WK68 | GCCGCGGGAGGAGCAGTACAACA GCCTGTACCGTGTGG |
| 35 | WK69 | GTGAGGACGCTGACCACACGGTA CAGGCTGTTGTACTGCTC |

TABLE 16

Plasmids used in this study

| Plasmids | Relevant characteristics | Reference or Source |
|---|---|---|
| pMopac12-pelB-IgG-VH-CH1-CH2-CH3-FLAG | Bacterial display vector containing IgG VH1-CH1-CH2 and CH3 domains of trastuzumab | Jung et al., 2012 |
| pBAD30-PelB-VL-Ck-NlpA-VL-Ck-His-cMyc | Bacterial display vector containing IgG VL-Ck domains of trastuzumab | Jung et al., 2012 |
| pBAD33-NlpA-PA domain 4-His | Bacterial display vector containing PA domain 4 | Leysath et al., 2009 |
| pMAZ IgH M18 | Mammalian expression vector containing M18 heavy chain | Leysath et al., 2009 |
| pMAZ IgL M18 | Mammalian expression vector containing M18 light chain | Leysath et al., 2009 |
| pMaz-IgH-FcγRI-His | FcγRI gene in pMaz-IgH for monomeric mammalian expression | Jung et al., 2012 |
| pMaz-IgH-FcγRIIa$_{H131}$-GST | FcγRIIa$_{H131}$ gene in pMaz-IgH for dimeric mammalian expression | Jung et al., 2012 |
| pMaz-IgH-FcγRIIa$_{R131}$-GST | FcγRIIa$_{R131}$ gene in pMaz-IgH for dimeric mammalian expression | Jung et al., 2012 |
| pMaz-IgH-FcγRIIb-GST | FcγRIIb gene in pMaz-IgH for dimeric mammalian expression | Jung et al., 2012 |
| pMaz-IgH-FcγRIIIa$_{V157}$-GST | FcγRIIIa$_{V157}$ gene in pMaz-IgH for dimeric mammalian expression | Jung et al., 2012 |
| pMaz-IgH-FcγRIIIa$_{F157}$-GST | FcγRIIIa$_{F157}$ gene in pMaz-IgH for dimeric mammalian expression | Jung et al., 2012 |
| pMaz-IgH-FcγRIIIa$_{V157}$-Streptavidin | FcγRIIIa$_{V157}$ gene in pMaz-IgH for tetrameric mammalian expression | This study |
| pMaz-IgH-FcRn-β2m-GST | FcRn-β2m gene in pMaz-IgH for dimeric mammalian expression | This study |
| pcDNA3.4-IgH-Rituximab | Mammalian expression vector containing Rituximab heavy chain | This study |
| pcDNA3.4-IgL-Rituximab | Mammalian expression vector containing Rituximab light chain | This study |
| pcDNA3.4-IgH-RGI | Mammalian expression vector containing RGI heavy chain | This study |
| pcDNA3.4-IgH-RGII | Mammalian expression vector containing RGII heavy chain | This study |
| pcDNA3.4-IgH-RGIII | Mammalian expression vector containing RGIII heavy chain | This study |
| pcDNA3.4-IgH-RAI | Mammalian expression vector containing RAI heavy chain | This study |
| pcDNA3.4-IgH-RAII | Mammalian expression vector containing RAII heavy chain | This study |

TABLE 16-continued

Plasmids used in this study

| Plasmids | Relevant characteristics | Reference or Source |
|---|---|---|
| pcDNA3.4-IgH-RAIII | Mammalian expression vector containing RAIII heavy chain | This study |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913
U.S. Pat. No. 4,683,195
U.S. Pat. No. 4,683,202
U.S. Pat. No. 4,714,682
U.S. Pat. No. 4,767,206
U.S. Pat. No. 4,774,189
U.S. Pat. No. 4,800,159
U.S. Pat. No. 4,857,451
U.S. Pat. No. 4,883,750
U.S. Pat. No. 4,938,948
U.S. Pat. No. 4,988,618
U.S. Pat. No. 4,989,977
U.S. Pat. No. 5,021,236
U.S. Pat. No. 5,160,974
U.S. Pat. No. 5,302,523
U.S. Pat. No. 5,322,783
U.S. Pat. No. 5,384,253
U.S. Pat. No. 5,464,765
U.S. Pat. No. 5,478,722
U.S. Pat. No. 5,538,877
U.S. Pat. No. 5,538,880
U.S. Pat. No. 5,550,318
U.S. Pat. No. 5,563,055
U.S. Pat. No. 5,567,326
U.S. Pat. No. 5,580,859
U.S. Pat. No. 5,589,466
U.S. Pat. No. 5,610,042
U.S. Pat. No. 5,656,610
U.S. Pat. No. 5,702,932
U.S. Pat. No. 5,736,524
U.S. Pat. No. 5,779,907
U.S. Pat. No. 5,780,448
U.S. Pat. No. 5,789,215
U.S. Pat. No. 5,824,520
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,882,864
U.S. Pat. No. 5,912,148
U.S. Pat. No. 5,916,776
U.S. Pat. No. 5,916,779
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,624
U.S. Pat. No. 7,094,571
U.S. Pat. No. 7,094,571
U.S. Patent Publ. 20030180937
U.S. Patent Publ. 20030219870
U.S. Patent Publ. 20050260736
U.S. Patent Publ. 20060173170
U.S. Patent Publ. 20080292646
Abbondanzo et al., *Breast Cancer Res. Treat.*, 16:182(151), 1990.
Ahouse et al., *J. Immunol.*, 151:6076-6088, 1993.
Allen and Seed, *Nucleic Acids Res.*, 16:11824, 1988.
Andersen et al., *Eur. J. Immunol.*, 36:3044-3051, 2006.
Andersen et al., *Eur. J. Immunol.*, 36:3044-3051, 2006.
Antibodies: A Laboratory Manual, Cold Spring Harbor Laboratory, 1988
Atherton et al., *Biol. Reprod.*, 32(1):155-171, 1985.
Ausubel et al., In: *Current Protocols in Molecular Biology*, John, Wiley & Sons, Inc, N Y, 1994.
Baneyx and Mujacic, *Nat. Biotechnol.*, 22:1399-1408, 2004.
Bellus, *J. Macromol. Sci. Pure Appl. Chem.*, A31(1): 1355-1376, 1994.
Berntzen et al., *J. Immunol. Methods*, 298:93-104, 2005.
Better et al., *Science*, 240: 1041-10433, 1988.
Bocek and Pecht, *FEBS Lett.*, 331, 86-90, 1993.

Boeke et al., *Mol. Gen. Genet.*, 186, 1982.
Bolland and Ravetch, *Adv. Immunol.*, 72:149-177, 1999.
Borrok et al., *ACS Chem. Biol.*, 7:1596-1602, 2012.
Boruchov et al., *J. Clin. Invest.*, 115:2914-2923, 2005.
Boss et al., *Nucleic Acids Res.*, 12:3791-3806, 1984.
Bowden and Georgiou, *J. Biol. Chem.*, 265:16760-16766, 1990.
Bukau et al., *J. Bacteriol.*, 163:61, 1985.
Burman et al., *J. Bacteriol.*, 112:1364, 1972.
Burton and Burton, *Nat. Rev. Immunol.*, 4:89-99, 2004.
Cabilly et al., *Proc. Natl. Acad. Sci. USA*, 81:3273-3277, 1984.
Carbonelli et al., *FEMS Microbiol Lett.*, 177:75-82. 1999
Chames et al., *Proc. Natl. Acad. Sci. USA*, 97:7969-7974, 2000.
Chen and Okayama, *Mol. Cell Biol.*, 7(8):2745-2752, 1987.
Cocea, *Biotechniques*, 23(5):814-816, 1997.
Collins et al., *Immunogenetics*, 45:440-443, 1997.
Daeron, *Annu. Rev. Immunol.*, 15:203-234, 1997.
Dall'Acqua et al., *J. Immunol.*, 177:1129-1138, 2006.
Daugherty et al., *Protein Eng.*, 12:613 621, 1999.
De Jager et al., *Semin. Nucl. Med.*, 23(2):165-179, 1993.
de Kruif and Logtenberg, *J. Biol. Chem.*, 271:7630-7634, 1996.
Decad and Nikaido, *J. Bacteriol.*, 128:325, 1976.
Desai et al., *Cancer Res.*, 58:2417-2425, 1998.
Dholakia et al., *J. Biol. Chem.*, 264(34):20638-20642, 1989.
Diebolder et al., *Science*, 343:1260-1263, 2014.
Doolittle and Ben-Zeev, *Methods Mol Biol*, 109:215-237, 1999.
Edelman et al., *Proc Natl Acad Sci USA*, 63:78-85, 1969.
Eigenbrot et al., *J. Molec. Biol.*, 229:969-995, 1993.
Elbein et al., *Glycobiology*, 13:17R-27, 2003.
Elvin et al., *Int. J. Pharm.*, 440:83-98, 2013.
European Appln. 320 308
European Appln. 329 822
Fahnestock et al., *J. Bacteriol.*, 167:870-880, 1986.
Farmer et al., *FEMS Microbiol. Lett.*, 176:11, 1999.
Fechheimer, et al., *Proc Natl Acad. Sci. USA*, 84:8463-8467, 1987.
Fraley et al., *Proc. Natl. Acad. Sci. USA*, 76:3348-3352, 1979.
Francisco et al., *Proc. Natl. Acad. Sci. USA*, 90:10444-10448, 1993.
Frohman, In: *PCR Protocols: A Guide To Methods And Applications*, Academic Press, N.Y., 1990.
Fromant et al., *Anal. Biochem.*, 224:347-353, 1995.
Gaboriaud et al., *J. Biol. Chem.*, 278:46974-46982, 2003.
Garinot-Schneider et al., *J. Mol. Biol.*, 260:731-742, 1996.
GB Appln. 2 202 328
Georgiou and Segatori, *Current Opin. Biotech.*, 16:538-545, 2005.
Ghetie and Ward, *Annu. Rev. Immunol.*, 18:739-766, 2000.
Ghetie and Ward, *Annu. Rev. Immunol.*, 18:739-766, 2000.
Golay et al., *Blood*, 95:3900-3908, 2000.
Gomi et al., *J. Immunol.*, 144:4046-4052, 1990.
Gopal, *Mol. Cell Biol.*, 5:1188-1190, 1985.
Graham and Van Der Eb, *Virology*, 52:456-467, 1973.
Griffiths and Duncan, *Curr. Opin. Biotechnol.*, 9:102-108, 1998.
Guddat et al., *Proc. Natl. Acad. Sci. USA*, 90:4271-4275, 1993.
Gulbis and Galand, *Hum. Pathol.*, 24(12):1271-1285, 1993.
Guzman et al., *J. Bacteriol.*, 177:4121-30, 1995.
Guzman et al., *J. Bacteriol.*, 177:4121-4130, 1995.
Halloran et al., *J. Immunol.*, 153:2631-2641, 1994.
Harland and Weintraub, *J. Cell Biol.*, 101(3):1094-1099, 1985.
Harvey et al., *Proc. Natl. Acad. Sci. USA*, 101:9193-9198, 2004.
Harvey et al., *J. Immunol. Methods.* 308:43-52, 2006.
Hayhurst et al., *J. Immunol. Methods*, 276:185-196, 2003.
Hayhurst et al., *J. Immunol. Methods*, 276:185-196, 2003.
Hayhurst et al., *J. Immunol. Methods*, 276:185-196, 2003.
Hobot et al., *J. Bacteriol.*, 160:143, 1984.
Hoogenboom et al., *Immunotechnology*, 4:1-20, 1998.
Hoogenboom and Winter, *J. Mol. Biol.*, 227:381-388, 1992.
Hoover and Lubkowski, *Nucl. Acids Res.*, 30:e43, 2002.
Hoover and Lubkowski, *Nucleic Acids Res.*, 30:e43, 2002.
Hughes-Jones and Gardner, *Mol. Immunol.*, 16:697-701, 1979.
Idusogie et al., *J. Immunol.*, 166:2571-2575, 2001.
Innis et al., *Proc. Natl. Acad. Sci. USA*, 85(24):9436-9440, 1988.
Irvin et al., *J. Bacteriol.*, 145:1397, 1981.
Jefferis, *Biotechnol. Prog.*, 21:11-16, 2005.
Jefferis, *Adv. Exp. Med. Biol.*, 564:143-148, 2005.
Jeong and Lee, *Appl. Environ. Microbiol.*, 69:1295-1298, 2003.
Jouenne and Junter, *FEMS Microbiol. Lett.*, 56:313, 1990.
Jung et al., *Biotechnol Bioeng*, 98:39-47, 2007
Jung et al., *Protein Expr. Purif.*, 31:240-246, 2003.
Jung et al., *Proc. Natl. Acad. Sci. USA*, 107:604-609, 2010.
Jung et al., *ACS Chem. Biol.*, 8:368-375, 2012.
Kabat et al., In: *Sequences of Proteins of Immunological Interest*, U.S. Dept. of Health and Hum. Serv., Bethesda, 1991.
Kaeppler et al., *Plant Cell Reports*, 9:415-418, 1990.
Kalergis and Ravetch, *J. Exp. Med.*, 195:1653-1659, 2002.
Kaneda et al., *Science*, 243:375-378, 1989.
Kato et al, *J. Biol. Chem.*, 266:3361-3364, 1991.
Kawarasaki et al., *Nucleic Acids Res.*, 31:e126, 2003.
Khatoon et al., *Ann. Neurol*, 26(2):210-215, 1989.
Kim et al., *Eur. J. Immunol.*, 24:2429-2434, 1994.
King et al., *J. Biol. Chem.*, 264(17):10210-10218, 1989.
Kipriyanov and Little, *Mol. Biotechnol.*, 12:173-201, 1999.
Kjaer et al., *FEBS Lett.*, 431:448-452, 1998.
Knight et al., *Mol. Immunol.*, 32:1271-1281, 1995.
Kohler and Milstein, *Nature*, 256:495-497, 1975.
Kouzarides and Ziff, *Nature*, 336:646-6451, 1988.
Kuroda et al., *Lancet.*, 357:1225-1240, 2001.
Kwoh et al., *Proc. Natl. Acad. Sci. USA*, 86:1173, 1989.
Labischinski et al., *J. Bacteriol.*, 162:9, 1985.
Landschulz et al., *Science*, 240:1759-1764, 1988.
Lanio and Jeltsch, *Biotechniques*, 25:962-955, 1998.
Lazar et al., *Proc. Natl. Acad. Sci. USA*, 103:4005-4010, 2006.
Lazar et al., *Proc. Natl. Acad. Sci. USA*, 103:4005-4010, 2006.
Lei et al., *J. Bacteriol.*, 169:4379-4383, 1987.
Levenson et al., *Hum. Gene Ther.*, 9(8):1233-1236, 1998.
Leysath et al., *J. Mol. Biol.*, 387:680-693, 2009.
Li et al., *J. Mol. Biol.*, 337:743-759, 2004.
Maniatis, et al., *Molecular Cloning, A Laboratory Manual*, Cold Spring Harbor Press, Cold Spring Harbor, N.Y., 1988.
Marciano et al., *Science*, 284:1516, 1999.
Masaki et al., *Nucleic Acids Res.*, 13:1623-1635, 1985.
Mazor et al., *Nat. Biotech.*, 25(5):563-565, 2007.
Mazor et al., *Nat. Biotech.*, 25:563-5, 2007.
Michaelsen et al., *Scand. J. Immunol.*, 70:553-564, 2009.
Moore et al., *mAbs*, 2:181-189, 2010.
Munson and Pollard, *Anal. Biochem.*, 107:220, 1980.

Nagaoka and Akaike, Protein Engineering, 16: 243-245, 2003.
Natsume et al., Cancer Res., 68:3863-3872, 2008.
Nicolau and Sene, Biochim. Biophys. Acta, 721:185-190, 1982.
Nicolau et al., Methods Enzymol., 149:157-176, 1987.
Nikaido and Nakae, Adv. Microb. Physiol., 20:163, 1979.
Nikaido and Vaara, Microbiol. Rev., 49:1, 1985.
Nikaido, J. Bacteriology, 178(20):5853-5859, 1996.
O'Brien et al., Protein Expr. Purif., 24:43-50, 2002.
Ober et al., J. Immunol., 172:2021-2029, 2004b.
Ober et al., Proc. Natl. Acad. Sci. USA, 101:11076-11081, 2004a.
Olsson et al., Eur. J. Biochem., 168:319-324, 1987.
Orlandi et al., Proc. Natl. Acad. Sci. USA, 86:3833-3837, 1989.
Osborn et al., J. Biol. Chem, 247:3973-3986, 1972.
Owens and Haley, Biochem. Biophys. Res. Commun., 142(3):964-971, 1987.
Painbeni et al., Proc Natl. Acad. Sci. USA, 94:6712, 1997.
Pavlou and Belsey, Eur. J. Pharm. Biopharm., 59:389-396, 2005.
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 93/06213
PCT Appln. WO 94/09699
PCT Appln. WO 95/06128
Potrykus et al., Mol. Gen. Genet., 199(2):169-177, 1985.
Potter and Haley, Methods Enzymol, 91:613-633, 1983.
Purvis et al., Appl. Environ. Microbiol., 71:3761-3769, 2005.
Raghavan and Bjorkman, Annu. Rev. Cell Dev. Biol., 12:181-220, 1996.
Rao and Torriani, J. Bacteriol., 170, 5216, 1988.
Ramsland et al., J. Immunol., 187:3208-3217, 2011.
Rankin et al., Blood 108: 2384-2391, 2006.
Ravetch and Perussia et al., J. Exp. Med., 170:481-497, 1989.
Ravetch et al., Science, 234:718-725, 1986.
Rippe, et al., Mol. Cell Biol., 10:689-695, 1990.
Rodewald, J. Cell Biol., 71:666-669, 1976.
Ruhlmann et al., FEBS Lett., 235:262-266, 1988.
Sambrook et al., In: Molecular cloning: a laboratory manual, 2$^{nd}$ Ed., Cold Spring Harbor Laboratory Press, Cold Spring Harbor, N.Y., 1989.
Sazinsky et al., Proc. Natl. Acad. Sci. USA, 105:20167-20172, 2008.
Schierle et al., J. Bacteriol., 185:5706-5713, 2003.
Schneider and Zacharias, Mol. Immunol., 51:66-72, 2012.
Sears et al., J. Immunol., 144:371-378, 1990.
Sergina and Moasser, Trends in Molec. Med., 13:527-534, 2007.
Sergina, and Moasser, Trends in Molec. Med., 13:527-534, 2007.
Shields et al., J. Biol. Chem., 276:6591-6604, 2001.
Shuttleworth et al., Gene, 58(2-3):283-295, 1987.
Simister and Mostov, Nature, 337(6203):184-187, 1989.
Sledge and Bing, J. Biol. Chem., 248:2818-2823, 1973.
Sondermann et al., J. Mol. Biol., 309:737-749, 2001.
Stenberg et al., Mol. Microbiol., 6:1185-1194, 1992.
Stengelin et al., Embo J, 7:1053-1059, 1988.
Stuart et al., Embo J., 8:3657-3666, 1989.
Stuart et al., J. Exp. Med., 166:1668-1684, 1987.
Tominaga et al., Biochem. Biophys. Res. Commun., 168:683-689, 1990.
Uhlen et al., J. Biol. Chem., 259:1695-702, 1984.
Van Wielink and Duine, Trends Biochem Sci., 15:136, 1990.
Wada et al., J. Biol. Chem., 274:17353-17357, 1999.
Walker et al., Nucleic Acids Res., 20(7):1691-1696, 1992.
Wong et al., Gene, 10:87-94, 1980.
Wright and Morrison, Trends Biotechnol., 15:26-32, 1997.
Zeger et al., Proc. Natl. Acad. Sci. USA, 87:3425-3429, 1990.
Zhang et al., Immunogenetics, 39:423-437, 1994.
Zhang et al., Microbiology, 144(Pt 4):985-991, 1998.
Zohair et al., Biochem. J., 257:865-873, 1989.
U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 5,889,155
U.S. Pat. No. 7,109,304
U.S. Pat. No. 8,465,743
U.S. Pat. Publn. 2009/0304666
WO 2012/031744
WO 2012/079000
WO 2013/059593
Ahmed et al., HER2-specific T cells target primary glioblastoma stem cells and induce regression of autologous experimental tumors. Clinical Cancer Research, 16(2): 474-485, 2010.
Austin-Ward and Villaseca, Revista Medica de Chile, 126(7):838-845, 1998.
Ausubel et al., Current Protocols in Molecular Biology, Greene Publishing Associates and Wiley Interscience, N.Y., 1994.
Bukowski et al., Clinical Cancer Res., 4(10):2337-2347, 1998.
Chen and Guillemin, Kynurenine pathway metabolites in humans: disease and healthy States. Int J Tryptophan Res, 2:1-19, 2009.
Christodoulides et al., Microbiology, 144(Pt 11):3027-3037, 1998.
Curran et al., PD-1 and CTLA-4 combination blockade expands infiltrating T cells and reduces regulatory T and myeloid cells within B16 melanoma tumors. Proceedings of the National Academy of Sciences, 107:4275-4280, 2010.
Davidson et al., J. Immunother 21(5):389-398, 1998.
de Jong et al., Serum tryptophan and kynurenine concentrations as parameters for indoleamine 2,3-dioxygenase activity in patients with endometrial, ovarian, and vulvar cancer. Int J Gynecol Cancer, 21(7):1320-1327, 2011.
Della Chiesa et al., The tryptophan catabolite L-kynurenine inhibits the surface expression of NKp46- and NKG2D-activating receptors and regulates NK-cell function. Blood, 108(13):4118-4125, 2006.
Godin-Ethier et al., Indoleamine 2, 3-Dioxygenase Expression in Human Cancers: Clinical and Immunologic Perspectives. Clinical Cancer Research, 17(22):6985-6991, 2011.
Hanibuchi et al., Int. J. Cancer, 78(4):480-485, 1998.
Harkki et al., BioTechnology, 7:596-603, 1989.
Hellstrand et al., Acta Oncologica, 37(4):347-353, 1998.
Hollander, Front. Immun., 3:3, 2012.

Holmgaard et al., Indoleamine 2, 3-dioxygenase is a critical resistance mechanism in antitumor T cell immunotherapy targeting CTLA-4. *The Journal of Experimental Medicine,* 210:1389-1402, 2013.

Hoover and Lubkowski, DNAWorks: an automated method for designing oligonucleotides for PCR-based gene synthesis. *Nucleic Acids Research,* 30(10):e43-e43, 2002.

Hopwood et al., In: *Genetic Manipulation of Streptomyces,* A Laboratory Manual, The John Innes Foundation, Norwich, Conn., 1985.

Hui and Hashimoto, *Infection Immun.,* 66(11):5329-5336, 1998.

Ito et al., *J. Biochem.,* 79:1263, 1976.

Janeway et al., *Immunobiology: The Immune System in Health and Disease.* 6th Edition. New York: Garland Publishing, 2005.

Kaper et al., Nanosensor detection of an immunoregulatory tryptophan influx/kynurenine efflux cycle. *PLoS Biology,* 5(10):e257, 2007.

Lipowska-Bhalla et al., Targeted immunotherapy of cancer with CAR T cells: achievements and challenges. *Cancer Immunology Immunotherapy,* 61(7): 953-962, 2012.

Lob et al., Inhibitors of indoleamine-2,3-dioxygenase for cancer therapy: can we see the wood for the trees? *Nat Rev Cancer,* 9(6):445-452, 2009.

Lordanescu, *J. Bacteriol,* 12:597 601, 1975.

Mandi and Vecsei, The kynurenine system and immunoregulation. *J Neural Transm,* 119(2):197-209, 2012.

Maniatis, et al., Molecular Cloning, A Laboratory Manual, Cold Spring Harbor Press, Cold Spring Harbor, N.Y., 1988.

Mellor et al., *Gene,* 24:1-14, 1983.

Mezrich et al., An interaction between kynurenine and the aryl hydrocarbon receptor can generate regulatory T cells. *The Journal of Immunology,* 185(6):3190-3198, 2010.

Opitz et al., The Indoleamine-2, 3-Dioxygenase (IDO) Inhibitor 1-Methyl-D-tryptophan Upregulates IDO1 in Human Cancer Cells. *PLoS One,* 6(5):e19823, 2011.

Opitz et al., An endogenous tumour-promoting ligand of the human aryl hydrocarbon receptor. *Nature,* 478(7368): 197-203, 2011.

Penttila et al., *Gene,* 61:155-164, 1987.

Pilotte et al., Reversal of tumoral immune resistance by inhibition of tryptophan 2,3-dioxygenase. *Proc Natl Acad Sci USA,* 109(7):2497-2502, 2012.

Prendergast, Cancer: Why tumours eat tryptophan. *Nature,* 478(7368):192-194, 2011.

Qin et al., *Proc. Natl. Acad. Sci. USA,* 95(24):14411-14416, 1998.

Remington's Pharmaceutical Sciences, 18th Ed. Mack Printing Company, 1289-1329, 1990.

Rutella et al., Targeting indoleamine 2,3-dioxygenase (IDO) to counteract tumour-induced immune dysfunction: from biochemistry to clinical development. *Endocr Metab Immune Disord Drug Targets,* 9(2):151-177, 2009.

Schellenberger et al., *Nature* Biotech., 27:1186-1190, 2009.

Shin et al., Modulation of natural killer cell antitumor activity by the aryl hydrocarbon receptor. *Proc Natl Acad Sci USA,* 110(30):12391-12396, 2013.

Sibakov et al., *Eur. J Biochem.,* 145:567 572, 1984.

Song et al., L-Kynurenine-induced apoptosis in human NK cells is mediated by reactive oxygen species. *International Immunopharmacology,* 11(8): 932-938, 2011.

Stone et al., Replacing $Mn^{2-}$ with $Co^{2+}$ in human arginase I enhances cytotoxicity toward L-arginine auxotrophic cancer cell lines. *ACS Chemical Biology,* 5:333-342, 2010.

Walport, Complement. First of two parts. *N. Engl. J. Med.,* 344:1058-1066, 2001.

Walport, Complement. Second of two parts. *N. Engl. J. Med.,* 344:1140-1144, 2001.

Ward, Proc, Embo-Alko Workshop on Molecular Biology of Filamentous Fungi, Helsinki, 119-128, 1989.

Wawrzynczak and Thorpe, In: *Immunoconjugates, Antibody Conuugates In Radioimaging And Therapy Of Cancer,* Vogel (Ed.), NY, Oxford University Press, 28, 1987.

Yao et al., Serum metabolic profiling and features of papillary thyroid carcinoma and nodular goiter. *Mol Biosyst,* 7(9):2608-2614, 2011.

Yoshikawa et al., Serum concentration of L-kynurenine predicts the clinical outcome of patients with diffuse large B-cell lymphoma treated with R-CHOP. *Eur J Haematol,* 84(4):304-309, 2010.

---

What is claimed is:

1. A polypeptide comprising an aglycosylated variant human IgG Fc domain capable of binding human C1q, wherein the Fc domain comprises amino acid substitutions selected from the group consisting of:
   (a) K320E and Q386R,
   (b) L235K, G236M, G237R, and L351Q,
   (c) V308A, S337P, K338Q, K340R, Q342P, R344G, E345Y, and F372L,
   (d) M252V, G341A, and L351Q,
   (e) M252V, K246N, K322E, R344G, E345Y, and F372L,
   (f) M252V, F242L, K338Q, G341A, and E345Y, and
   (g) F242L, M252V, K338Q, G341A, and E345Y;
wherein the numbering of the residues in the Fc domain is that of the EU index as in Kabat.

2. The polypeptide of claim 1, wherein the polypeptide does not detectably bind Fcγ receptors.

3. The polypeptide of claim 1, wherein the polypeptide has specific affinity for binding human C1q and activating Fc receptors.

4. The polypeptide of claim 3, wherein the polypeptide does not detectably bind FcγRIIb.

5. The polypeptide of claim 1, wherein the aglycosylated variant human IgG Fc domain comprises substitutions K320E and Q386R.

6. The polypeptide of claim 5, wherein the aglycosylated variant human IgG Fc domain is Fc801 (SEQ ID NO: 7).

7. The polypeptide of claim 1, wherein the aglycosylated variant human IgG Fc domain comprises substitutions L235K, G236M, G237R, and L351Q.

8. The polypeptide of claim 7, wherein the aglycosylated variant human IgG Fc domain is Fc802 (SEQ ID NO: 10).

9. The polypeptide of claim 3, wherein the aglycosylated variant human IgG Fc domain comprises substitutions V308A, S337P, K338Q, K340R, Q342P, R344G, E345Y, and F372L.

10. The polypeptide of claim 9, wherein the aglycosylated variant human IgG Fc domain is Fc805 (SEQ ID NO: 22).

11. The polypeptide of claim 1, wherein the aglycosylated variant human IgG Fc domain further comprises the substitutions M252V, G341A, and L351Q.

12. The polypeptide of claim 11, wherein the aglycosylated variant human IgG Fc domain is Fc-V18 (SEQ ID NO: 41).

13. The polypeptide of claim 1, wherein the aglycosylated variant human IgG Fc domain further comprises the substitutions K246N, K322E, R344G, E345Y, F372L, and M252V.

14. The polypeptide of claim 13, wherein the aglycosylated variant human IgG Fc domain is Fc-V23 (SEQ ID NO: 43).

15. The polypeptide of claim 1, wherein the aglycosylated variant human IgG Fc domain comprises the substitutions F242L, M252V, K338Q, G341A, and E345Y.

16. The polypeptide of claim 15, wherein the aglycosylated variant human IgG Fc domain is Fc-V24 (SEQ ID NO: 44).

* * * * *

SEQUENCE LISTING

```
<160> NUMBER OF SEQ ID NOS: 45

<210> SEQ ID NO 1
<211> LENGTH: 216
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 2
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu His Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Val Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Ile His Glu Ala Leu His Asn His Tyr Thr Gln
        195                 200                 205

Lys Ser Leu Ser Pro Val Pro Gly
    210                 215
```

```
<210> SEQ ID NO 3
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 3

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Gln Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 4
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 4

Ala Pro Leu Leu Leu Glu Gly Pro Ser Ala Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Tyr Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Ala Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Gln Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 5
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 5

Ala Pro Leu Leu Leu Glu Gly Pro Ser Ala Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Tyr Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Ala Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

```
<210> SEQ ID NO 6
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 6
```

Ala Pro Glu Leu Leu Gly Val Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Gly Tyr Lys Cys Lys Val Ser Asn Lys
                85                  90                  95

Ala Pro Pro Ala Pro Ile Glu Lys Thr Phe Leu Ser Val Leu Arg Leu
            100                 105                 110

Pro Leu Glu Pro Gln Val Tyr Thr Leu Pro Pro Ser Gln Gly Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

```
<210> SEQ ID NO 7
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 7
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Glu Cys Lys Val Ser Asn Lys
                85                  90                  95

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Arg Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 8
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 8

Ala Pro Glu Leu Leu Gly Gly Pro Ser Val Phe Leu Phe Pro Pro Lys
1               5                   10                  15

Pro Lys Asp Thr Phe Met Ile Ser Arg Thr Pro Glu Val Thr Cys Met
            20                  25                  30

Val Val Asp Val Gly His Glu Asp Pro Glu Val Lys Phe Asn Trp Tyr
        35                  40                  45

Val Asp Gly Val Glu Val His Asn Ala Lys Thr Lys Ser Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Leu Ala His Ala Arg Gly Pro
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Pro Val Lys Gly Leu Tyr Pro
    130                 135                 140

Ser Asp Ile Ala Val Glu Arg Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Ser Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 9
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 9

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Gln His
65                  70                  75                  80

Gln Asp Trp Leu Asn Gly Lys Glu Tyr Lys Cys Lys Val Ser Asn Lys
                85                  90                  95

Ala Pro Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Pro Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met Leu Gly Ala Leu His Asn His Tyr Thr Gln
        195                 200                 205

Lys Ser Leu Ser Leu Ser Pro Gly
    210                 215
```

<210> SEQ ID NO 10
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 10

```
Ala Pro Glu Leu Lys Met Arg Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Thr Gln Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 11
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 11

Ala Pro Glu Ile Val Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Gly His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Ile Ala Arg Gly Pro
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Ser Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Arg Ser Leu Ser Leu Ser Pro Gly
    210                 215
```

```
<210> SEQ ID NO 12
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 12
```

| | | | | | | | | | | | | | | | |
|---|---|---|---|---|---|---|---|---|---|---|---|---|---|---|---|
| Ala | Pro | Glu | Leu | Leu | Gly | Gly | Pro | Ser | Val | Phe | Leu | Phe | Pro | Pro | Lys |
| 1 | | | | 5 | | | | | 10 | | | | | 15 | |
| Pro | Lys | Asp | Thr | Leu | Met | Ile | Ser | Arg | Thr | Pro | Glu | Val | Thr | Cys | Val |
| | | | 20 | | | | | 25 | | | | | 30 | | |
| Val | Val | Asp | Val | Ser | His | Glu | Gly | Pro | Glu | Val | Lys | Phe | Asn | Trp | Tyr |
| | | 35 | | | | | 40 | | | | | 45 | | | |
| Val | Asp | Gly | Val | Glu | Val | His | Asn | Ala | Lys | Thr | Lys | Pro | Arg | Glu | Glu |
| | 50 | | | | | 55 | | | | | 60 | | | | |
| Gln | Tyr | Asn | Ser | Thr | Tyr | Arg | Val | Val | Ser | Val | Leu | Thr | Val | Leu | His |
| 65 | | | | | 70 | | | | | 75 | | | | | 80 |
| Gln | Asp | Trp | Leu | Asn | Gly | Lys | Glu | Tyr | Lys | Cys | Lys | Val | Ser | Asn | Lys |
| | | | | 85 | | | | | 90 | | | | | 95 | |
| Ala | Leu | Pro | Ala | Pro | Ile | Glu | Lys | Thr | Arg | Ser | Lys | Ala | Arg | Gly | Pro |
| | | | 100 | | | | | 105 | | | | | 110 | | |
| Pro | Leu | Asp | Pro | Gln | Val | Tyr | Thr | Leu | Pro | Pro | Ser | Arg | Asp | Glu | Leu |
| | | | 115 | | | | | 120 | | | | | 125 | | |
| Thr | Lys | Asn | Gln | Val | Ser | Leu | Thr | Cys | Leu | Val | Lys | Gly | Phe | Tyr | Pro |
| | | | 130 | | | | | 135 | | | | | 140 | | |
| Ser | Asp | Ile | Ala | Val | Glu | Trp | Glu | Ser | Asn | Gly | Gln | Pro | Glu | Asn | Asn |
| 145 | | | | | 150 | | | | | 155 | | | | | 160 |
| Tyr | Lys | Thr | Thr | Pro | Pro | Val | Leu | Asp | Ser | Asp | Gly | Ser | Phe | Phe | Leu |
| | | | | 165 | | | | | 170 | | | | | 175 | |
| Tyr | Ser | Lys | Leu | Thr | Val | Asp | Lys | Ser | Arg | Trp | Gln | Gln | Gly | Asn | Val |
| | | | 180 | | | | | 185 | | | | | 190 | | |
| Phe | Ser | Cys | Ser | Val | Met | His | Glu | Ala | Leu | His | Asn | His | Tyr | Thr | Gln |
| | | | 195 | | | | | 200 | | | | | 205 | | |
| Lys | Ser | Leu | Ser | Leu | Ser | Pro | Gly | | | | | | | | |
| | 210 | | | | | 215 | | | | | | | | | |

```
<210> SEQ ID NO 13
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 13
```

| | | | | | | | | | | | | | | | |
|---|---|---|---|---|---|---|---|---|---|---|---|---|---|---|---|
| Ala | Pro | Glu | Leu | Leu | Gly | Gly | Pro | Ser | Val | Phe | Leu | Phe | Pro | Pro | Lys |
| 1 | | | | 5 | | | | | 10 | | | | | 15 | |
| Pro | Lys | Asp | Thr | Leu | Met | Ile | Ser | Arg | Thr | Pro | Glu | Val | Thr | Cys | Val |
| | | | 20 | | | | | 25 | | | | | 30 | | |
| Val | Val | Asp | Val | Ser | His | Glu | Asp | Pro | Glu | Val | Lys | Phe | Asn | Trp | Tyr |
| | | 35 | | | | | 40 | | | | | 45 | | | |
| Val | Asp | Gly | Val | Glu | Val | His | Asn | Ala | Lys | Thr | Lys | Pro | Arg | Glu | Glu |
| | 50 | | | | | 55 | | | | | 60 | | | | |
| Gln | Tyr | Asn | Ser | Thr | Tyr | Arg | Val | Val | Ser | Val | Leu | Thr | Val | Leu | His |
| 65 | | | | | 70 | | | | | 75 | | | | | 80 |
| Gln | Asp | Trp | Leu | Asn | Gly | Lys | Glu | Tyr | Lys | Cys | Lys | Val | Ser | Asn | Lys |
| | | | | 85 | | | | | 90 | | | | | 95 | |

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Val Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Ile His Glu Ala Leu His Asn His Tyr Thr Gln
            195                 200                 205

Lys Ser Leu Ser Leu Ser Pro Gly
    210                 215

<210> SEQ ID NO 14
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 14

Ala Pro Asp Tyr Gln Lys Arg Pro Ser Val Phe Leu Phe Pro Pro Lys
1               5                   10                  15

Pro Lys Asp Ala Leu Met Val Ser Arg Thr Pro Glu Val Thr Cys Val
            20                  25                  30

Val Val Gly Val Ser His Glu Asp Pro Glu Val Lys Phe Asn Trp Tyr
        35                  40                  45

Val Asp Gly Val Glu Val Leu Asn Ala Lys Thr Lys Pro Arg Glu Glu
    50                  55                  60

Gln Tyr Ser Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Pro Tyr Lys Arg Lys
            100                 105                 110

Pro Arg Ala Pro Gln Val Tyr Thr Leu Pro Pro Ser Arg Asp Glu Leu
        115                 120                 125

Thr Arg Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Arg Gln Gly Asn Val
                180                 185                 190

Phe Ser Cys Ser Val Met His Glu Ala Leu His Asn His Tyr Ala Gln
            195                 200                 205

Lys Ser Leu Ser Leu Ser Pro Gly
    210                 215
```

```
<210> SEQ ID NO 15
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 15

Ala Pro Asp Tyr Gln Lys Arg Pro Ser Val Phe Leu Phe Pro Pro Lys
1               5                   10                  15

Pro Lys Asp Thr Leu Met Val Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Ser Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Pro Tyr Lys Arg Lys
            100                 105                 110

Pro Arg Ala Pro Gln Val Tyr Thr Leu Pro Pro Ser Arg Asp Glu Leu
        115                 120                 125

Thr Arg Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 16
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 16

Ala Pro Asp Tyr Gln Lys Arg Leu Ser Val Phe Leu Phe Pro Pro Lys
1               5                   10                  15

Pro Lys Asp Thr Leu Met Val Ser Arg Thr Pro Glu Val Thr Cys Val
            20                  25                  30

Val Val Asp Val Ser His Glu Asn Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Pro Val Leu His
65                  70                  75                  80

Gln Asp Trp Leu Ile Gly Lys Glu Tyr Lys Cys Lys Val Ser Asn Lys
                85                  90                  95
```

Ala Pro Pro Ala Pro Ile Glu Lys Thr Ile Ser Lys Ala Lys Gly His
            100                 105                 110

Pro Arg Glu Pro Gln Val Tyr Pro Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Ala Glu Trp Glu Ser Asn Gly Gln Pro Gly Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Arg Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 17
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 17

Ala Pro Asp Tyr Gln Lys Arg Pro Ser Val Phe Leu Phe Pro Pro Lys
1               5                   10                  15

Pro Lys Asp Thr Leu Met Val Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Arg
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Cys Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Gly Gly Ser Leu Phe Phe
                165                 170                 175

Tyr Ser Lys Leu Thr Val Asp Arg Ser Arg Trp Gln Gln Gly Asn Val
            180                 185                 190

Phe Ser Cys Ser Val Met His Glu Ala Leu His Asn His Cys Thr Gln
        195                 200                 205

Lys Ser Leu Ser Leu Ser Pro Gly
    210                 215

<210> SEQ ID NO 18
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 18

```
Ala Pro Gly Pro Pro Arg Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 19
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 19

```
Ala Pro Glu Leu Met Trp Arg Pro Ser Ile Phe Leu Phe Pro Pro Lys
1               5                   10                  15

Pro Lys Asp Thr Leu Met Ile Ser Arg Thr Pro Glu Val Thr Cys Val
            20                  25                  30

Met Val Asp Val Ser His Glu Asp Pro Glu Val Lys Phe Asn Trp Tyr
        35                  40                  45

Val Asp Gly Val Glu Val His Asn Ala Lys Thr Glu Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Pro Asn Lys
                85                  90                  95
```

```
Ala Leu Pro Ala Pro Ile Glu Lys Thr Ile Ser Lys Ala Lys Gly Gln
            100                 105                 110

Pro Arg Glu Pro Gln Val Tyr Ala Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Tyr Ser Val Met His Glu Ala Leu His Asn His Tyr Thr Gln
    195                 200                 205

Lys Ser Leu Ser Leu Ser Pro Gly
        210                 215

<210> SEQ ID NO 20
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 20

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Lys Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
    195                 200                 205

Lys Ser Leu Ser Leu Ser Ser Gly
        210                 215
```

-continued

```
<210> SEQ ID NO 21
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 21

Ala Pro Glu Leu Leu Gly Gly Pro Ser Val Phe Leu Phe Pro Pro Lys
1               5                   10                  15

Pro Lys Asp Thr Leu Val Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Asn Lys
                85                  90                  95

Ala Leu Pro Ala Pro Ile Glu Lys Thr Met Ser Lys Ala Arg Gly Asp
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 22
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 22

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Ala Leu His
65                  70                  75                  80

Gln Asp Trp Leu Asn Gly Lys Glu Tyr Lys Cys Lys Val Ser Asn Lys
                85                  90                  95
```

```
Ala Leu Pro Ala Pro Ile Glu Lys Thr Ile Pro Gln Ala Arg Gly Pro
            100                 105                 110

Pro Gly Tyr Pro Gln Val Tyr Thr Leu Pro Pro Ser Arg Asp Glu Leu
        115                 120                 125

Thr Lys Asn Gln Val Ser Leu Thr Cys Leu Val Lys Gly Leu Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 23
<211> LENGTH: 216
<212> TYPE: PRT
<213> ORGANISM: Artificial Sequence
<220> FEATURE:
<223> OTHER INFORMATION: Synthetic polypeptide

<400> SEQUENCE: 23

Ala Pro Glu Leu Leu Trp Leu Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Glu His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Val Glu Lys Thr Ala Ser Lys Ala Glu Gly Gln
            100                 105                 110

Leu Ser Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
gttattactc gcggcccagc cg                                              22

<210> SEQ ID NO 25
<211> LENGTH: 55
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(55)
<223> OTHER INFORMATION: N is any nucleotide

<400> SEQUENCE: 25
ggggaagagg aagactgacg gnnnnnnnnn nnnnnnaggt gctgggcacg gtggg          55

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
ccgtcagtct tcctcttccc c                                               21

<210> SEQ ID NO 27
<211> LENGTH: 22
<212> TYPE: DNA
<213> ORGANISM: Artificial Sequence
<220> FEATURE:
<223> OTHER INFORMATION: Synthetic primer

<400> SEQUENCE: 27
ggttttctcg atggggctg gg                                               22

<210> SEQ ID NO 28
<211> LENGTH: 73
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(73)
<223> OTHER INFORMATION: N is any nucleotide

<400> SEQUENCE: 28
cccagccccc atcgagaaaa ccnnnnnnnn nnnnnnnnnn nnnnnnnnnn nnccacaggt     60
gtacaccctg ccc                                                        73

<210> SEQ ID NO 29
<211> LENGTH: 19
<212> TYPE: DNA
<213> ORGANISM: Artificial Sequence
<220> FEATURE:
<223> OTHER INFORMATION: Synthetic primer

```
<400> SEQUENCE: 29
cggccgcgaa ttcggcccc                                              19

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
ggggaagagg aagactgacg g                                           21

<210> SEQ ID NO 31
<211> LENGTH: 22
<212> TYPE: DNA
<213> ORGANISM: Artificial Sequence
<220> FEATURE:
<223> OTHER INFORMATION: Synthetic primer

<400> SEQUENCE: 31
ggttttctcg atgggggctg gg                                          22

<210> SEQ ID NO 32
<211> LENGTH: 23
<212> TYPE: DNA
<213> ORGANISM: Artificial Sequence
<220> FEATURE:
<223> OTHER INFORMATION: Synthetic primer

<400> SEQUENCE: 32
caccaaggtc gacaagaaag ttg                                         23

<210> SEQ ID NO 33
<211> LENGTH: 60
<212> TYPE: DNA
<213> ORGANISM: Artificial Sequence
<220> FEATURE:
<223> OTHER INFORMATION: Synthetic primer

<400> SEQUENCE: 33
ctcgagcggc cgctcattta cccggggaca gggagaggtt tacccgggga cagggagagg  60

<210> SEQ ID NO 34
<211> LENGTH: 38
<212> TYPE: DNA
<213> ORGANISM: Artificial Sequence
<220> FEATURE:
<223> OTHER INFORMATION: Synthetic primer

<400> SEQUENCE: 34
gccgcgggag gagcagtaca acagcctgta ccgtgtgg                         38

<210> SEQ ID NO 35
<211> LENGTH: 41
<212> TYPE: DNA
<213> ORGANISM: Artificial Sequence
<220> FEATURE:
<223> OTHER INFORMATION: Synthetic primer

<400> SEQUENCE: 35
gtgaggacgc tgaccacacg gtacaggctg ttgtactgct c                     41
```

```
<210> SEQ ID NO 36
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 36
```

Ala Pro Glu Leu Leu Gly Gly Pro Ser Val Phe Leu Phe Pro Pro Lys
1               5                   10                  15

Pro Lys Asp Thr Leu Val Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

```
<210> SEQ ID NO 37
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 37
```

Ala Pro Glu Leu Leu Gly Gly Pro Ser Val Phe Leu Phe Pro Pro Asn
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Glu Val Ser Asn Lys
                85                  90                  95

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Ser Phe Phe Leu
            165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215

<210> SEQ ID NO 38
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 38

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Glu Thr Ile Ser Lys Ala Lys Gly Gln
            100                 105                 110

Pro Arg Glu Pro Gln Val Tyr Thr Gln Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asp Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
        210                 215
```

-continued

```
<210> SEQ ID NO 39
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 39
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Ala Gln
            100                 105                 110

Pro Arg Glu Pro Gln Val Tyr Thr Gln Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Cys Met His Glu Ala Leu His Asn His Tyr Thr Gln
        195                 200                 205

Lys Ser Leu Ser Leu Ser Pro Gly Lys
    210                 215

```
<210> SEQ ID NO 40
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 40
```

Ala Pro Glu Leu Leu Gly Gly Pro Ser Val Phe Leu Phe Pro Pro Lys
1               5                   10                  15

Pro Lys Asp Thr Leu Val Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

```
Ala Leu Pro Ala Pro Ile Glu Lys Thr Ile Ser Lys Ala Lys Ala Gln
            100                 105                 110

Pro Arg Glu Pro Gln Val Tyr Thr Gln Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
    210                 215

<210> SEQ ID NO 41
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 41

Ala Pro Glu Leu Leu Gly Gly Pro Ser Val Phe Leu Phe Pro Pro Gln
1               5                   10                  15

Pro Lys Asp Thr Leu Met Ile Ser Arg Thr Pro Glu Val Ala Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Arg Pro Glu Asn Asn
145                 150                 155                 160

Tyr Lys Thr Thr Pro Pro Val Leu Asp Ser Asp Gly Ser Phe Phe Leu
            165                 170                 175

Tyr Ser Lys Leu Thr Val Asp Lys Ser Arg Trp Gln Gln Gly Asn Val
        180                 185                 190

Phe Ser Cys Ser Val Met His Glu Ala Leu His Asn His Tyr Thr Gln
    195                 200                 205

Lys Ser Leu Ser Leu Ser Pro Gly Lys
    210                 215
```

-continued

```
<210> SEQ ID NO 42
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 42

Ala Pro Glu Leu Leu Gly Gly Pro Ser Val Phe Leu Leu Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Asn Lys
                85                  90                  95

Ala Leu Pro Ala Pro Ile Glu Lys Thr Met Ser Lys Ala Arg Gly Asp
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Thr Val Glu Trp Glu Ser Asn Gly Arg Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 43
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 43

Ala Pro Glu Leu Leu Gly Gly Pro Ser Val Phe Leu Phe Pro Pro Asn
1               5                   10                  15

Pro Lys Asp Thr Leu Val Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Glu Val Ser Asn Lys
                85                  90                  95
```

```
Ala Leu Pro Ala Pro Ile Glu Lys Thr Ile Ser Lys Ala Lys Gly Gln
            100                 105                 110

Pro Gly Tyr Pro Gln Val Tyr Thr Leu Pro Pro Ser Arg Asp Glu Leu
        115                 120                 125

Thr Lys Asn Gln Val Ser Leu Thr Cys Leu Val Lys Gly Leu Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 44
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 44

Ala Pro Glu Leu Leu Gly Gly Pro Ser Val Phe Leu Leu Pro Pro Lys
1               5                   10                  15

Pro Lys Asp Thr Leu Val Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Gln Ala Lys Ala Gln
            100                 105                 110

Pro Arg Tyr Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

```
<210> SEQ ID NO 45
<211> LENGTH: 217
<212> TYPE: PRT
<213> ORGANISM: Artificial Sequence
<220> FEATURE:
<223> OTHER INFORMATION: Synthetic polypeptide

<400> SEQUENCE: 45

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Glu Thr Ile Ser Gln Ala Lys Gly Pro
            100                 105                 110

Pro Gly Tyr Pro Gln Val Tyr Thr Leu Pro Pro Ser Arg Asp Glu Leu
        115                 120                 125

Thr Lys Asn Gln Val Ser Leu Thr Cys Leu Val Lys Gly Leu Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```